(12) United States Patent
Kufe

(10) Patent No.: US 7,931,904 B2
(45) Date of Patent: Apr. 26, 2011

(54) MODULATION OF MUC1 ACTIVITY

(75) Inventor: Donald W. Kufe, Wellesley, MA (US)

(73) Assignee: Dana Farber Cancer Institute, Inc., Boston, MA (US)

( * ) Notice: Subject to any disclaimer, the term of this patent is extended or adjusted under 35 U.S.C. 154(b) by 102 days.

(21) Appl. No.: 11/816,402

(22) PCT Filed: Feb. 14, 2006

(86) PCT No.: PCT/US2006/005239
§ 371 (c)(1),
(2), (4) Date: May 2, 2008

(87) PCT Pub. No.: WO2006/088906
PCT Pub. Date: Aug. 24, 2006

(65) Prior Publication Data
US 2008/0286264 A1    Nov. 20, 2008

Related U.S. Application Data

(60) Provisional application No. 60/652,918, filed on Feb. 15, 2005, provisional application No. 60/654,009, filed on Feb. 17, 2005.

(51) Int. Cl.
*A61K 39/00*   (2006.01)
*A61K 39/38*   (2006.01)
*A61K 39/385*  (2006.01)
*A61K 38/00*   (2006.01)
*A61P 31/00*   (2006.01)

(52) U.S. Cl. ............... 424/184.1; 424/185.1; 424/193.1; 514/2

(58) Field of Classification Search ........................ None
See application file for complete search history.

(56) References Cited

U.S. PATENT DOCUMENTS

| | | | |
|---|---|---|---|
| 5,565,334 A | 10/1996 | Kufe et al. | 435/69.1 |
| 5,827,516 A | 10/1998 | Urban et al. | 424/93.21 |
| 5,874,415 A | 2/1999 | Kufe et al. | 514/44 |
| 6,093,573 A | 7/2000 | Beamer et al. | 436/86 |
| 6,613,883 B1 | 9/2003 | Harris et al. | 530/358 |
| 7,247,297 B2 | 7/2007 | Weichselbaum et al. | 424/93.2 |
| 2002/0110841 A1 | 8/2002 | Kufe | 435/7.23 |
| 2004/0018181 A1 | 1/2004 | Kufe et al. | 424/93.21 |
| 2004/0166543 A1 | 8/2004 | Kufe | 435/7.23 |
| 2005/0015232 A1 | 1/2005 | Reinherz et al. | 702/27 |
| 2005/0042209 A1 | 2/2005 | Kufe et al. | 424/93.21 |
| 2005/0053606 A1 | 3/2005 | Kufe et al. | 424/155.1 |
| 2005/0169898 A1 | 8/2005 | Gong et al. | 424/93.21 |
| 2005/0238627 A1 | 10/2005 | Ohno et al. | 424/93.21 |
| 2007/0105767 A1 | 5/2007 | Kharbanda et al. | 514/12 |
| 2007/0141704 A1 | 6/2007 | Nicolette et al. | 435/455 |
| 2007/0202134 A1 | 8/2007 | Kufe et al. | 424/277.1 |

FOREIGN PATENT DOCUMENTS

| | | |
|---|---|---|
| WO | WO 00/09744 | 2/2000 |
| WO | WO 00/11206 | 3/2000 |
| WO | WO 00/47763 | 8/2000 |
| WO | WO 2004/092339 | 10/2004 |

OTHER PUBLICATIONS

Asada et al., "Apoptosis inhibitory activity of cytoplasmic p21(Cip1/WAF1) in monocytic differentiation.," *EMBO J.*, 18:1223-1234, 1999.

Barlev et al., "Acetylation of p53 activates transcription through recruitment of coactivators/histone acetyltransferases," *Mol. Cell*, 8:1243-1254, 2001.

Barrios et al., "Mycobacterial heat-shock proteins as carrier molecules. II: The use of the 70-kDa mycobacterial heat-shock protein as carrier for conjugated vaccines can circumvent the need for adjuvants and Bacillus Calmette Guérin priming," *Eur. J. Immunol.*, 22:1365-1372, 1992.

Brody et al., "Aptamers as therapeutic and diagnostic agents," *Reviews in Molecular Biotechnology*, 74:5-13, 2000.

Chao et al., "p53 transcriptional activity is essential for p53-dependent apoptosis following DNA damage," *Embo J.*, 19:4967-4975, 2000.

Cristiano et al., "Molecular conjugates: a targeted gene delivery vector for molecular medicine," *J. Mol. Med.*, 73:479-486, 1995.

Dong et al., "Cytosolic p21Waf1/Cip1 increases cell cycle transit in vascular smooth muscle cells," *Cell Signal*, 16:263-269, 2004.

Dupont et al., "The cyclin-dependent kinase inhibitor p21CIP/WAF is a positive regulator of insulin-like growth factor I-induced cell proliferation in MCF-7 human breast cancer cells," *J. Biol. Chem.*, 278:37256-37264, 2003.

Duraisamy et al., "Distinct evolution of the human carcinoma-associated transmembrane mucins, MUC1, MUC4 and MUC16," *Gene*, 373:28-34, 2006.

El-Deiry et al., "WAF1, a potential mediator of p53 tumor suppression," *Cell*, 75:817-825, 1993.

Flores et al., "p63 and p73 are required for p53-dependent apoptosis in response to DNA damage," *Nature*, 416:560-564, 2002.

Gendler et al., "A highly immunogenic region of a human polymorphic epithelial mucin expressed by carcinomas is made up of tandem repeats," *J. Biol. Chem.*, 263:12820-12823, 1988.

Gronenborn et al., "Protein structure determination in solution by two-dimensional and three-dimensional nuclear magnetic resonance spectroscopy," *Anal. Chem.*, 62(1):2-15, 1990.

Hsieh et al., "Novel function of the cyclin A binding site of E2F in regulating p53-induced apoptosis in response to DNA damage," *Mol. Cell. Biol.*, 22:78-93, 2002.

Huang et al., "MUC1 cytoplasmic domain coactivates Wnt target gene transcription and confers transformation," *Cancer Biol. Ther.*, 2:702-706, 2003.

Hudson et al., "High avidity scFv multimers; diabodies and triabodies," *J. Immunol. Methods*, 231(1-2):177-189, 1999.

(Continued)

*Primary Examiner* — Anne M. Gussow
(74) *Attorney, Agent, or Firm* — Fulbright & Jaworski

(57) ABSTRACT

The invention provides methods of identifying and making compounds that inhibit the interaction between MUC1 and either p53 or TBP. Also embraced by the invention are in vivo and in vitro methods of inhibiting such an interaction and of inhibiting the expression of MUC1 by a cell.

8 Claims, 32 Drawing Sheets

OTHER PUBLICATIONS

Huston et al., "Engineered antibodies take center stage," *Hum. Antibodies*, 10(3-4):127-142, 2001.

J. Cavanagh et al., *Protein NMR Spectroscopy, Principles and Practice*, Academic Press, San Diego, 1996.

Jack et al., "Chk2 is dispensable for p53-mediated G1 arrest but is required for a latent p53-mediated apoptotic response," *Proc. Natl. Acad. Sci. USA*, 99:9825-9829, 2002.

Jimenez et al., "A transactivation-deficient mouse model provides insights into Trp53 regulation and function," *Nat. Genet.*, 26:37-43, 2000.

Kaeser et al., "Chromatin immunoprecipitation analysis fails to support the latency model for regulation of p53 DNA binding activity in vivo," *Proc. Natl. Acad. Sci. USA*, 99:95-100, 2002.

Kufe et al., "Differential reactivity of a novel monoclonal antibody (DF3) with human malignant versus benign breast tumors," *Hybridoma*, 3:223-232, 1984.

Levine, "p53, the cellular gatekeeper for growth and division," *Cell*, 88:323-331, 1997.

Li et al., "Human DF3/MUC1 carcinoma-associated protein functions as an oncogene," *Oncogene*, 22(38):6107-10, 2003.

Li et al., "Interaction of human MUC1 and beta-catenin is regulated by Lck and ZAP-70 in activated Jurkat T cells," *Biochem. Biophys. Res Commun.*, 315(2):471-6, 2004.

Li et al., "DF3/MUC1 signaling in multiple myeloma cells is regulated by interleukin-7," *Cancer Biol. Ther.*, 2:187-193, 2003.

Li et al., "Heregulin targets gamma-catenin to the nucleolus by a mechanism dependent on the DF3/MUC1 oncoprotein," *Mol. Cancer Res.*, 1:765-775, 2003.

Li et al., "The epidermal growth factor receptor regulates interaction of the human DF3/MUC1 carcinoma antigen with c-Src and beta-catenin," *J. Biol. Chem.*, 276:35239-35242, 2001.

Li et al., "The c-Src tyrosine kinase regulates signaling of the human DF3/MUC1 carcinoma-associated antigen with GSK3 beta and beta-catenin," *J. Biol. Chem.*, 276:6061-6064, 2001a.

Li et al., "Interaction of glycogen synthase kinase 3beta with the DF3/MUC1 carcinoma-associated antigen and beta-catenin," *Mol. Cell. Biol.*, 18:7216-7224, 1998.

Lightenberg et al., "Cell-associated episialin is a complex containing two proteins derived from a common precursor," *J. Biol. Chem.*, 267:6171-6177, 1992.

Liu et al., "The Activation Domains, the Proline-rich Domain, and the C-terminal Basic Domain in p53 Are Necessary for Acetylation of Histones on the Proximal p21 Promoter and Interaction with p300/CREB-binding Protein," *J. Biol. Chem.*, 278:17557-17565, 2003.

McPherson, "Crystallization of proteins from polyethylene glycol," *J. Biol. Chem.*, 251:6300-6306, 1976.

Merlo et al., "Frequent alteration of the DF3 tumor-associated antigen gene in primary human breat carcinomas," *Cancer Res.*, 49:6966-6971, 1989.

Miyashita et al., "Tumor suppressor p53 is a direct transcriptional activator of the human bax gene," *Cell*, 80:293-299, 1995.

Mujtaba et al., "Structural mechanism of the bromodomain of the coactivator CBP in p53 transcriptional activation," *Mol. Cell*, 13:251-263, 2004.

Muller et al., "p53 activates the CD95 (APO-1/Fas) gene in response to DNA damage by anticancer drugs," *J. Exp. Med.*, 188:2033-2045, 1998.

Oda et al., "p53AIP1, a potential mediator of p53-dependent apoptosis, and its regulation by Ser-46-phosphorylated p53," *Cell*, 102:849-862, 2000.

Oda et al., "Noxa, a BH3-only member of the Bcl-2 family and candidate mediator of p53-induced apoptosis," *Science*, 288:1053-1058, 2000.

Oren, "Decision making by p53: life, death and cancer," *Cell Death Differ.*, 10:431-442, 2003.

Perey et al., "Tumor selective reactivity of a monoclonal antibody prepared against a recombinant peptide derived from the DF3 human breast carcinoma-associated antigen," *Cancer Res.*, 52:2563-2568, 1992.

Poljak, "Production and structure of diabodies," *Structure*, 2(12):1121-1123, 1994.

Raina et al., "MUC1 oncoprotein blocks nuclear targeting of c-Abl in the a poptotic response to DNA damage," *EMBO J.*, 25(16):3774-83, 2006.

Raina et al., "The MUC1 oncoprotein activates the anti-apoptotic phosphoinositide 3-kinase/Akt and Bcl-xL pathways in rat 3Y1 fibroblasts," *J. Biol. Chem.*, 279(20):20607-12, 2004.

Ren et al., "Human MUC1 carcinoma-associated protein confers resistance to genotoxic anticancer agents," *Cancer Cell.*, 5(2):163-75, 2004.

Ren et al., "p73beta is regulated by protein kinase Cdelta catalytic fragment generated in the apoptotic response to DNA damage," *J. Biol. Chem.*, 277:33758-33765, 2002.

Ren et al., "Protein kinase C delta regulates function of the DF3/MUC1 carcinoma antigen in beta-catenin signaling," *J. Biol.Chem.*, 277:17616-17622, 2002.

Samuels-Lev et al., "ASPP proteins specifically stimulate the apoptotic function of p53," *Mol. Cell*, 8:781-794, 2001.

Schroeder et al., "Transgenic MUC1 interacts with epidermal growth factor receptor and correlates with mitogen-activated protein kinase activation in the mouse mammary gland," *J Biol Chem*, 276:13057-13064, 2001.

Shang et al., "Cofactor dynamics and sufficiency in estrogen receptor-regulated transcription," *Cell*, 103:843-852, 2000.

Shikama et al., "A novel cofactor for p300 that regulates the p53 response," *Mol. Cell*, 4:365-376, 1999.

Siddiqui et al., "Isolation and sequencing of a cDNA coding for the human DF3 breast carcinoma-associated antigen," *Proc. Natl. Acad. Sci. USA*, 85:2320-2323, 1988.

Stocks, "Intrabodies: production and promise," *Drug Discov. Today*, 9(22):960-966, 2004.

Vasir et al., "Dendritic cells induce MUC1 expression and polarization on human T cells by an IL-7-dependent mechanism," *J Immunol.*, 174(4):2376-86, 2005.

Vousden et al., "Live or let die: the cell's response to p53," *Nat. Rev. Cancer*, 2:594-604, 2002.

Wahl et al., "The evolution of diverse biological responses to DNA damage: insights from yeast and p53," *Nat. Cell. Biol.*, 3(12):E277-286, 2001.

Wei et al., "Human MUC1 oncoprotein regulates p53-responsive gene transcription in the genotoxic stress resonse," *Cancer Cell.*, 7(2):167-78, 2005.

Wei et al., "Ligand-dependent formation of retinoid receptors, receptor-interacting protein 140 (RIP140), and histone deacetylase complex is mediated by a novel receptor-interacting motif of RIP140," *J. Biol. Chem.*, 276:16107-16112, 2001.

Weiss et al., "p21Waf1/Cip1 as a therapeutic target in breast and other cancers," *Cancer Cell*, 4:425-429, 2003.

Wheeler et al., "Intrabody and intrakine strategies for molecular therapy," *Mol. Ther.*, 8(3):355-366, 2003.

Wider, "Structure determination of biological macromolecules in solution using NMR spectroscopy," *BioTechniques*, 29:1278-1294, 2000.

Wu et al., "Killer/DR5 is a DNA damage-inducible p53-regulated death receptor gene," *Nat. Benet.*, 17:141-143, 1997.

Yamamoto et al., "Interaction of the DF3/MUC1 breast carcinoma-associated antigen and beta-catenin in cell adhesion," *J. Biol. Chem.*, 272:12492-12494, 1997.

Yin et al., "Human MUC1 carcinoma antigen regulates intracellular oxidant levels and the apoptotic response to oxidative stress," *J. Biol. Chem.*, 278:35458-35464, 2003.

Yin et al., "MUC1 oncoprotein activates the FOXO3a transcription factor in a survival response to oxidative stress," *J. Biol. Chem.*, 279:45721-45727, 2004.

Yu et al., "PUMA induces the rapid apoptosis of colorectal cancer cells," *Mol. Cell*, 7:673-682, 2001.

Zhang et al., "Nucleic acid aptamers in human viral disease," *Arch. Immunol. Ther. Exp.*, 52:307-315, 2004.

Zhang et al., "Ets-1 protects vascular smooth muscle cells from undergoing apoptosis by activating p21WAF1/Cip1: ETS-1 regulates basal and and inducible p21WAF1/Cip: ETS-1 regulates basal and inducible p21WAF1/Cip1 transcription via distinct cis-acting elements in the p21WAF/Cip1 promoter," *J. Biol. Chem.*, 278:27903-27909, 2003.

Supplementary European Search Report, issued in European Patent Application No. 06735077, dated Oct. 26, 2009.

Wei et al., "Human MUC1 oncoprotein regulates p53-responsive gene transcription in the genotoxic stress response. Supplemental Data," *Cancer Cell.*, 7(2):167-178, 2005.

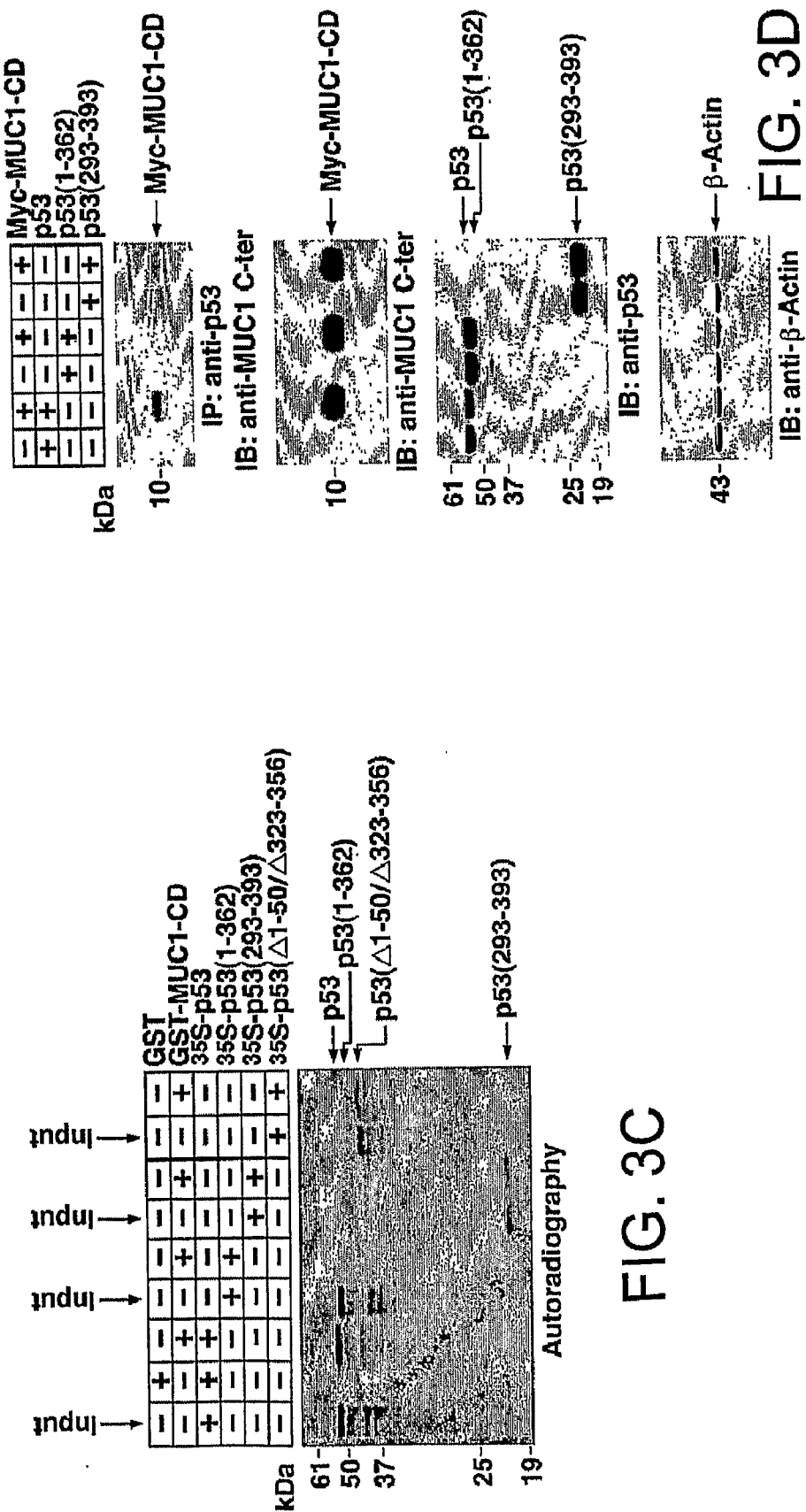

HCT116

ZR-75-1

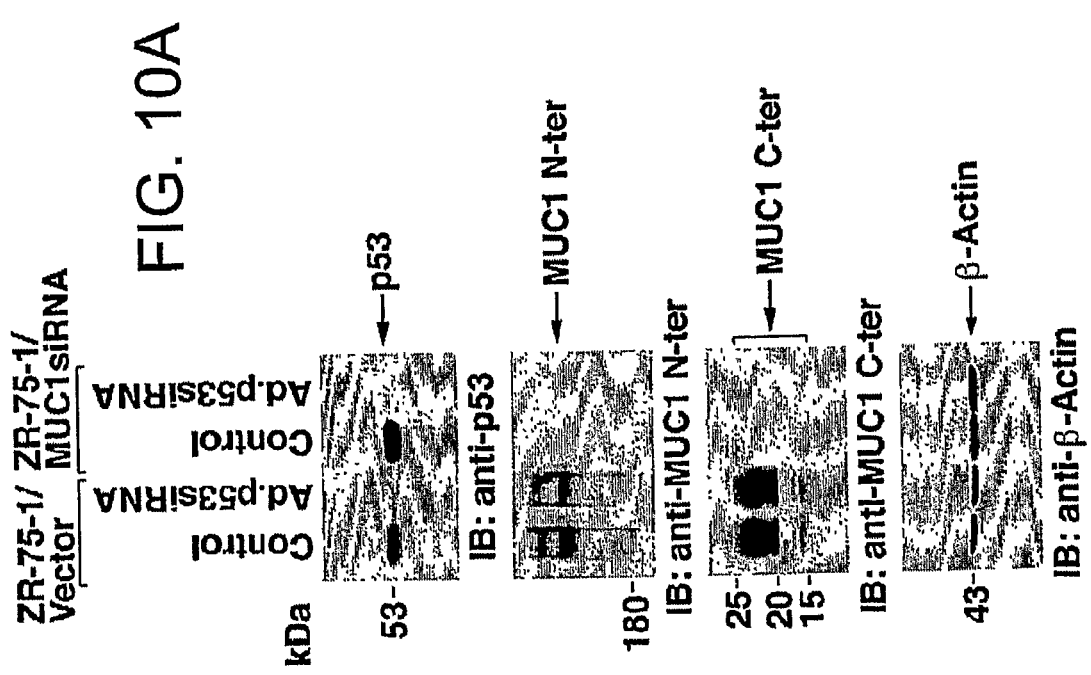
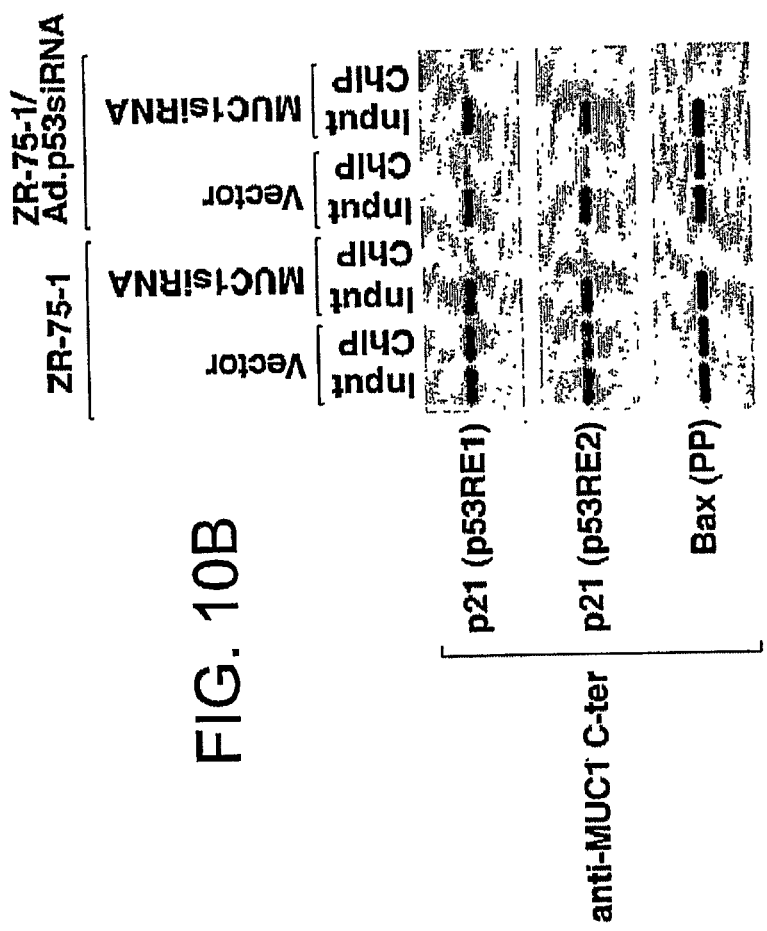

```
  1 mtpgtgslff lllltvltv vtgsghasst pggeketsat qrssmpsste kkvvsmtssv
 61 lsshspgsgs sttggqdvsl apatepasgs aatwgqdvts vpvtrpapgs ttspaqdvts
121 apdtrpalgs tappvhgvts apdtrptlgs tappvhgvts apdtrptlgs tappvhnvts
181 asgsasgsas tlvhngtsar attpaskst pfsipshhsd tpttltshst ktdasstths
241 tvspltssnh stspqlsigv sfflsfhis nlqfnssled pstnyyqelq rdiselilgi
301 ykqgdflgvs nikfrpgsvv vqstlafreg ttnvhdveaq fnqhkteaas rynltisdvs
361 vsdvpfpfsa qsgagvpgwg iallvlcvl valaivylia lavcqcrrkn ygqldifpar
421 dayhpmseyp tyhthgryvp psstnrspye kvsegngges lsytnpavaa tsanl
```

FIG. 11A cqcrrknygqldifpardayhpmseyptyhthgryvppsstnrspyekvsegngges lsytnpavaa
tsanl

FIG. 11B

```
  1 meepqsdpsv epplsqetfs dlwkllpenn vlsplpsqam ddlmlspddi eqwftedpgp
 61 deaprmpeaa ppvapapaap tpaapapaps wplsssvpsq ktyqgsygfr lgflhsgtak
121 svtctyspal nkmfcqlakt cpvqlwvdst pppgtrvram aiykqsqhmt evvrcphhe
181 rcsdsdglap pqhlirvegn lrveylddrn tfrhsvvvpy eppevgsdct tihynymcns
241 scmggmnrrp iltiitleds sgnllgrnsf evhvcacpgr drrteeenlr kkgephhelp
301 pgstkralpn ntssspqpkk kpldgeyftl qirgrerfem frelnealel kdaqagkepg
361 gsrahsshlk skkgqstsrh kklmfktegp dsd
```

MODULATION OF MUC1 ACTIVITY

STATEMENT REGARDING FEDERALLY SPONSORED RESEARCH OR DEVELOPMENT

The research described in this application was supported by grant numbers CA097098 and CA29431 from the National Cancer Institute of the National Institutes of Health and grant number BC022158 from the U.S. Army. Thus, the government has certain rights in the invention.

TECHNICAL FIELD

This invention relates to regulation of cell growth, and more particularly to the regulation of cancer cell growth.

BACKGROUND

The MUC1 protein is overexpressed by greater than 800,000 of the 1.3 million tumors diagnosed in the United States each year. Thus effective therapeutic and/or prophylactic methodologies targeted to MUC1 in cancer or pre-cancerous cells would be of enormous humanitarian, social, and economic value.

Co-pending U.S. application Ser. No. 10/732,212 is incorporated herein by reference in its entirety.

SUMMARY

The inventor has found that MUC1 binds to the p53 tumor suppressor protein and attenuates the tumor-suppressor function of p53 by promoting selection of the p53-mediated growth arrest response, and suppressing the p53-dependent apoptotic response, to DNA damage. MUC1 does this by coactivating, together with p53, p21 gene transcription and inhibiting Bax gene transcription. MUC1 binds to the p53 responsive element (p53RE) of the p21 gene and requires the presence of p53 for the binding. MUC1 does not bind to the p53RE, but does bind to the proximal promoter (PP) of the Bax gene. However, the binding of MUC1 to the Bax gene PP is not dependent on the presence of p53. The invention includes methods for identifying compounds useful for inhibiting the interaction between MUC1 and p53 or the TATA-binding protein (TBP). Such compounds can be useful for directly promoting apoptosis of MUC1-expressing cancer cells, for enhancing the efficacy of genotoxic chemotherapeutic agents against such cancer cells, and as anti-cancer prophylactic agents. Also included in the invention are methods of inhibiting the interaction between p53 (or TBP) and MUC1 in which cells (e.g., carcinoma cells such as breast carcinoma cells) are contacted with compounds that inhibit the interaction between MUC1 and p53 (or TBP). While the experiments described herein were generally performed with human MUC1, MUC1-binders and cells, it is understood that the methods described herein can be performed with corresponding molecules from any of the mammalian species recited below.

More specifically, the invention provides a method of identifying a compound that inhibits binding of MUC1 to p53. The method includes: (a) providing a MUC1 test agent; (b) providing a p53 (or TBP) test agent that binds to the MUC1 test agent; (c) contacting the MUC1 test agent with the p53 (or TBP) test agent in the presence of a test compound; and (d) determining whether the test compound inhibits binding of the MUC1 test agent to the p53 (or TBP) test agent. The contacting can be carried out in a cell-free system or it can occur in a cell.

Also featured by the invention is a method of generating a compound that inhibits the interaction between MUC1 and p53 (or TBP). The method includes: (a) providing the three-dimensional structure of a molecule that includes the cytoplasmic domain of MUC1, the C terminus of p53, or a MUC1-binding fragment of TBP; (b) designing, based on the three dimensional structure, a compound comprising a region that inhibits the interaction between MUC1 and p53 or TBP; and (c) producing the compound. The method can further involve determining whether the compound inhibits the interaction between MUC1 and p53 or TBP.

Another embodiment of the invention is a process of manufacturing a compound. The process includes: (a) performing the method described in the previous paragraph; and b) after determining that the compound inhibits the interaction between MUC1 and p53 or TBP, manufacturing the compound.

In another aspect, the invention provides an in vivo method of inhibiting binding of MUC1 to p53 or TBP in a cancer cell that expresses MUC1. The method includes: (a) identifying a subject as having a cancer that expresses MUC1; and (b) administering to the subject a compound or, where the compound is a polypeptide, a nucleic acid comprising a nucleic acid sequence encoding the polypeptide, the nucleic acid sequence being operably linked to a transcriptional regulatory element (TRE), and the compound inhibiting binding of p53 or TBP to the cytoplasmic domain of MUC1. The compound can be a peptide fragment of (a) MUC1, or (b) p53, or (c) TBP. Thus, the compound can be a peptide fragment of the cytoplasmic domain of MUC1. It can be or it can contain all or a part of: (i) amino acids 9-46 of SEQ ID NO:2; (ii) amino acids 1-51 of SEQ ID NO:2; or (iii) amino acids 363-393 of SEQ ID NO:1. Moreover, the compound can be an antibody, or an antibody fragment, that binds to: (a) the cytoplasmic domain of MUC1; or the C terminus of p53. Alternatively, the compound can be a small molecule e.g., a small molecule that is or contains a nucleic acid aptamer. The subject can be a human subject. The cancer cell can be, for example, a breast cancer, lung cancer, colon cancer, pancreatic cancer, renal cancer, stomach cancer, liver cancer, bone cancer, hematological cancer, neural tissue cancer, melanoma, ovarian cancer, testicular cancer, prostate cancer, cervical cancer, vaginal cancer, or bladder cancer cell. The TRE can be a DF3 enhancer.

Also embraced by the invention is a method of killing a cancer cell. The method can involve, before, after, or at the same time as performing the method described in the previous paragraph, exposing the subject to one or more genotoxic agents. The genotoxic agents can be, for example, one or more forms of ionizing radiation and/or one or more chemotherapeutic agents. The one or more chemotherapeutic agents can be, for example, cisplatin, carboplatin, procarbazine, mechlorethamine, cyclophosphamide, camptothecin, ifosfamide, melphalan, chlorambucil, bisulfan, nitrosurea, dactinomycin, daunorubicin, doxorubicin, bleomycin, plicomycin, mitomycin, etoposide, verampil, podophyllotoxin, tamoxifen, taxol, transplatinum, 5-fluorouracil, vincristin, vinblastin, methotrexate, or an analog of any of the aforementioned.

Another method featured by the invention is an in vivo method of inhibiting expression of MUC1 in a cancer cell that expresses MUC1. The method includes: (a) identifying a subject as having a cancer, the cancer comprising a cancer cell that expresses MUC1; and (b) introducing into the cell a MUC1 small interfering RNA (siRNA). The introducing step can involve administration of the siRNA to the subject and uptake of the siRNA by the cancer cell or administering to the subject, and uptake by the cancer cell of, a nucleic acid: (a)

from which sense and anti-sense strands of the siRNA can be transcribed under the direction of separate TREs; or (b) from which both sense and anti-sense strands of the siRNA can be transcribed under the direction of a single TRE. The subject can be a human patient and the cancer cell can be any of those listed above.

"Polypeptide" and "protein" are used interchangeably and mean any peptide-linked chain of amino acids, regardless of length or post-translational modification. The MUC-1 and MUC1-binder molecules and test agents used in any of the methods of the invention can contain or be wild-type proteins or can be variants that have one or more (e.g., one, two, three, four, five, six, seven, eight, nine, ten, 12, 15, 20, 25, 30, 35, 40, or 50) conservative amino acid substitutions. Conservative substitutions typically include substitutions within the following groups: glycine and alanine; valine, isoleucine, and leucine; aspartic acid and glutamic acid; asparagine, glutamine, serine and threonine; lysine, histidine and arginine; and phenylalanine and tyrosine. All that is required as that: (i) such variants of MUC1 have at least 25% (e.g., at least: 30%; 40%; 50%; 60%; 70%; 75%; 80%; 85%; 90%; 95%; 97%; 98%; 99%; 99.5%, or 100% or even greater) of the ability of wild-type MUC1 C-ter to bind to p53 or TBP; and (ii) such variants of a MUC1-binder have at least 25% (e.g., at least: 30%; 40%; 50%; 60%; 70%; 75%; 80%; 85%; 90%; 95%; 97%; 98%; 99%; 99.5%, or 100% or even greater) of the ability of the relevant wild-type MUC1-binder to bind to MUC1 C-ter.

As used herein, a "MUC1-binder" is p53 or TBP.

As used herein, a "MUC1-binder test agent" contains, or is, (a) the full-length, wild-type MUC1-binder, (b) a part of the MUC1-binder that is shorter than the full-length MUC1-binder, or (c) (a) or (b) but with one or more (see above) conservative substitutions. "Parts of a MUC1-binder" include fragments as well deletion variants (terminal as well internal deletions) of the MUC1-binder. Deletion variants can lack one, two, three, four, five, six, seven, eight, nine, ten, 11, 12, 13, 14, 15, 16, 17, 18, 19, or 20 amino acid segments (of two or more amino acids) or non-contiguous single amino acids. MUC1-binder test agents can include internal or terminal (C or N) irrelevant amino acid sequences (e.g., sequences derived from other proteins or synthetic sequences not corresponding to any naturally occurring protein). These added irrelevant sequences will generally be about 1-50 (e.g., two, four, eight, ten, 15, 20, 25, 30, 35, 40, or 45) amino acids in length. MUC1-binder test agents other than full-length wild-type MUC1-binder molecules will have at least 50% (e.g., at least 50%, at least 60%, at least 70%, at least 80%, at least 90%, at least 95%, at least 98%, at least 99%, at least 99.5%, or 100% or more) of the ability of the full-length wild-type MUC1-binder to bind to the cytoplasmic domain of MUC1.

As used herein, a "MUC1 test agent" contains, or is, (a) full-length, wild-type mature MUC1, (b) a part of MUC1 that is shorter than full-length, wild-type, mature MUC1, or (c) (a) or (b) but with one or more (see above) conservative substitutions. "Parts of a MUC1" include fragments (e.g., MUC1 C-ter or the cytoplasmic domain (CD) of MUC1) as well deletion variants (terminal as well internal deletions) of MUC1. Deletion variants can lack one, two, three, four, five, six, seven, eight, nine, ten, 11, 12, 13, 14, 15, 16, 17, 18, 19, or 20 amino acid segments (of two or more amino acids) or non-contiguous single amino acids. MUC1 test agents can include internal or terminal (C or N) irrelevant amino acid sequences (e.g., sequences derived from other proteins or synthetic sequences not corresponding to any naturally occurring protein). These added irrelevant sequences will generally be about 1-50 (e.g., two, four, eight, ten, 15, 20, 25, 30, 35, 40, or 45) amino acids in length. MUC1 test agents other than full-length, wild-type, mature MUC1 will have at least 50% (e.g., at least 50%, at least 60%, at least 70%, at least 80%, at least 90%, at least 95%, at least 98%, at least 99%, at least 99.5%, or 100% or more) of the ability of the full-length, wild-type, mature MUC1-binder to bind to p53 or TBP.

As used herein, "operably linked" means incorporated into a genetic construct so that expression control sequences effectively control expression of a coding sequence of interest.

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can also be used in the practice or testing of the present invention. All publications, patent applications, patents and other references mentioned herein are incorporated by reference in their entirety. The materials, methods, and examples disclosed herein are illustrative only and not intended to be limiting.

Other features and advantages of the invention, e.g., inhibiting survival of cancer cells, will be apparent from the following description, from the drawings and from the claims.

Left panel: Lysates from HCT116 cells human colon carcinoma cells stably transfected with an expression vector containing cDNA encoding full-length mature human MUC1 ("HCT116/MUC1" cells) and HCT116 cells stably transfected with a control "empty" expression vector ("HCT116/vector" cells) were immunoprecipitated with anti-p53 antibody ("IP: anti-p53"). These immunoprecipitates, and control unprecipitated lysate from HCT116/MUC1 cells ("HCT116/MUC1 WCL"), were subjected to immunoblot ("IB") analysis with anti-MUC1 C-ter antibody, anti-MUC1 N-ter antibody, and anti-p53 antibody. The positions of molecular weight markers ("kDa") are indicated on the left and of MUC1 C-ter, MUC1 N-ter, and p53 are indicated on the right of the blots.

Right panel: A lysate from ZR-75-1 human breast cancer cells was immunoprecipitated ("IP") with anti-p53 antibody ("Anti-p53") or control IgG ("IgG"). These immunoprecipitates, and control unprecipitated lysate from ZR-75-1 cells ("ZR-75-1 WCL"), were subjected to immunoblot ("IB") analysis with anti-MUC1 C-ter antibody, anti-MUC1 N-ter antibody, and anti-p53 antibody. The positions of molecular weight markers ("kDa") are indicated on the left and of MUC1 C-ter, MUC1 N-ter, and p53 are indicated on the right of the blots.

Figure 1A:
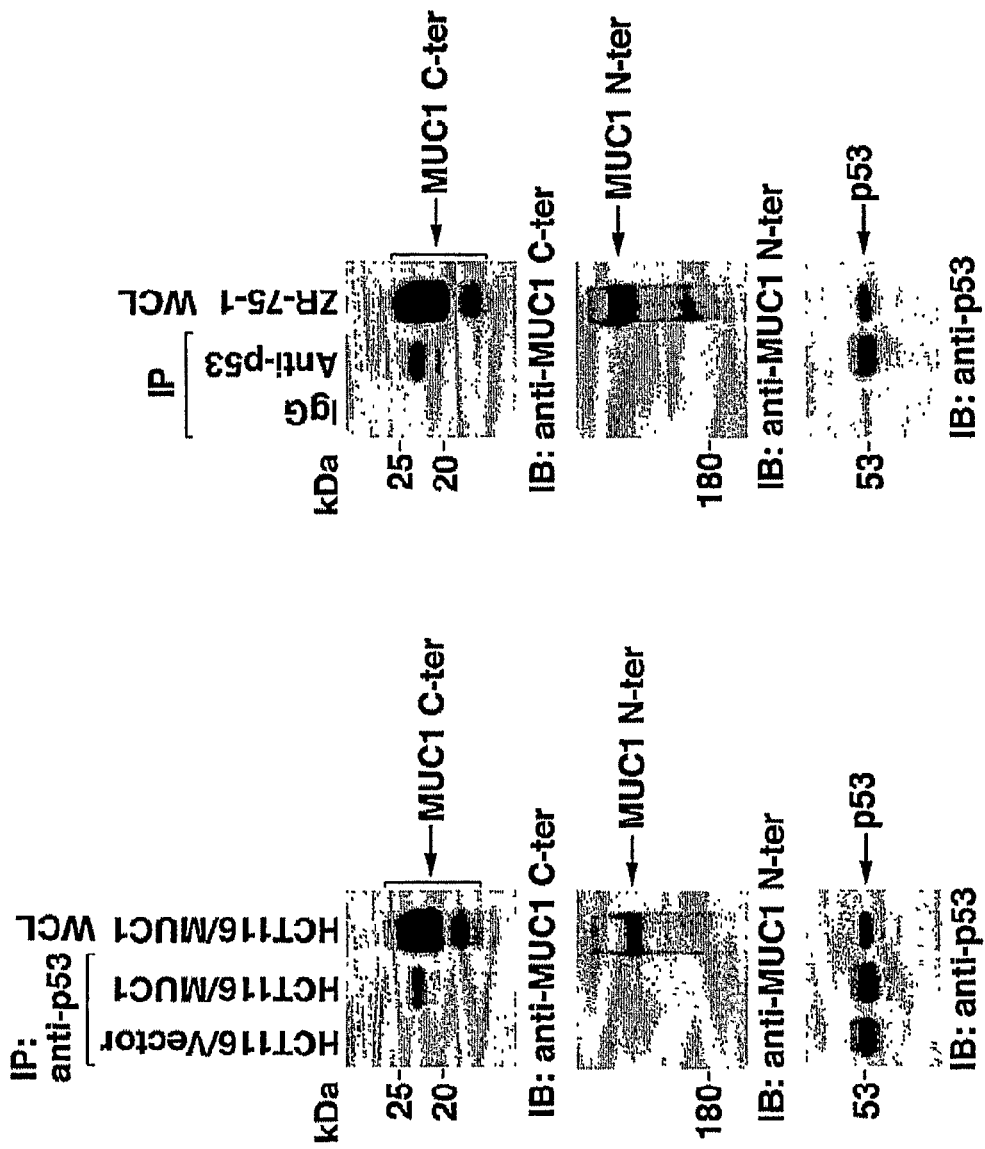
FIG. 1A is a pair of photographs of immunoblots.
Figure 1B:
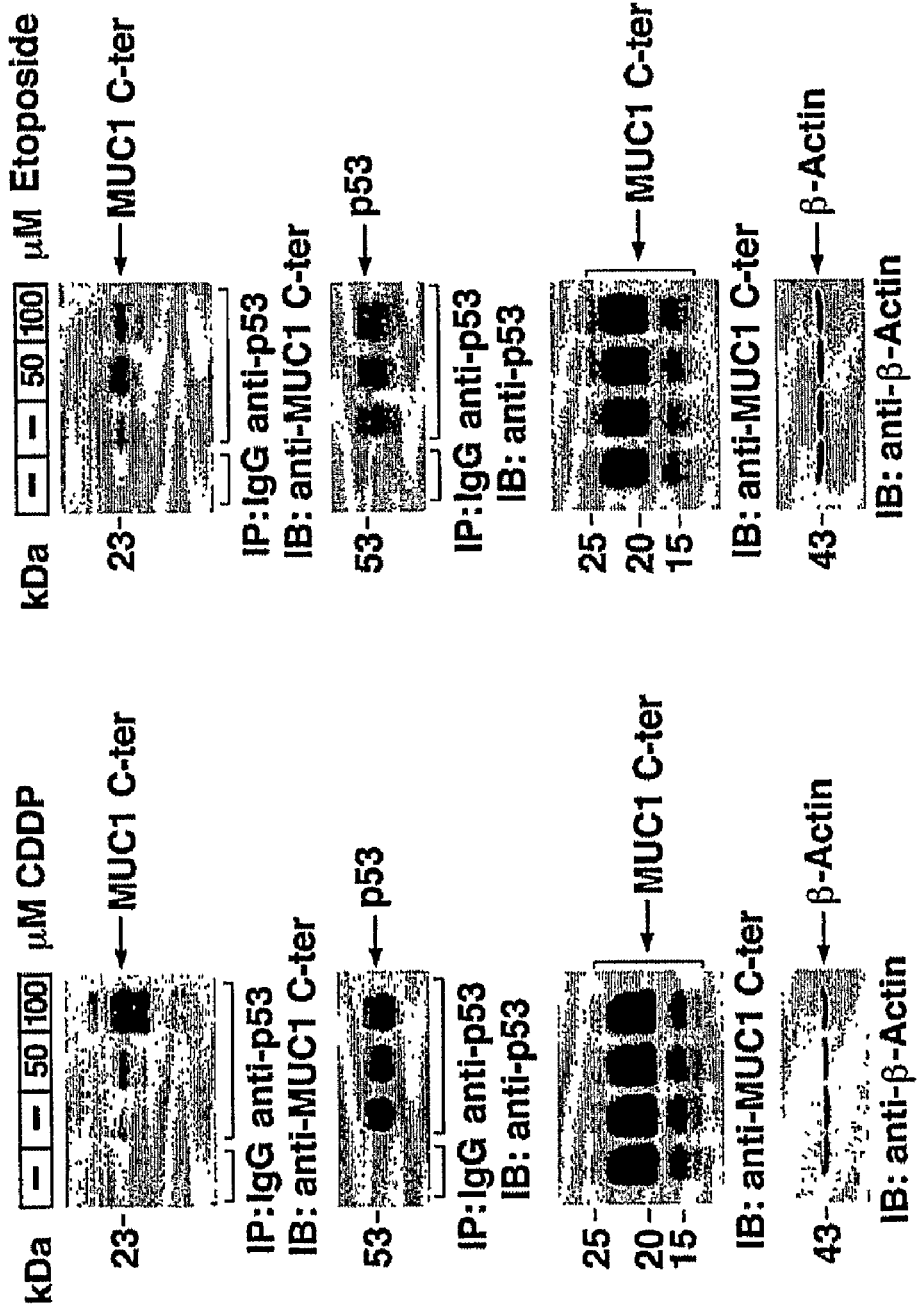

FIGS. 1B and C are photographs of immunoblots. HCT116/MUC1 cells (FIG. 1B) or ZR-75-1 cells (FIG. 1C) for 24 h were either untreated (first and second lanes of each blot) or treated with 50 µM or 100 µM cisplatin ("CDDP"; left panel) or etoposide ("Etoposide"; right panel) and lysates were prepared from all samples. The lysate from untreated cells was immunoprecipitated ("IP") with control IgG (left lane of each blot) and lysates from all cells were immunoprecipitated with anti-p53 antibody ("IgG anti-p53"; right three lanes of each blot) and the resulting immunoprecipitates (upper two blots) and unprecipitated lysates (lower two blots) were subjected to immunoblot ("IB") analysis with anti-MUC1 C-ter antibody, anti-p53 antibody, and anti-β-Actin antibody. The positions of molecular weight markers ("kDa") are indicated on the left and of MUC1 C-ter, p53 and β-Actin are indicated on the right of the blots.

Figure 2A:
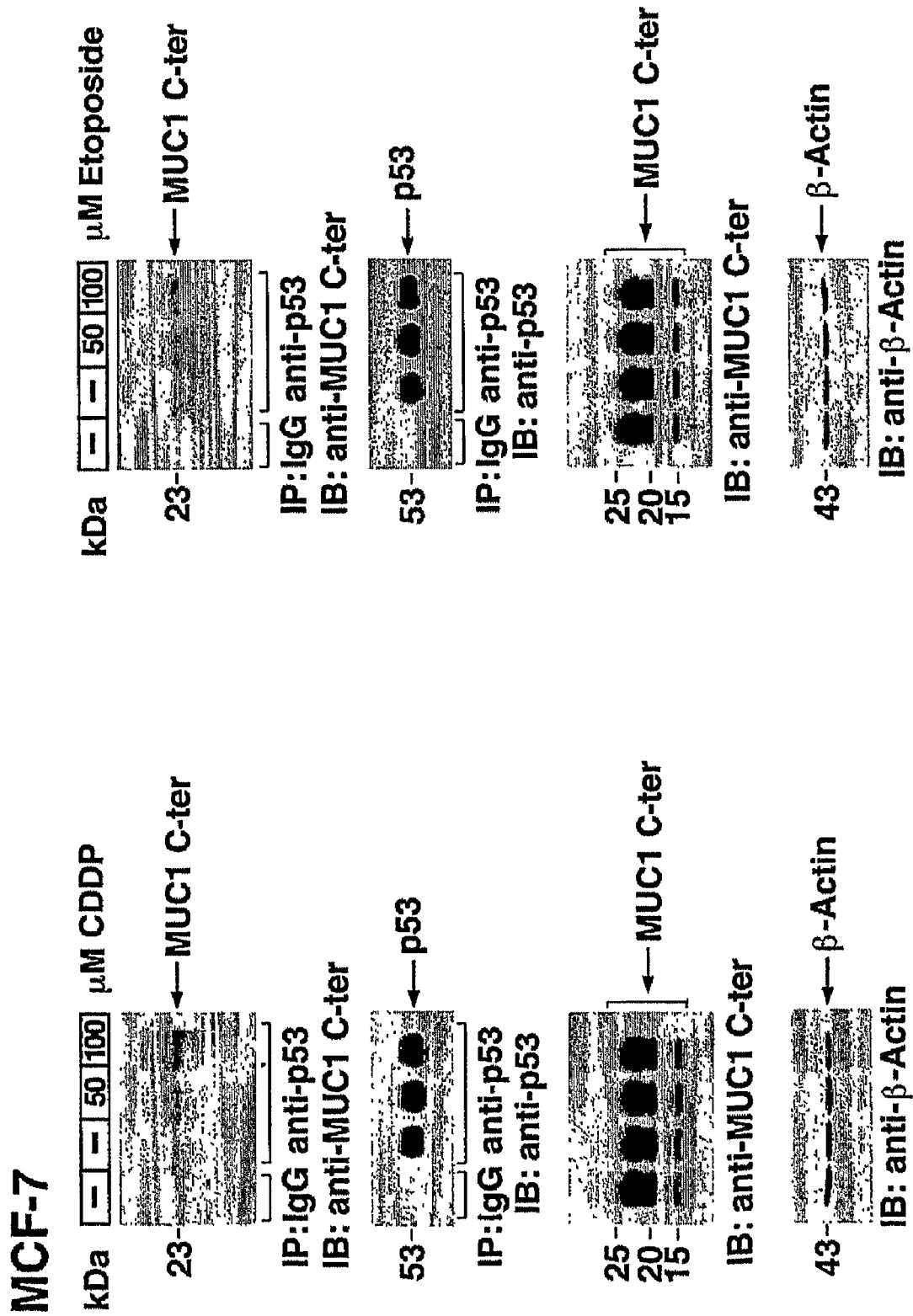

FIGS. 2A and B are photographs of immunoblots. MCF-7 human breast cancer cells (FIG. 2A) or LNCaP human prostate cancer cells (FIG. 2B) for 24 h were either untreated (first and second lanes of each blot) or treated with 50 μM or 100 μM cisplatin ("CDDP"; left panel) or etoposide ("Etoposide"; right panel) and lysates were prepared from all samples. The lysate from untreated cells was immunoprecipitated ("IP") with control IgG (left lane of each blot and the lysates from all cells were immunoprecipitated with anti-p53 antibody ("IgG anti-p53"; right three lanes of each blot) and the resulting immunoprecipitates (upper two blots) and unprecipitated lysates (lower two blots) were subjected to immunoblot ("IB") analysis with anti-MUC1 C-ter antibody, anti-p53 antibody, and anti-β-Actin antibody. The positions of molecular weight markers ("kDa") are indicated on the left and of MUC1 C-ter, p53 and β-Actin are indicated on the right of the blots.

Figure 3A:
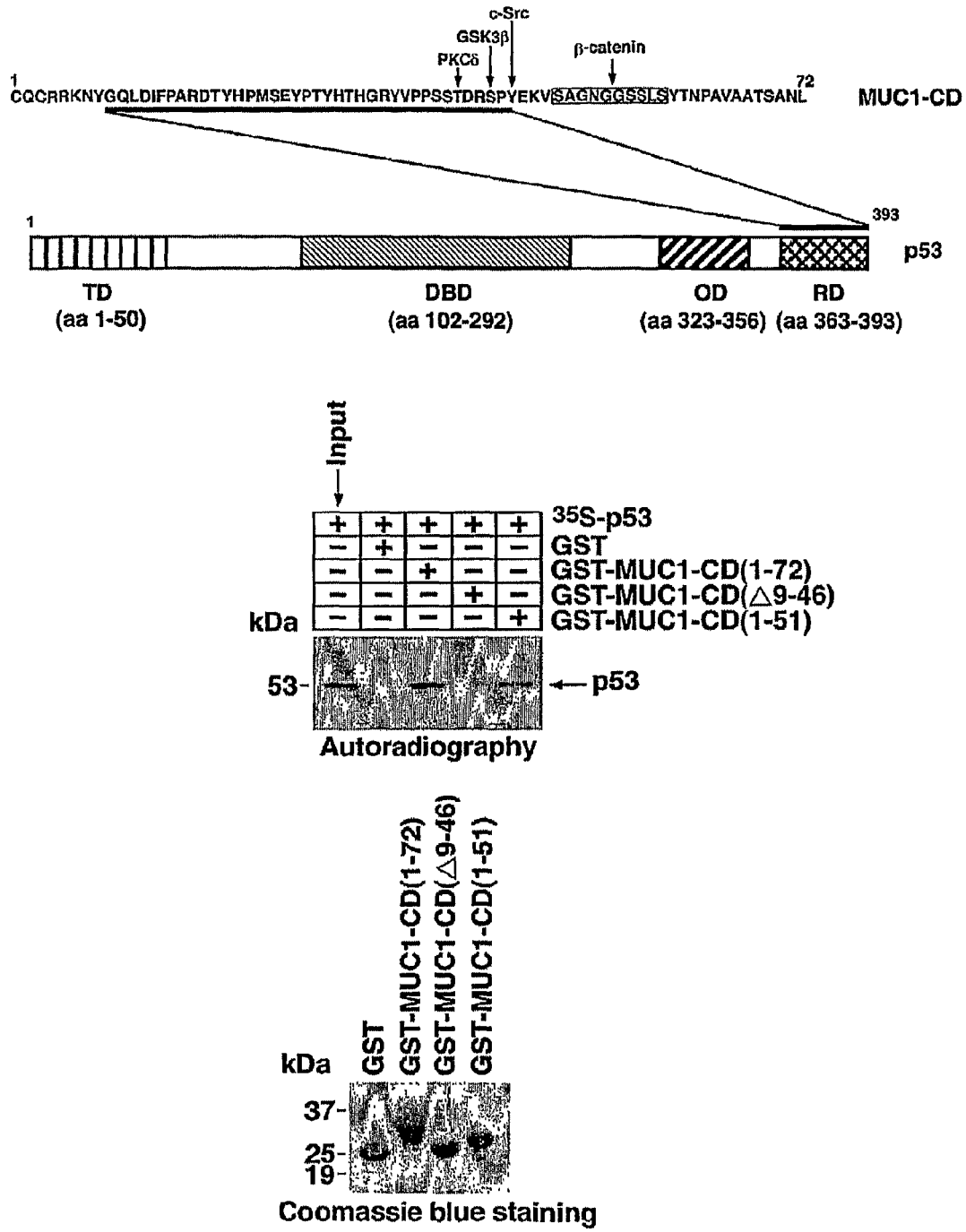

FIG. 3A (top panel) is a depiction of the amino acid sequence (SEQ ID NO:2) of the 72 amino acids constituting the cytoplasmic domain of human MUC1 ("MUC1-CD") and a diagrammatic representation of human p53 (SEQ ID NO:1). Regions on MUC1 and p53 involved in binding to each other are underlined and overlined, respectively, sites at which MUC1-CD is phosphorylated by PKCδ, GSK3β, and c-SRC are indicated by arrows, and a sequence of amino acids on MUC1-CD involved in binding to β-catenin is boxed and indicated by an arrow. In the diagram of p53, "TD" (amino acids 1-50) indicates the transactivation domain, "DBD" (amino acids 102-292) indicates the DNA-binding domain, "OD" (amino acids 323-356) indicates the oligomerization domain, and "RD" (amino acids 363-393) indicates the regulatory domain. FIG. 3A (middle panel) is: a table indicating the components ("+") of five reaction mixtures containing $^{35}$S-labeled p53 ("53S-p53") and, bound to glutathione agarose, glutathione S transferase ("GST"), MUC1-CD fused to GST ("GST-MUC1-CD(1-72)"), or one of two deletion variants of MUC1-CD fused to GST ("GST-MUC1-CD(Δ9-46)" or "GST-MUC1-CD(1-51)"); and an autoradiogram of a SDS-PAGE (sodium dodecyl sulfate electrophoresis gel) gel of adsorbates from the five reaction mixtures. FIG. 3A (bottom panel) is a photograph of a Coomassie blue-stained SDS-PAGE gel of the right four reaction mixtures in the table. The positions of molecular weight markers ("kDa") are indicated on the left of the autoradiogram and the Coomassie blue-stained gel and the position of p53 is indicated on the right of the autoradiogram.

Figure 3B:
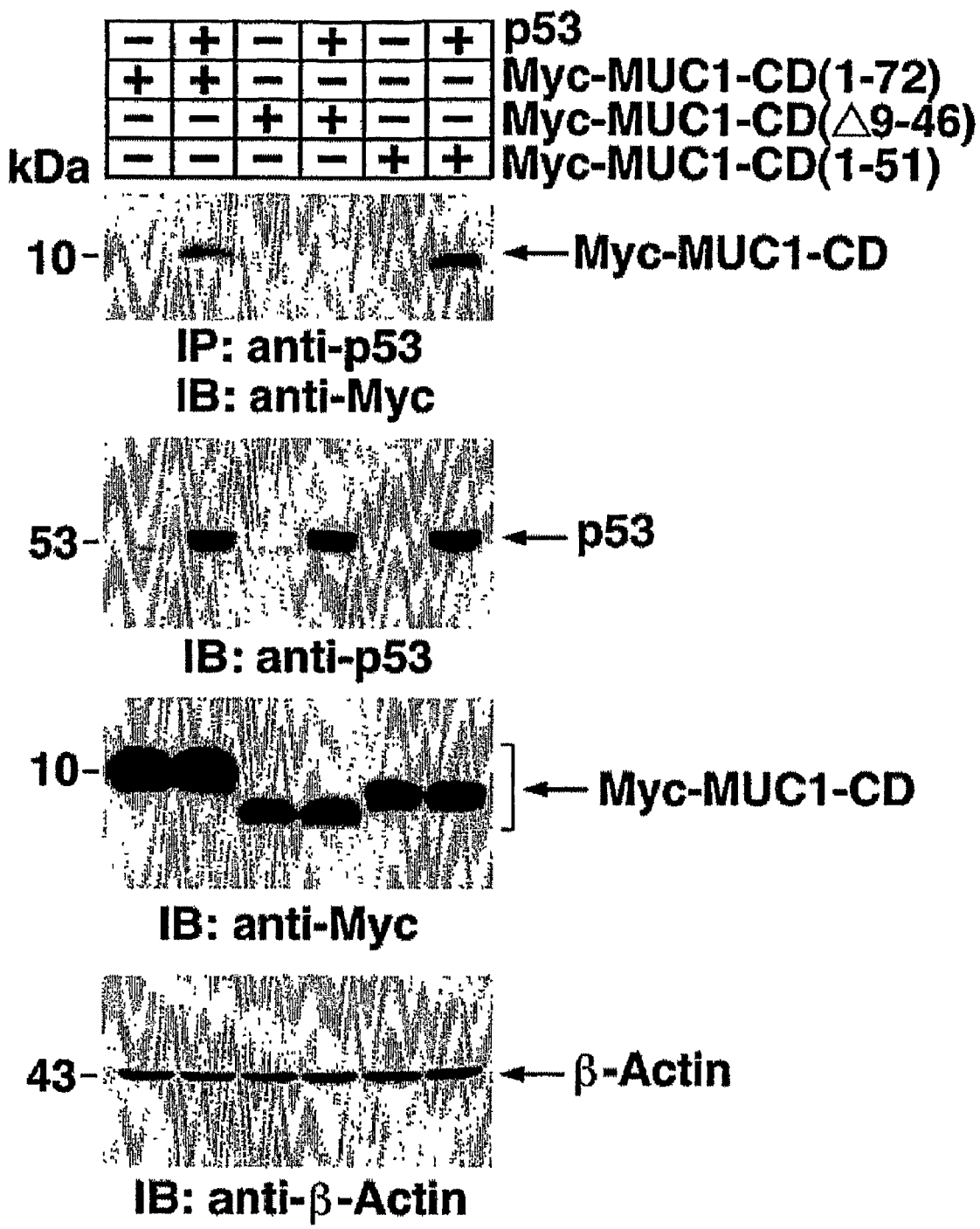

FIG. 3B (top panel) is a table showing five transfectants resulting from transfection of U2OS human osteosarcoma cells with one or two expression vectors. The cells were transiently transfected with 2 μg of an expression vector encoding p53 and/or 1 μg of expression vectors encoding fusion proteins between Myc and MUC1-CD or deletion variants of MUC1-CD (i.e., Myc-MUC1-CD(1-72), Myc-MUC1-CD(Δ9-46), or Myc-MUC1-CD(1-51)). FIG. 3B (panels 2-4 and the bottom panel) are photographs of immunoblots. Lysates from the transfectants were immunoprecipitated ("IP") with anti-p53 antibody and the resulting precipitates were subjected to immunoblot analysis ("IB") with anti-Myc antibody (FIG. 3B, second panel). Unprecipitated lysates were also subjected to immunoblot analysis with anti-p53 antibody (third panel), anti-Myc antibody (fourth panel), or anti-β-Actin antibody (bottom panel). The positions of molecular weight markers ("kDa") are indicated on the left and of p53, Myc-MUC1-CD, and β-Actin are indicated on the right of the blots.

FIG. 3C is: a table indicating the components ("+") of nine reaction mixtures containing $^{35}$S-labeled p53 ("$^{53}$S-p53") or one of three $^{35}$S-labeled deletion variants of p53 ("$^{35}$S-p53 (1-362)", "$^{35}$S-p53(293-393)", or "$^{35}$S-p53(Δ1-50/Δ32-356)") and, bound to glutathione agarose, GST or MUC1-CD fused to GST ("GST-MUC1-CD"); and an autoradiogram of a SDS-PAGE gel of adsorbates from the five reaction mixtures. The positions of molecular weight markers ("kDa") are indicated on the left of the autoradiogram and of p53, p53(1-362), p53(293-393), and p53(Δ1-50/Δ32-356) are indicated on the right of the autoradiogram.

FIG. 3D (top panel) is a table showing five transfectants resulting from transfection of U2OS cells with one or two expression vectors. The cells were transiently transfected with 1 μg of an expression vectors encoding a fusion protein between Myc and MUC1-CD ("Myc-MUC1-CD") and/or 2 μg of an expression vector encoding p53 or two deletion variants of p53 ("p53(1-362)" or p53(293-393). FIG. 3D (panels 2-4 and the bottom panel) are photographs of immunoblots. Lysates from the transfectants were immunoprecipitated ("IP") with anti-p53 antibody and the resulting precipitates were subjected to immunoblot analysis ("IB") with anti-MUC1 C-ter antibody (FIG. 3D, second panel). Unprecipitated lysates were also subjected to immunoblot analysis with anti-MUC1 C-ter antibody (third panel), anti-p53 antibody (fourth panel), or anti-β-Actin antibody (bottom panel). The positions of molecular weight markers ("kDa") are indicated on the left and of p53, p53(1-362), p53(293-393), Myc-MUC1-CD, and β-Actin are indicated on the right of the blots.

Figure 4A:
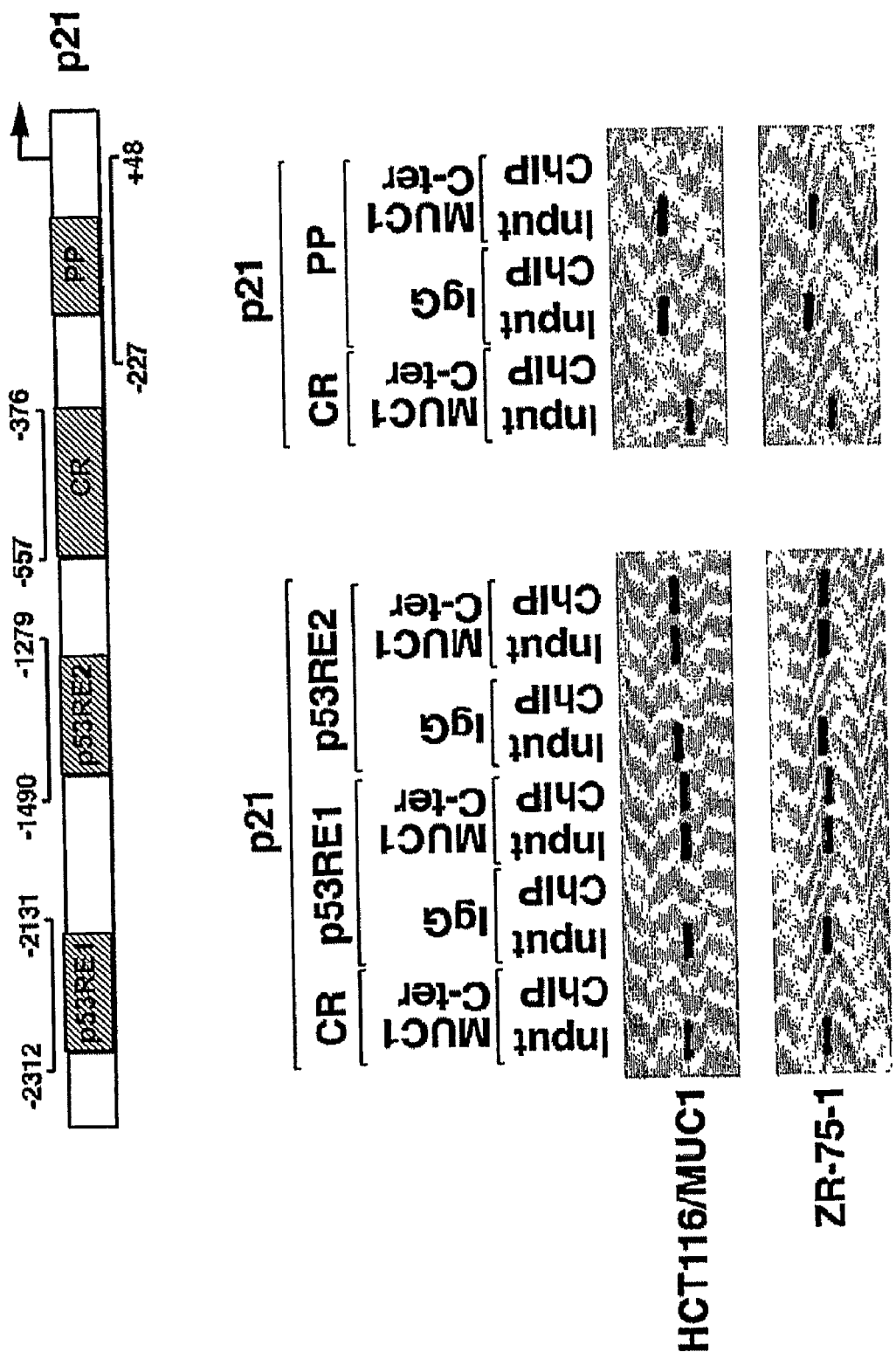

FIG. 4A (top panel) is a schematic depiction of the promoter region of the human p21 gene. The locations (in nucleotide number relative to the transcription initiation site) of two p53-response elements (p53RE1 and p53RE2), a control region ("CR"), and the proximal promoter ("PP") are indicated. The TATA box is located at nucleotides −46 to −43.

FIG. 4A (lower panel) is a series of photographs of ethidium bromide-stained agarose electrophoretic gels of PCR reactions of chromatin immunoprecipitations (ChIP). Soluble chromatin from HCT116/MUC1 cells (top gels) or ZE-75-1 cells (bottom gels) was immunoprecipitated with anti-MUC1 C-ter antibody ("MUC1-C-ter") or a control IgG ("IgG"). DNA was extracted from the resulting immunoprecipitates and the final DNA extractions ("ChIP") or unprecipitated whole chromatin ("Input") were amplified in polymerase chain reactions (PCR) using primers that cover p53RE1, p53RE2, the control region ("CR"), and the proximal promoter ("PP") of the p21 gene. All the PCR reactions were analyzed by ethidium bromide staining of gel electrophoretograms.

Figure 4B:
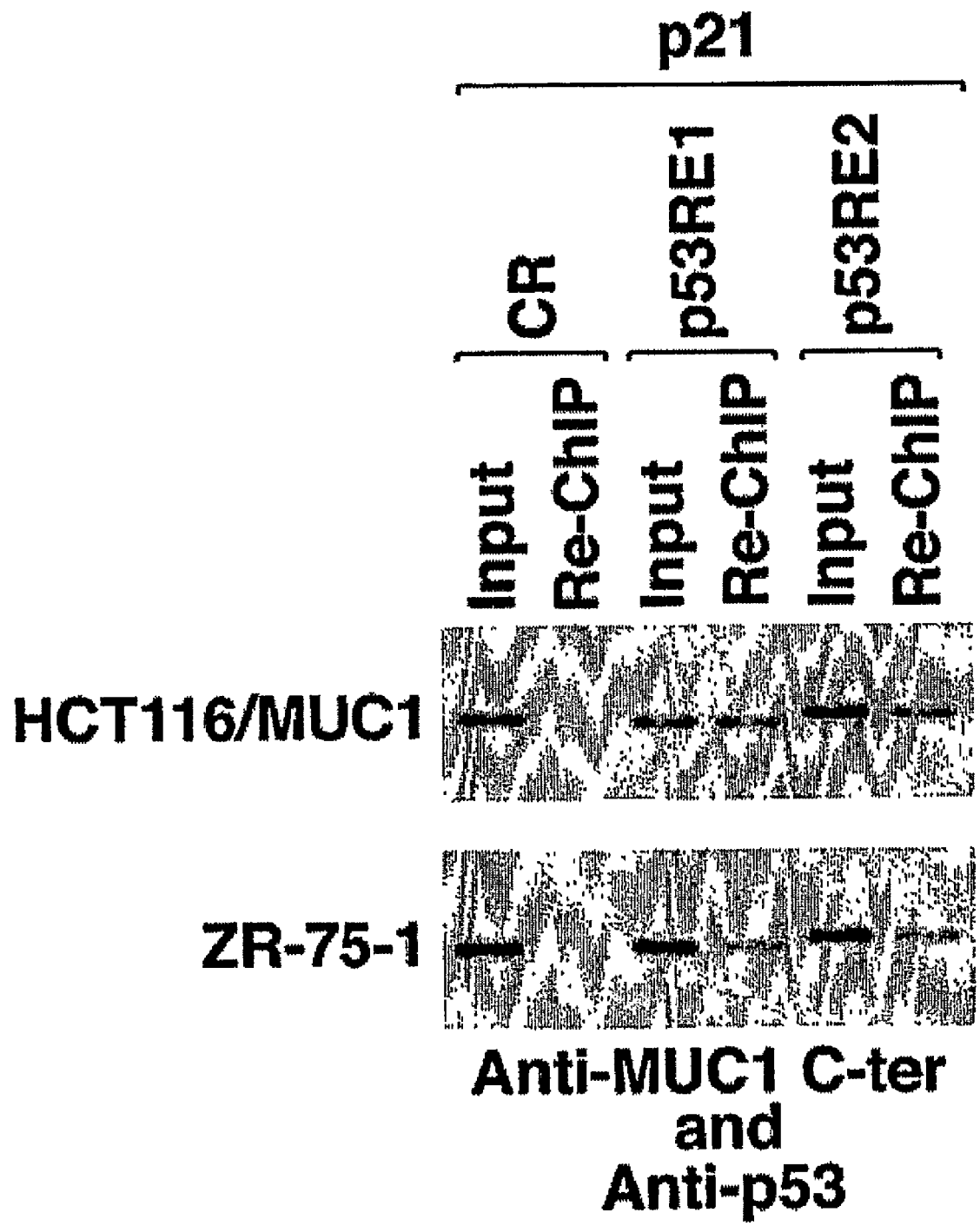

FIG. 4B is a pair of photographs of ethidium bromide-stained agarose electrophoretic gels of PCR reactions of repeated chromatin immunoprecipitations (re-ChIP). Soluble chromatin from HCT116/MUC1 cells (top gel) or ZE-75-1 cells (bottom gel) was immunoprecipitated with anti-MUC1 C-ter antibody ("MUC1 C-ter"). The resulting precipitates were eluted with dithiothreitol (DTT) and the eluates were diluted with Re-Chip buffer and reimmunoprecipitated with anti-p53 antibody. The resulting ReChIP precipitates were analyzed by PCR (as described for FIG. 4A, lower panel) for the presence of the various p21 gene promoter region sequences.

Figure 4C:
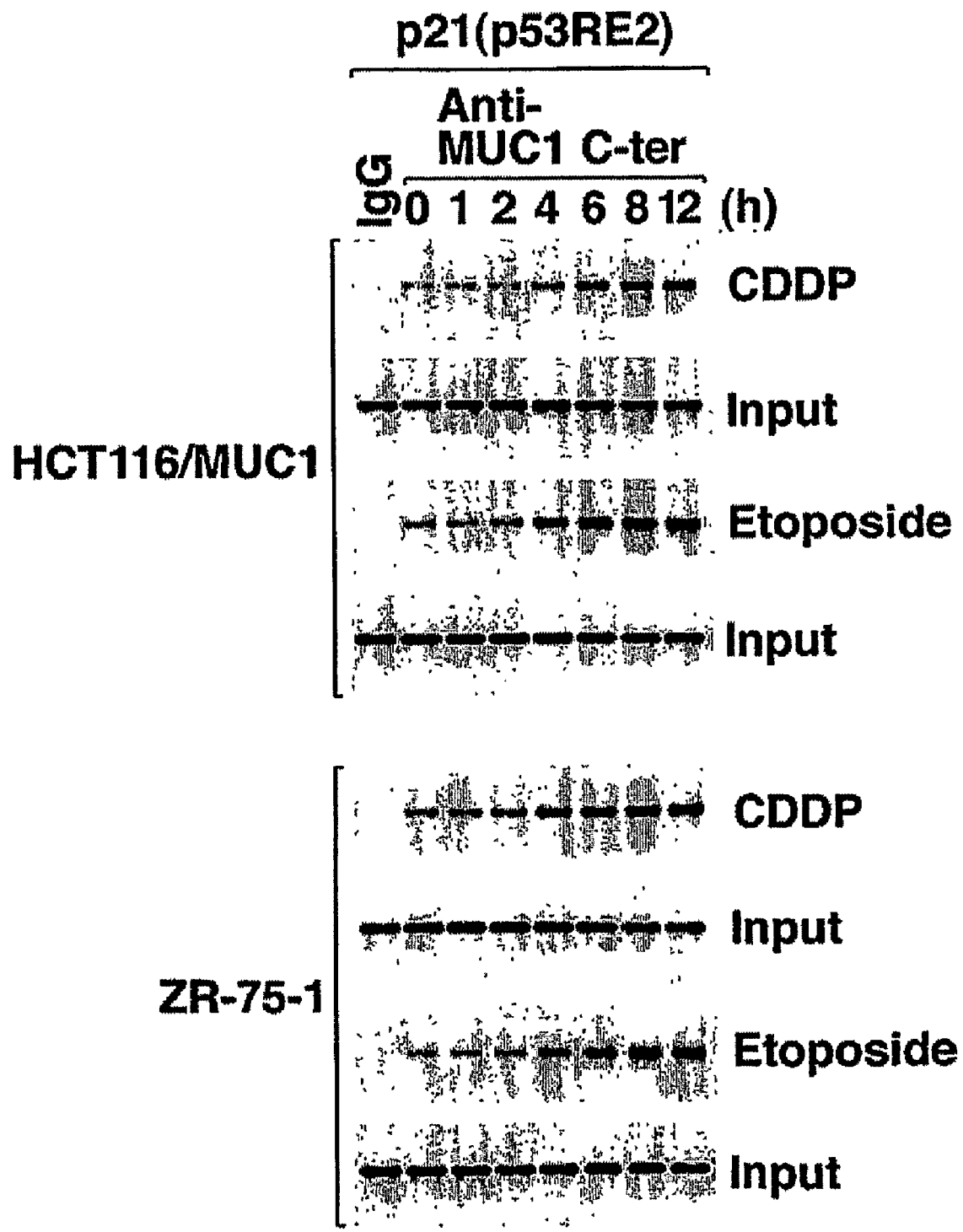

FIG. 4C is a series of photographs of ethidium bromide-stained electrophoretic gels of PCR reactions of chromatin immunoprecipitations (ChIP). HCT116/MUC1 cells (top four gels) or ZR-75-1 cells were treated with 50 µM CDDP (cisplatin) or etoposide ("Etoposide") for the indicated periods of time. Soluble chromatin extracted from all cell samples was immunoprecipitated with anti-MUC1 C-ter antibody and the resulting precipitates and whole unprecipitated soluble chromatin ("Input") were analyzed by PCR for the presence of the p21 gene p53RE2 as described for FIG. 4A, lower panel.

Figure 4D:
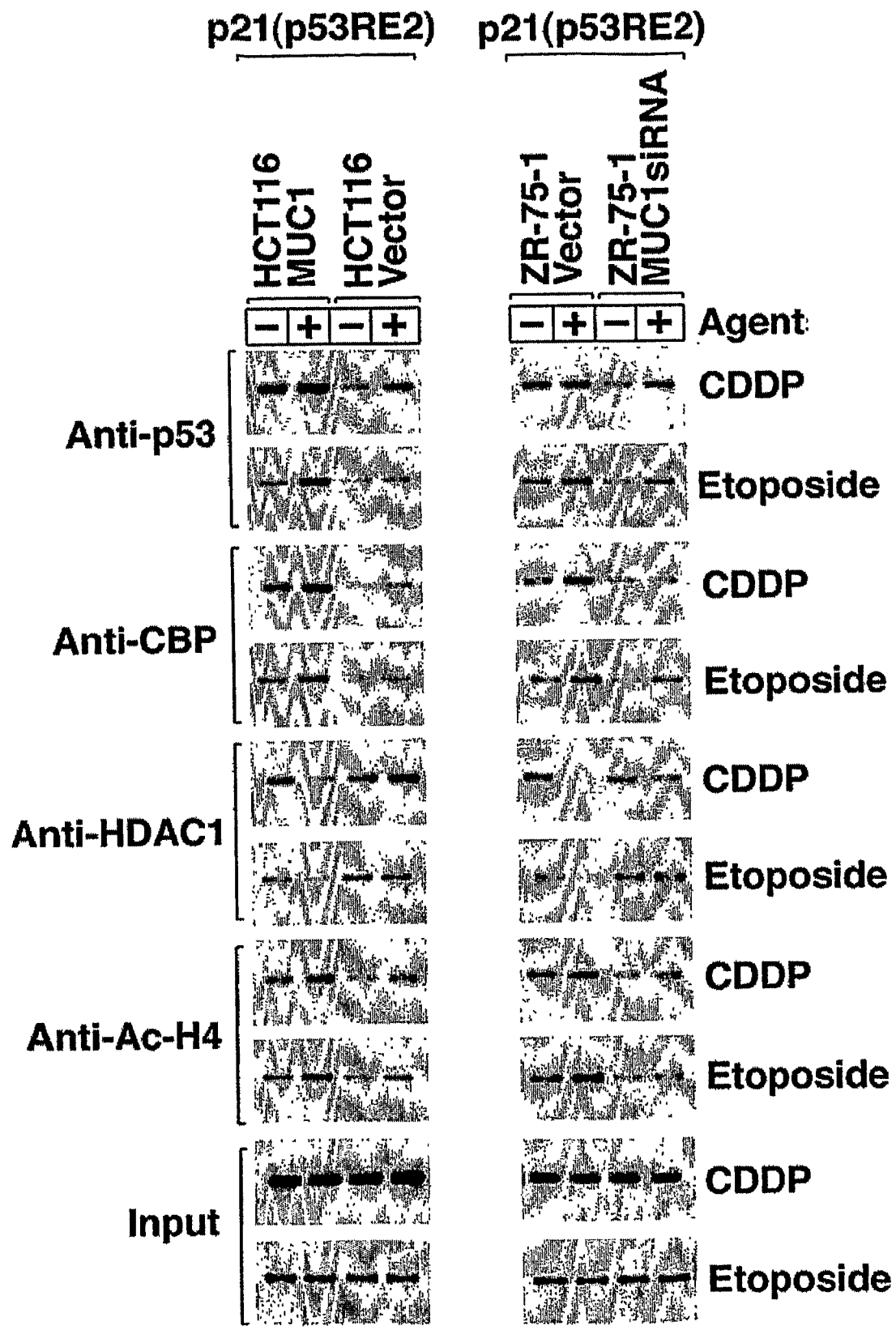

FIG. 4D is a series of photographs of ethidium bromide-stained electrophoretic gels of PCR reactions of chromatin immunoprecipitations (ChIP). HCT116/MUC1 cells and HCT116/vector cells (left panel) or ZR-75-1 cells and ZR-75-1/MUC1siRNA (right panel) were left untreated ("−") or were treated ("+") with 50 µM CDDP (cisplatin) or etoposide ("Etoposide") for 8 h. Soluble chromatin extracted from all cell samples was immunoprecipitated with anti-p53 antibody, anti-CBP antibody, anti-HDAC1 antibody, anti-Ac-H4 antibody and the resulting precipitates and whole unprecipitated soluble chromatin ("Input") were analyzed by PCR for the presence of the p21 gene p53RE2 as described for FIG. 4A, lower panel.

Figure 5A:
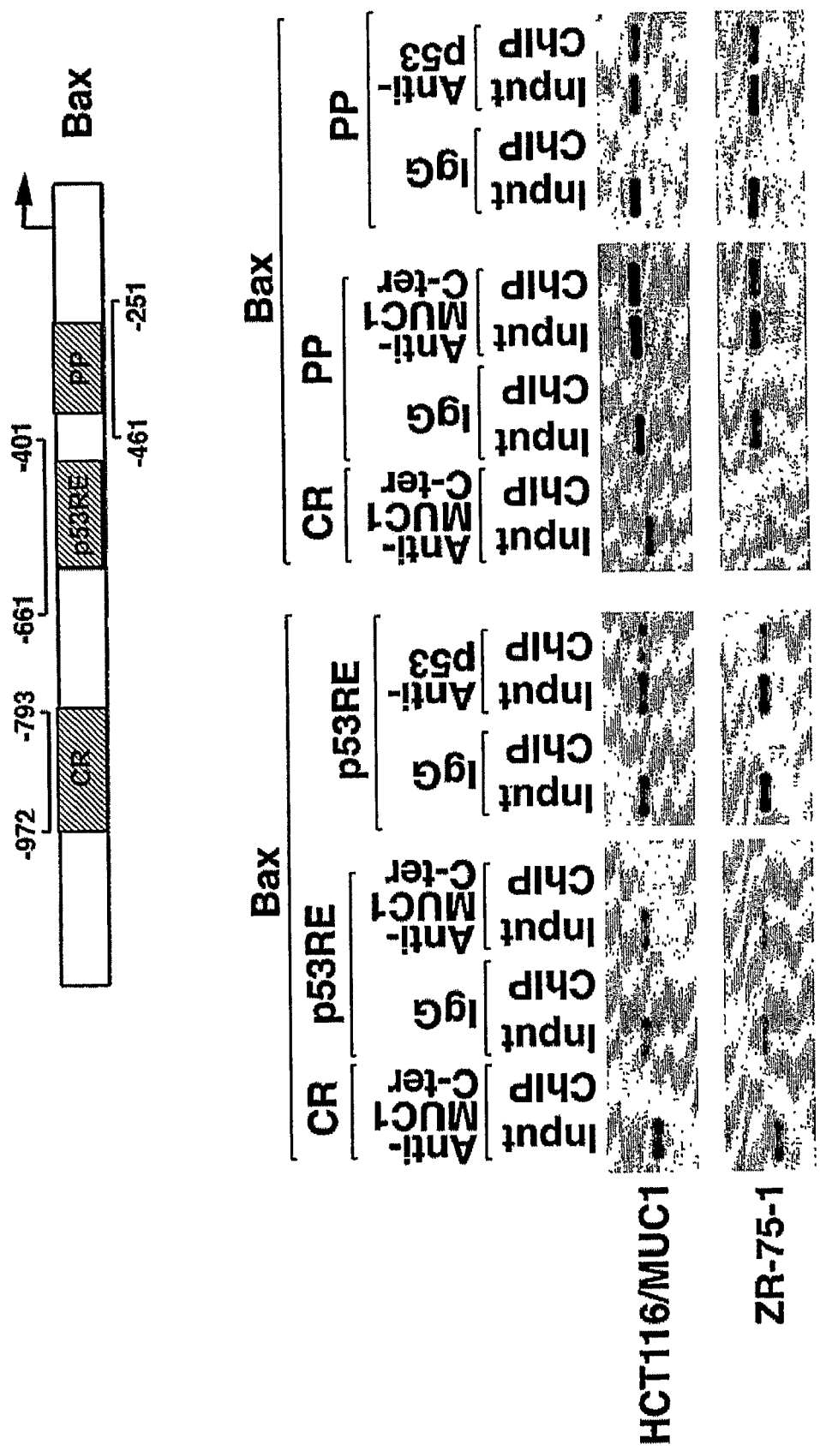

FIG. 5A (top panel) is a schematic depiction of the promoter region of the human Bax gene. The locations (in nucleotide number relative to the transcription initiation site) of a p53-response element (p53RE), a control region ("CR"), and the proximal promoter ("PP") are indicated. The TATA box is located at nucleotides −398 to −395.

FIG. 5A (lower panel) is a series of photographs of ethidium bromide-stained agarose electrophoretic gels of PCR reactions of chromatin immunoprecipitations (ChIP). Soluble chromatin from HCT116/MUC1 cells (top gels) or ZE-75-1 cells (bottom gels) was immunoprecipitated with anti-MUC1 C-ter antibody ("MUC1 C-ter") or a control IgG ("IgG"). DNA was extracted from the resulting immunoprecipitates and the final DNA extractions ("ChIP") and unprecipitated whole chromatin ("Input") were amplified in polymerase chain reactions (PCR) using primers that cover the p53RE (right four gels), the control region ("CR") (left and right four gels), and the proximal promoter ("PP") of the Bax gene (right four gels). All the PCR reactions were analyzed by ethidium bromide staining of gel electrophoretograms.

Figure 5B:
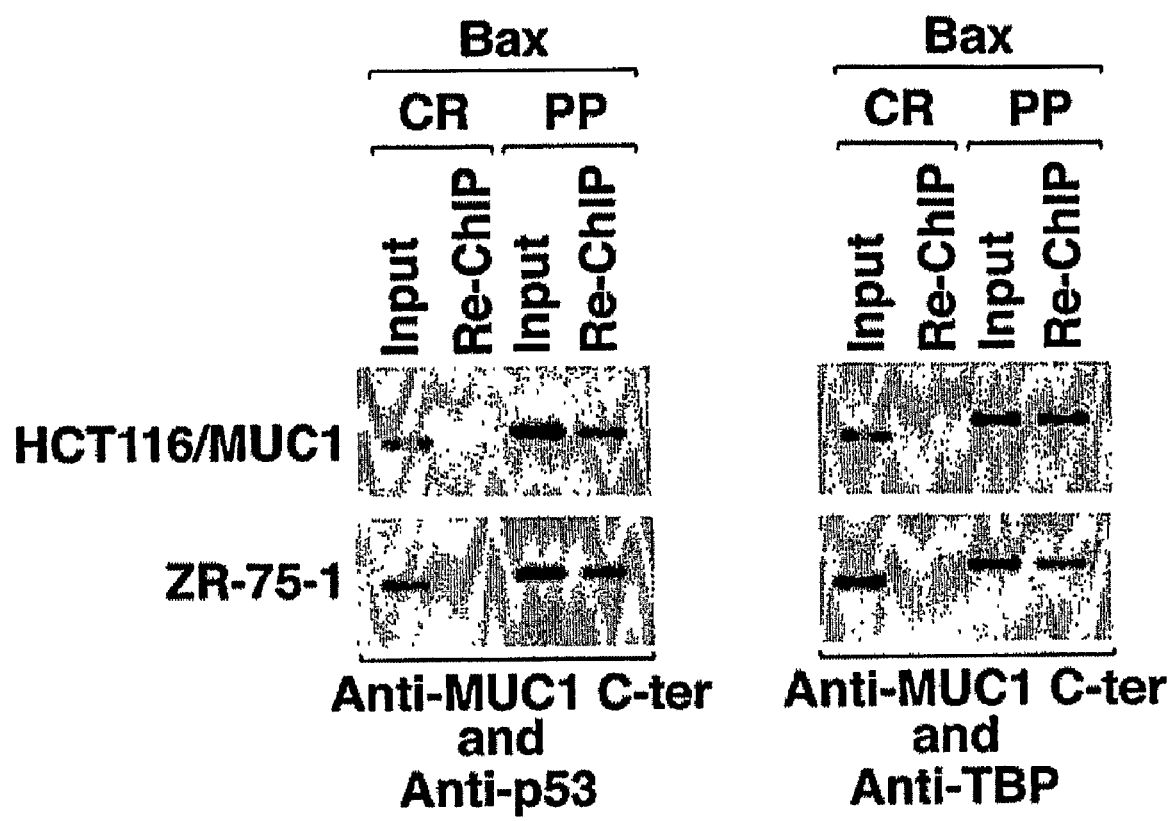

FIG. 5B is a series of photographs of ethidium bromide-stained agarose electrophoretic gels of PCR reactions of repeated chromatin immunoprecipitations (re-ChIP). Soluble chromatin from HCT116/MUC1 cells (top gels) or ZE-75-1 cells (bottom gels) was immunoprecipitated with anti-MUC1 C-ter antibody ("MUC1 C-ter"). The resulting precipitates were eluted with dithiothreitol (DTT) and the eluates were diluted with Re-Chip buffer and reimmunoprecipitated with anti-p53 antibody (left gels) or anti-TBP antibody (right gels). The resulting ReChIP precipitates were analyzed by PCR (as described for FIG. 5A, lower panel) for the presence of the various Bax gene promoter region sequences.

Figure 5C:
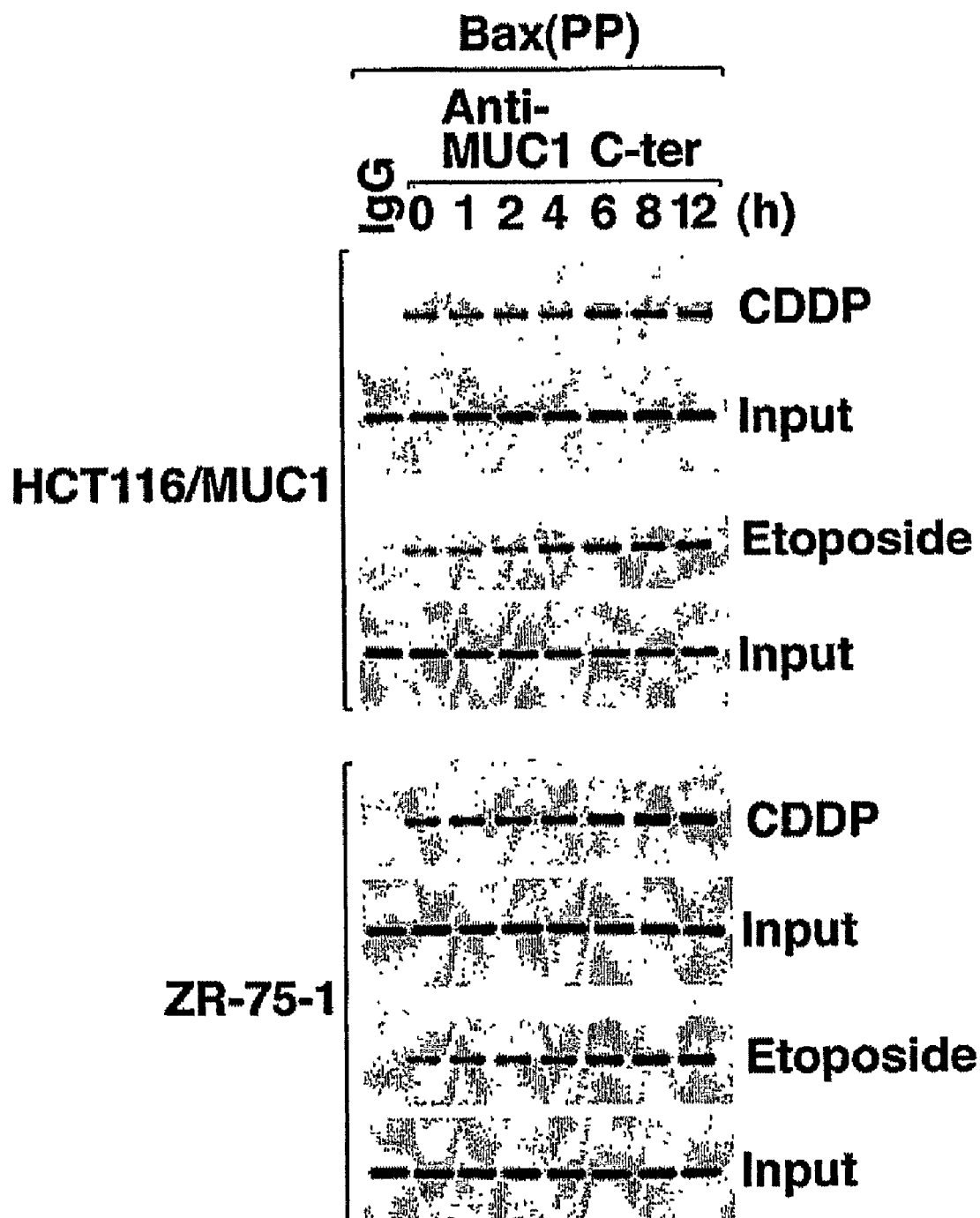

FIG. 5C is a series of photographs of ethidium bromide-stained electrophoretic gels of PCR reactions of chromatin immunoprecipitations (ChIP). HCT116/MUC1 cells (top four gels) or ZR-75-1 cells were treated with 50 µM CDDP (cisplatin) or etoposide ("Etoposide") for the indicated periods of time. Soluble chromatin extracted from all cell samples was immunoprecipitated with anti-MUC1 C-ter antibody and the resulting precipitates and whole unprecipitated soluble chromatin ("Input") were analyzed by PCR for the presence of the Bax gene PP as described for FIG. 5A, lower panel.

Figure 5D:
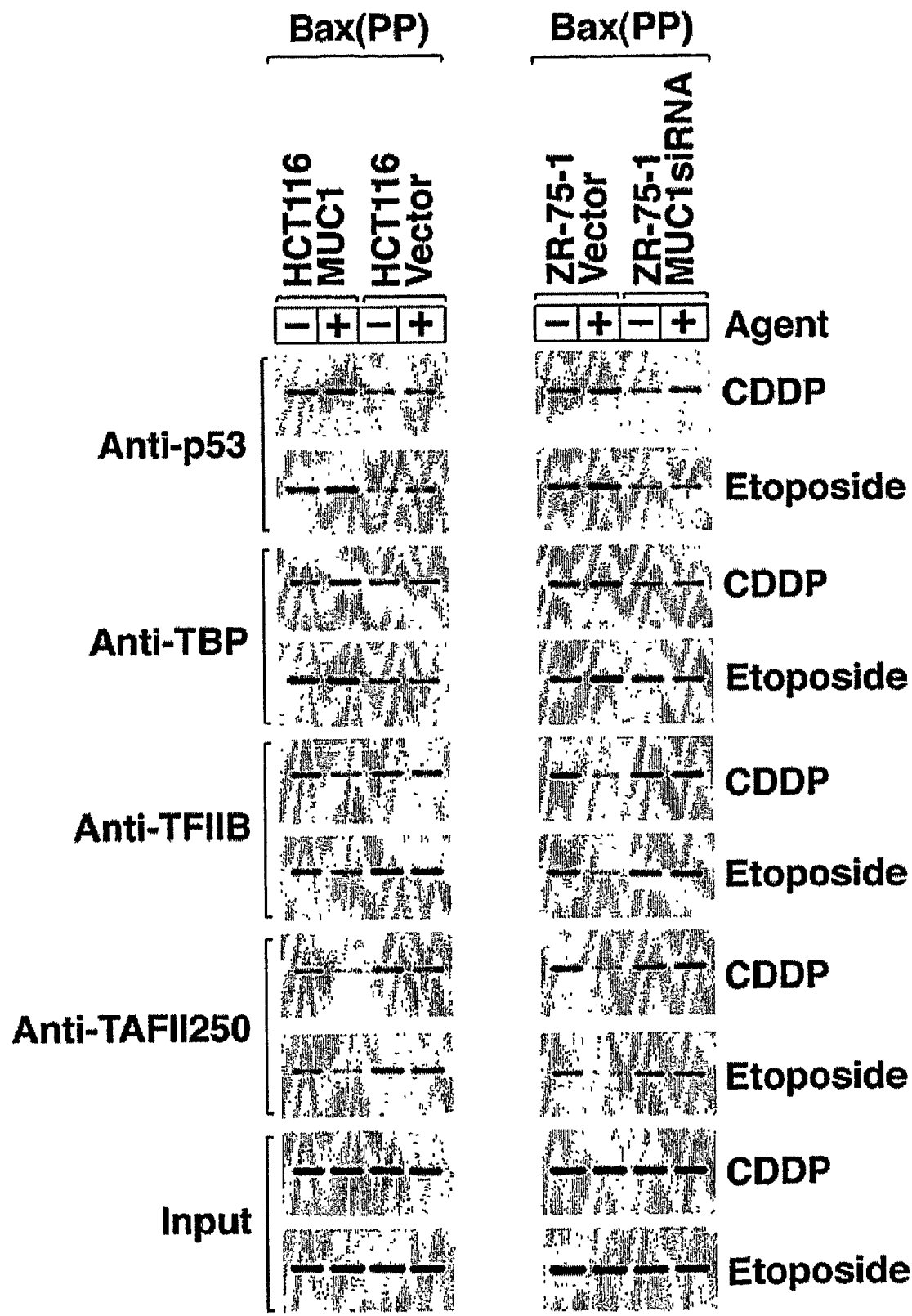

FIG. 5D is a series of photographs of ethidium bromide-stained electrophoretic gels of PCR reactions of chromatin immunoprecipitations (ChIP). HCT116/MUC1 cells and HCT116/vector cells (left panel) or ZR-75-1 cells and ZR-75-1/MUC1siRNA (right panel) were left untreated ("−") or were treated ("+") with 50 µM CDDP (cisplatin) or etoposide ("Etoposide") for 8 h. Soluble chromatin was extracted from all cell samples and immunoprecipitated with anti-p53 antibody, anti-TBP antibody, anti-TFIIB antibody, or anti-TAFII250 antibody and the resulting precipitates and whole unprecipitated soluble chromatin ("Input") were analyzed by PCR for the presence of the Bax gene PP as described for FIG. 5A, lower panel.

Figure 6A:
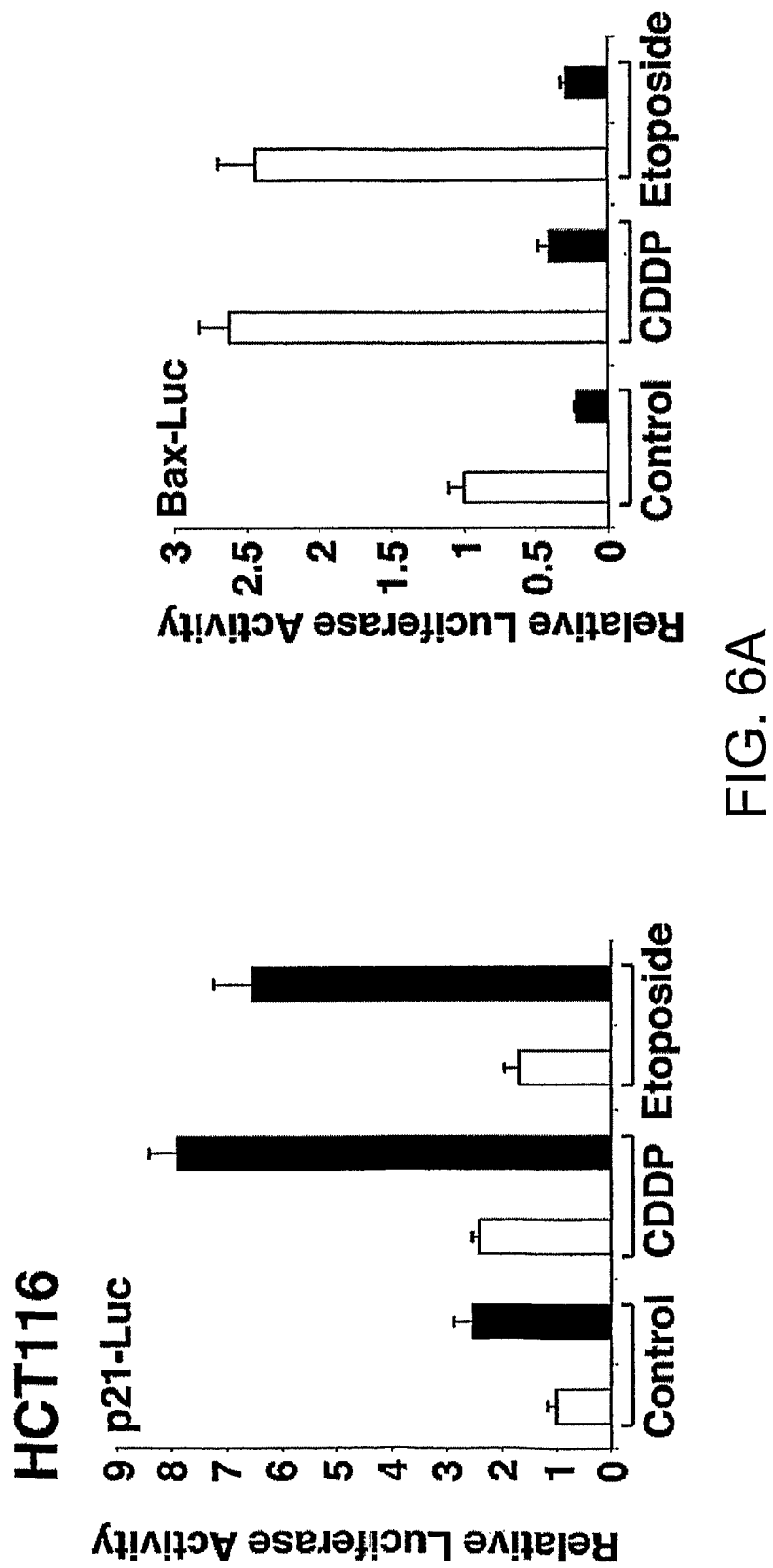

FIG. 6A is a pair of bar graphs showing luciferase activity. HCT116/vector cells (open bars) and HCT116/MUC1 cells (solid bars) were transiently transfected with the p21-Luc reporter construct ("p21-Luc"; left panel) or the Bax gene promoter Luc reporter construct ("Bax-Luc"; right panel). At 24 h after transfection, the cells were left untreated ("Control") or were treated with 10 µM CDDP or etoposide ("Etoposide") for 24 h and then assayed for luciferase activity. The results are expressed as the fold-activation (mean±SD (standard deviation of 3 separate experiments) compared to that obtained with untreated HCT116/vector cells (assigned a value of 1). Similar results were obtained with the separately isolated HCT116/vector-B and HCT116/MUC1-B cell clones (data not shown).

Figure 6B:
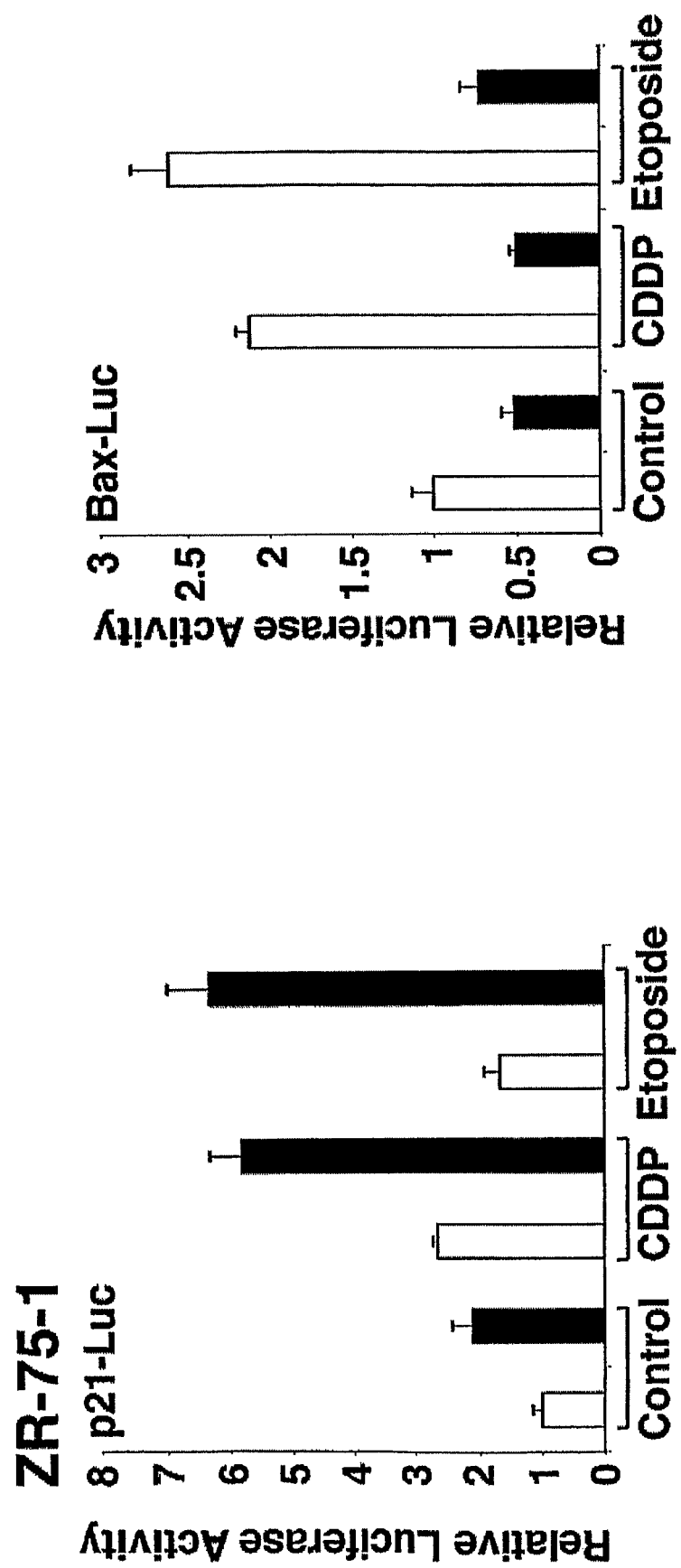

FIG. 6B is a pair of bar graphs showing the luciferase activity. ZR-75-1/vector cells (solid bars) and ZR-75-1/MUC1siRNA cells (open bars) were transiently transfected with the p21-Luc reporter construct ("p21-Luc"; left panel) or the Bax gene promoter Luc reporter construct ("Bax-Luc"; right panel). At 24 h after transfection, the cells were left untreated ("Control") or were treated with 10 µM CDDP or etoposide ("Etoposide") for 24 h and then assayed for luciferase activity. The results are expressed as the fold-activation (mean±SD of 3 separate experiments) compared to that obtained with untreated ZR-75-1/MUC1 siRNA cells (assigned a value of 1).

Figure 6C:
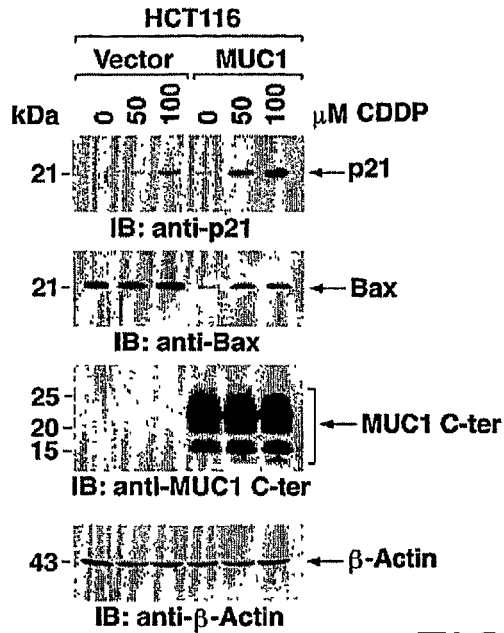
Figure 6C:
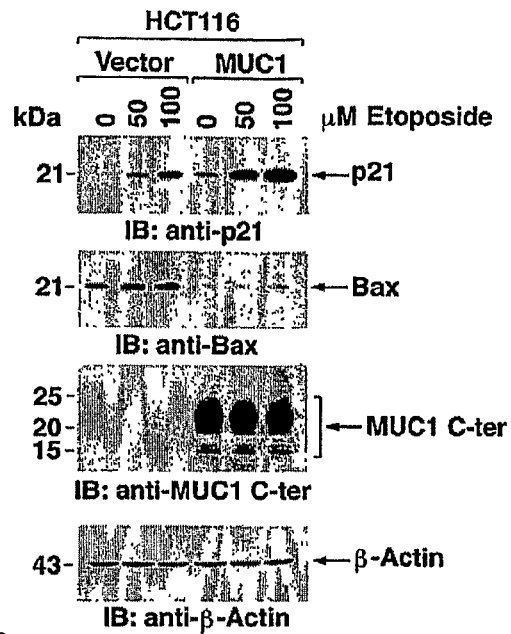

FIGS. 6C and D are photographs of a series of immunoblots. HCT116/MUC1 and HCT116/vector cells (FIG. 6C) and ZR-75-1/Vector and ZR-75-1/MUC1siRNA cells (FIG. 6D) and were left untreated ("0") or were treated with 50 or 100 µM CDDP or etoposide ("Etoposide") for 24 h. Unprecipitated lysates were subjected to immunoblot analysis ("IB") with anti-p21 antibody, anti-MUC1 C-ter antibody, anti-Bax antibody, or anti-β-Actin antibody. The positions of molecular weight markers ("kDa") are indicated on the left and of p21, Bax, MUC1 C-ter, and β-Actin are indicated on the right of the blots.

Figure 7A:
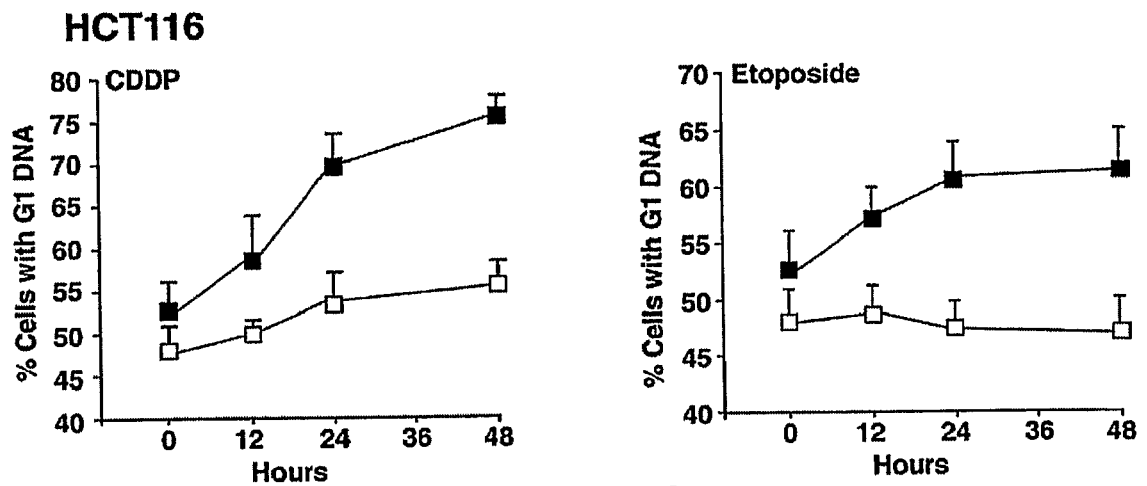

FIGS. 7A and B are line graphs showing the effect of CDDP (12.5 µM; left panels) and etoposide (12.5 µM; right panels) on the relative number of HCT116/vector cells (FIG. 7A; open squares), HCT116/MUC1 cells (FIG. 7A; filled squares), ZR-75-1/vector cells (FIG. 7B; filled triangles), and ZR-75-1/MUCsiRNA cells (FIG. 7B; open triangles) in the G1 phase of the cell cycle as measured by fluorescence flow cytometry (FFC). The results are presented as the percentage (mean±SD of three separate experiments) of cells in G1 phase.

Figure 7B:
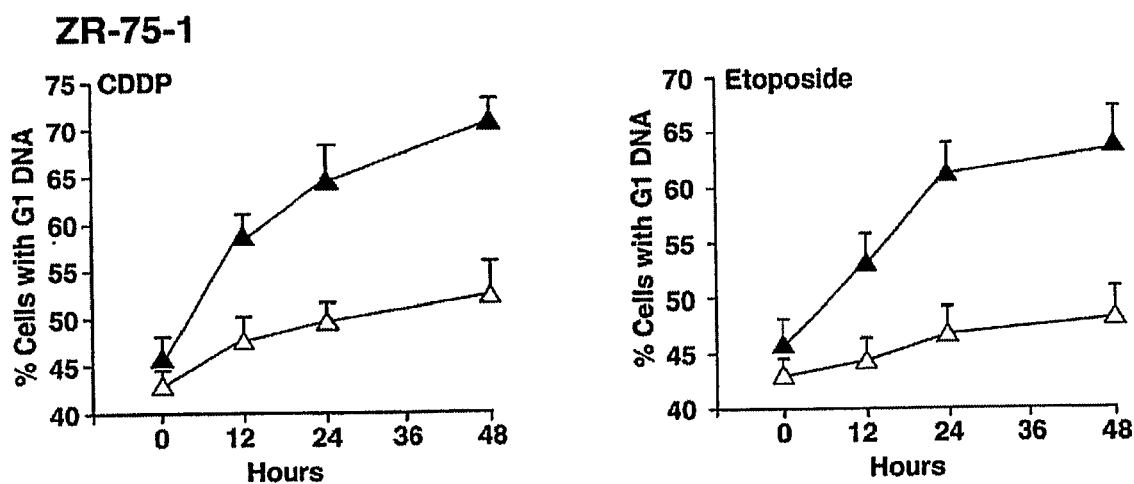
Figure 7C:
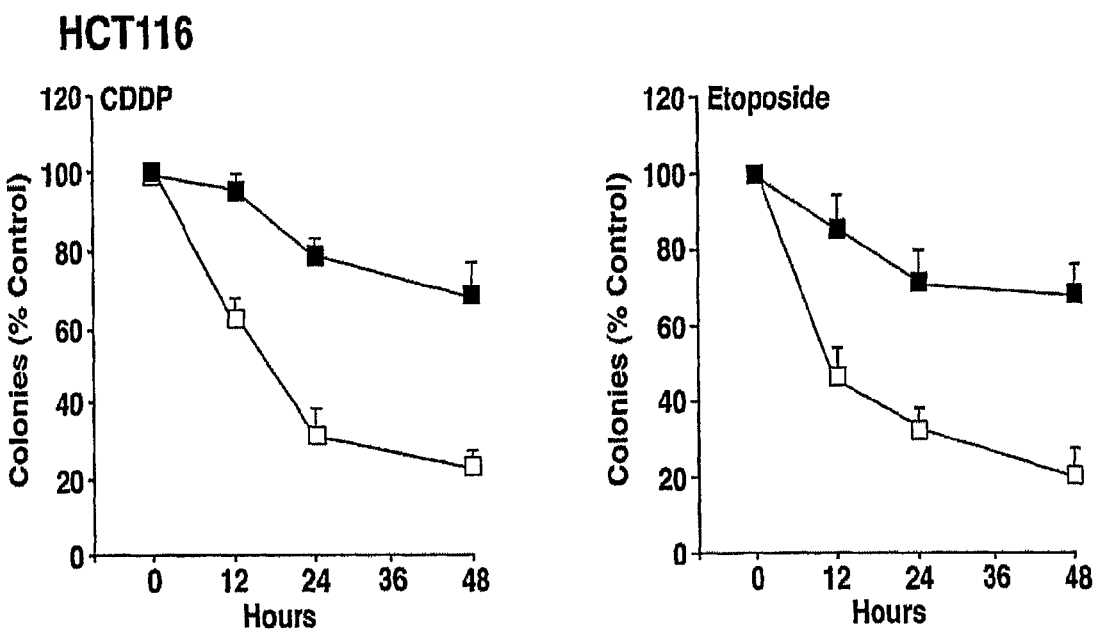
Figure 7D:
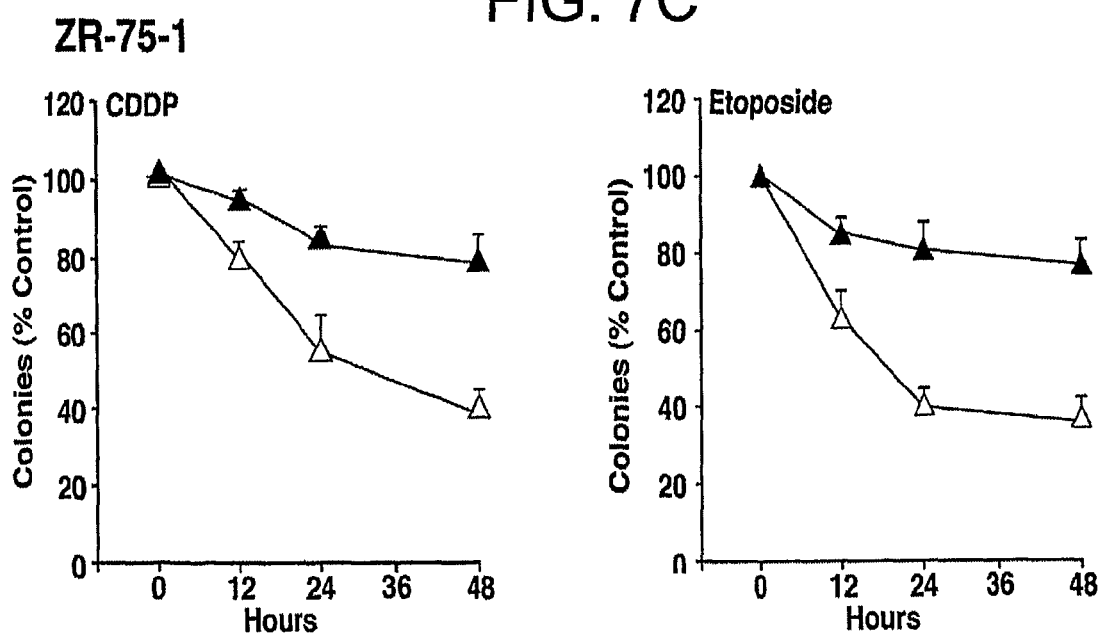

FIGS. 7C and D are line graphs showing the effect of CDDP (12.5 µM; left panels) and etoposide (12.5 µM; right panels) pretreatment (for the indicated periods of time) on the relative number of colonies formed after an 8 day culture (in the absence of drug) of HCT116/vector cells (FIG. 7C; open squares), HCT116/MUC1 cells (FIG. 7C; filled squares), ZR-75-1/Vector cells (FIG. 7D; filled triangles), and ZR-75-1/MUCsiRNA cells (FIG. 7D; open triangles) as measured by FFC. The results are presented as the number (mean±SD of three separate experiments) of colonies.

Figure 8A:
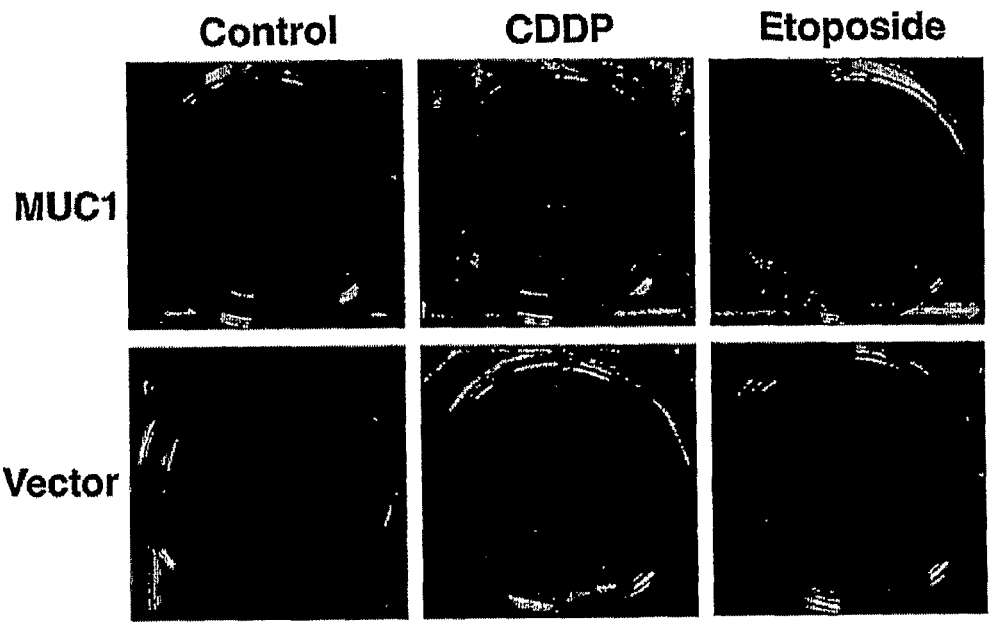
Figure 8B:
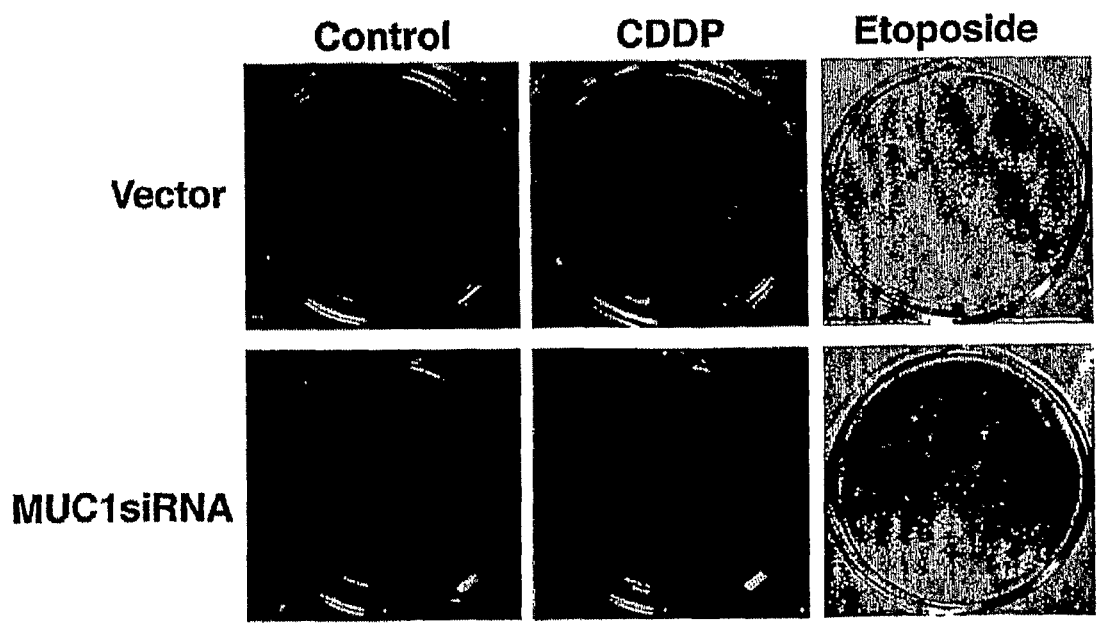

FIGS. 8A and B are a series of photographs of crystal violet-stained, culture well bottom-adherent colonies of HCT116/MUC1 cells (FIG. 8A, top row), HCT116/vector cells (FIG. 8A, bottom row), ZR-75-1/vector cells (FIG. 8B, top row), and ZR-75-1/MUC1siRNA cells (FIG. 8, bottom row) after culturing for 48 h in the presence of tissue culture medium only ("Control"), CDDP (50 μM), or etoposide ("Etoposide"; 50 μM).

Figure 9B:
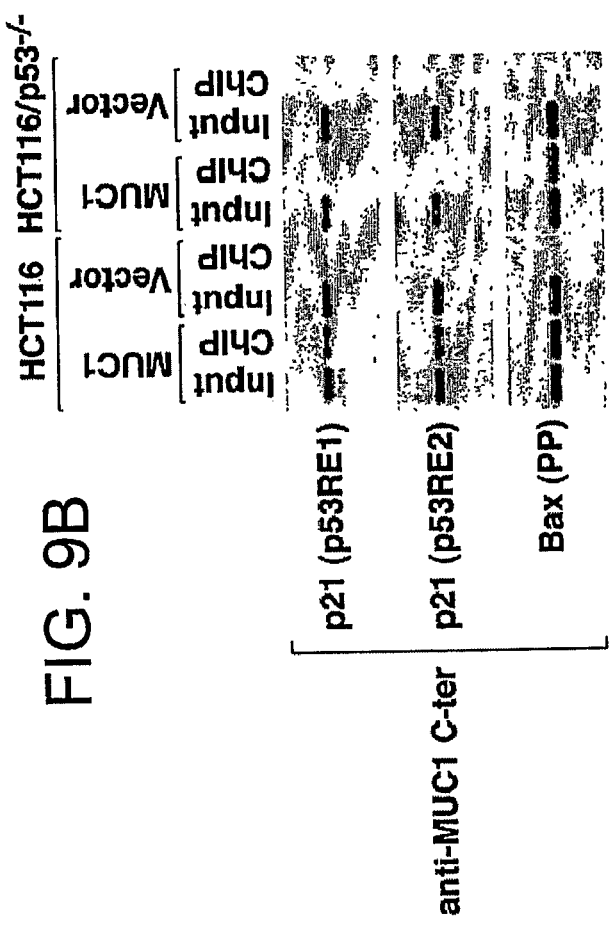
Figure 9A:
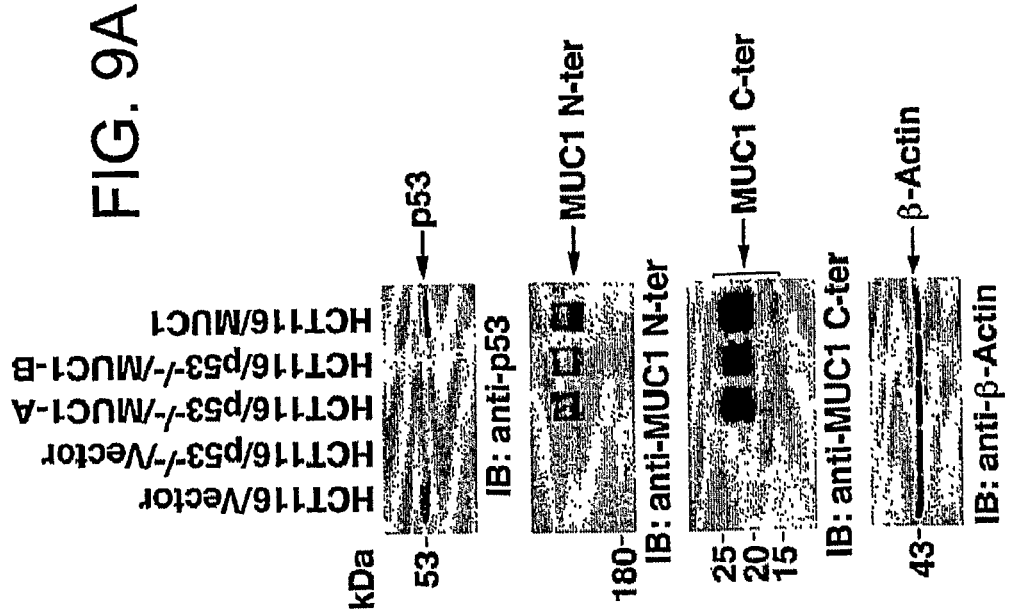

FIG. 9A is a series of photographs of immunoblots. Whole unprecipitated lysates of HCT116/MUC1 cells and HCT116/vector cells and two separate colonies of HCT116/p53$^{-/-}$/MUC1 cells (HCT116/p53$^{-/-}$/MUC1-A and HCT116/p53$^{-/-}$/MUC1-B), which are HCT116 cells in which both alleles of p53 have been disrupted and that have been transfected with an expression vector encoding full-length mature MUC1, were subjected to immunoblot analysis ("113") with anti-p53 antibody, anti-MUC1 N-ter antibody, anti-MUC1 C-ter antibody, or anti-β-Actin antibody. The positions of molecular weight markers ("kDa") are indicated on the left and of p53, MUC1 N-ter, MUC1 C-ter, and β-Actin are indicated on the right of the blots.

FIG. 9B is a series of photographs of ethidium bromide-stained agarose electrophoretic gels of PCR reactions of chromatin immunoprecipitations (ChIP). Soluble chromatin from HCT116 cells (top gels) or HCT116/p53$^{-/-}$ cells (HCT116 cells in which both alleles of p53 have been disrupted) was immunoprecipitated with anti-MUC1 C-ter antibody ("anti-MUC1 C-ter". DNA was extracted from the resulting immunoprecipitates and the final DNA extractions ("ChIP") and unprecipitated whole chromatin ("Input") were amplified in polymerase chain reactions (PCR) using primers that cover the p53RE1 and p53RE2 of the p21 gene and the proximal promoter (PP) of the Bax gene. All the PCR reactions were analyzed by ethidium bromide staining of gel electrophoretograms.

Figure 9C:
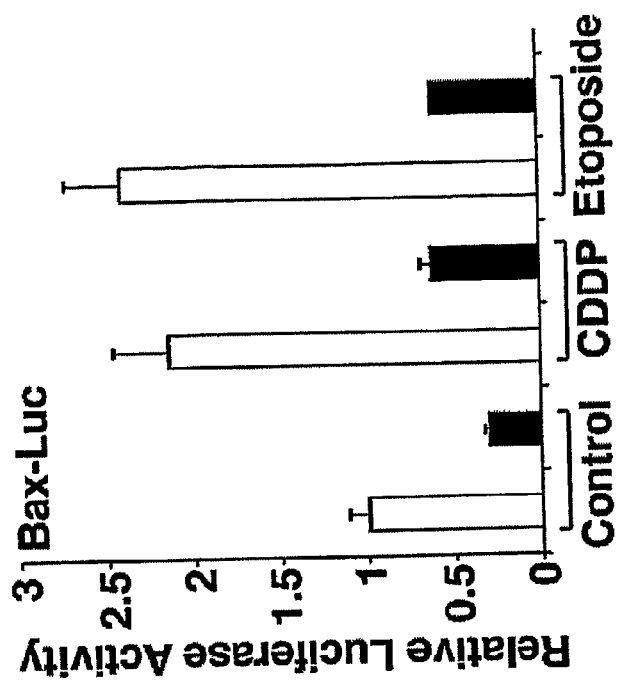
Figure 9C:
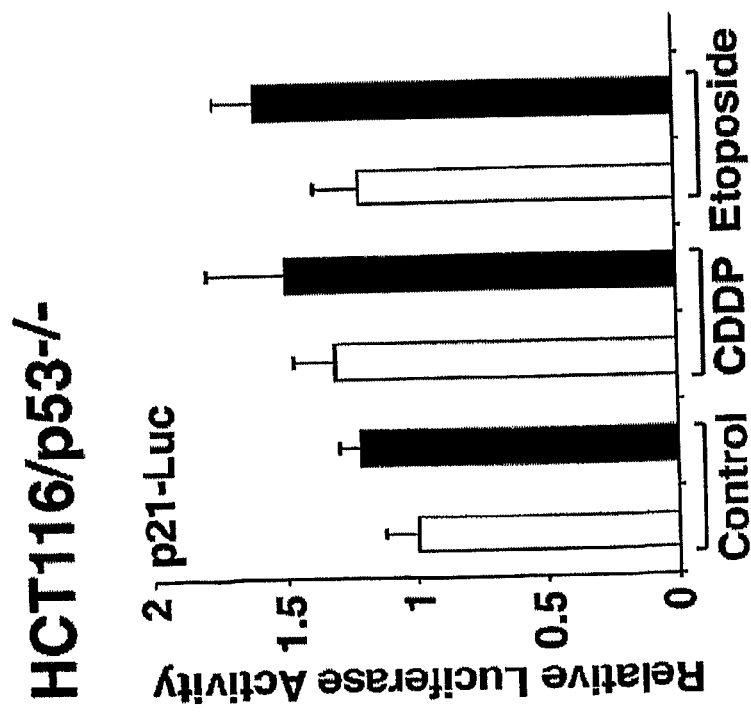

FIG. 9C is a pair of bar graphs showing luciferase activity. HCT116/p53$^{-/-}$/vector (HCT116 cells in which both alleles of p53 have been disrupted and that have been stably transfected with a control "empty" expression vector; open bars) and HCT116/p53$^{-/-}$/MUC1 cells (HCT116 cells in which both alleles of p53 have been disrupted and that have been stably transfected with a vector containing cDNA encoding full-length MUC1; solid bars) were transiently transfected with the p21-Luc (left panel) or Bax-Luc (right panel) reporter constructs. At 24 h after transfection, the cells were left untreated ("Control") or treated with 10 □M cisplatin or etoposide for 24 h and then assayed for luciferase activity. The results are expressed as the fold-activation (mean±SD of 3 separate experiments) compared to that obtained with untreated HCT116/p53$^{-/-}$/vector cells (assigned a value of 1). Similar results were obtained with the separately isolated HCT116/p53$^{-/-}$/MUC1 clones described for FIG. 9A (data not shown).

Figure 9D:
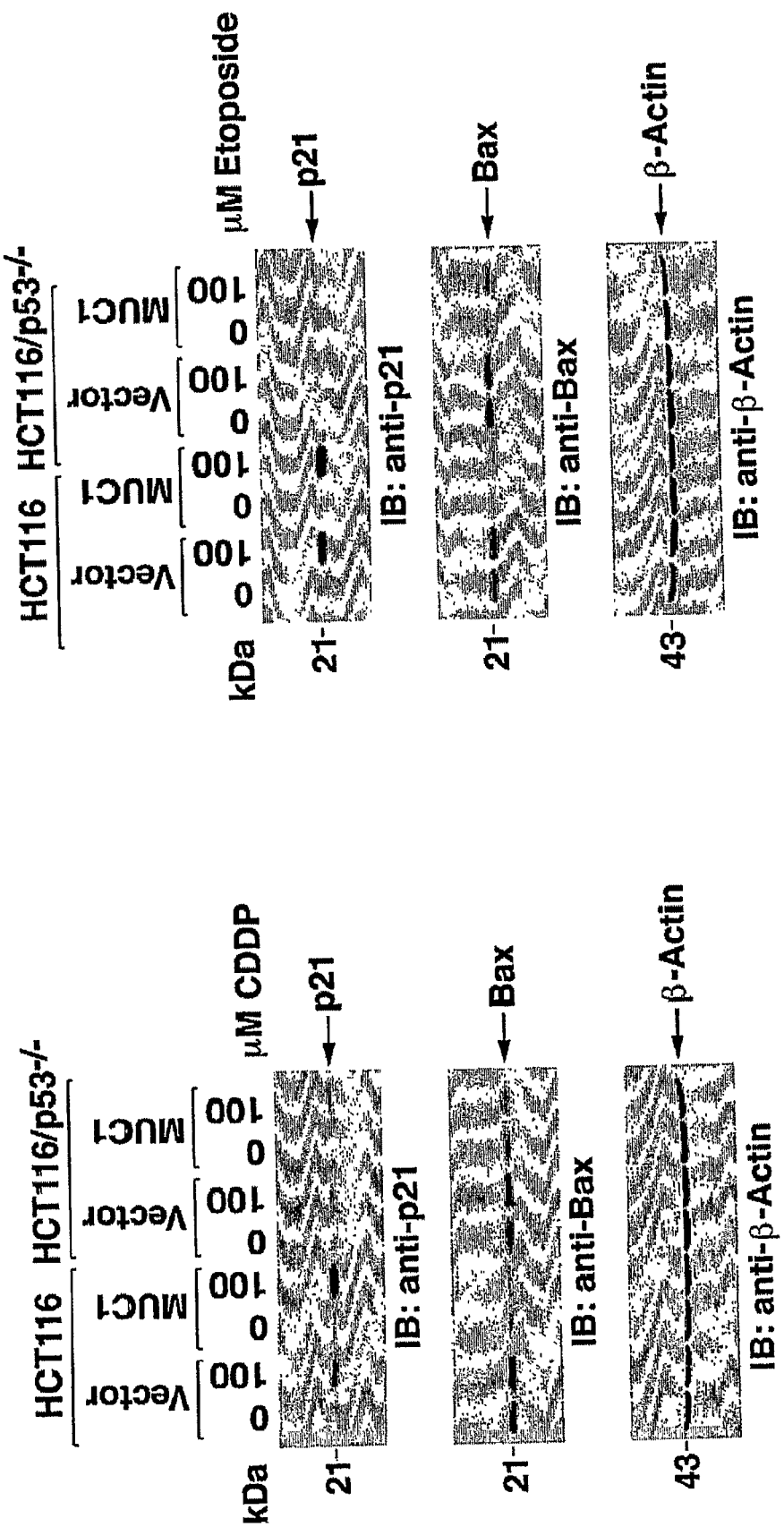

FIG. 9D is a series of photographs of immunoblots. HCT116 cells or HCT116/p53$^{-/-}$ cells were left untreated ("0") or were treated with 100 μM CDDP (left panel) or etoposide ("Etoposide"; right panel) for 24 h. Unprecipitated lysates were subjected to immunoblot analysis ("IB") with anti-p21 antibody, anti-Bax antibody, or anti-β-Actin antibody. The positions of molecular weight markers ("kDa") are indicated on the left and of p21, Bax, and β-Actin are indicated on the right of the blots.

Figure 9F:
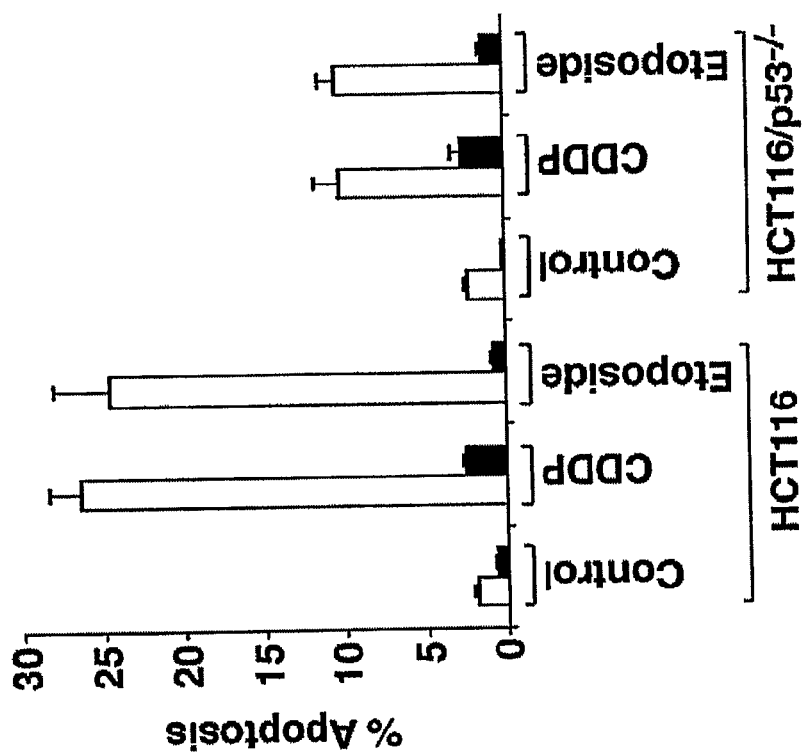
Figure 9E:
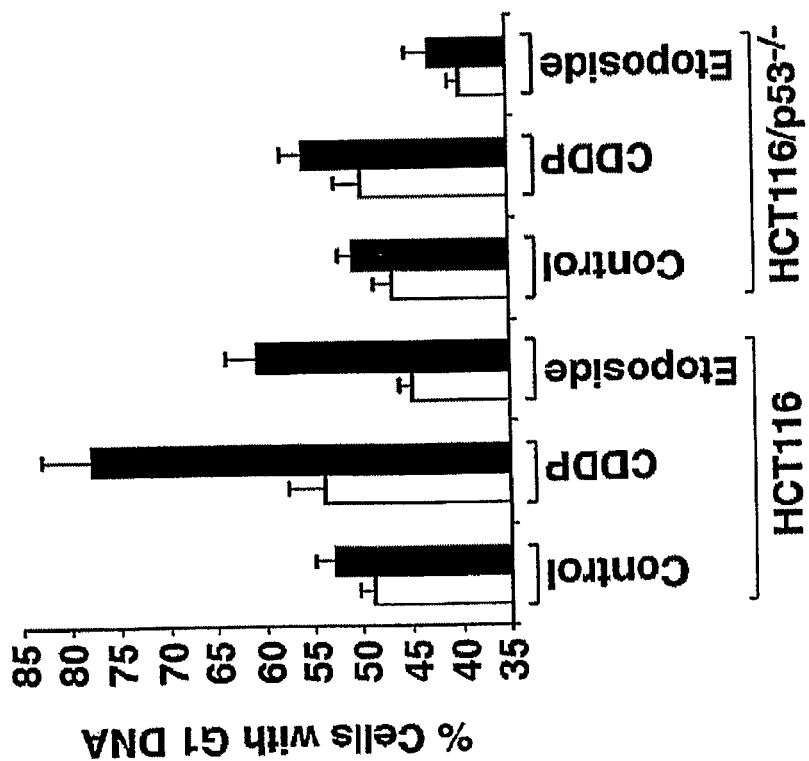

FIG. 9E is a bar graph showing the effect of no treatment ("Control") and treatment for 48 h with CDDP (25 μM) and etoposide (12.5 μM) on the relative number of HCT116/vector cells and HCT116/p53$^{-/-}$ cells (open bars) or HCT116/MUC1 cells and HCT116/p53$^{-/-}$/MUC1 cells (filled bars) in the G1 phase of the cell cycle as measured by FFC. The results are presented as the percentage (mean±SD of three separate experiments) of cells in G1 phase.

FIG. 9F is a bar graph showing the effect of no treatment ("Control") and treatment for 72 h with CDDP (50 μM) and etoposide (25 μM) on the relative number of HCT116/vector cells and HCT116/p53$^{-/-}$ cells (open bars) and HCT116/MUC1 cells and HCT116/p53$^{-/-}$/MUC1 cells (filled bars) in apoptosis (i.e., having sub G1-DNA) as measured by FFC. The results are presented as the percentage (mean±SD of three separate experiments) of cells with sub-G1 DNA.

FIG. 10A is a series of photographs of immunoblots. Whole unprecipitated lysates from ZR-75-1/vector cells and ZR-75-1/MUC1siRNA cells infected with a control "empty" adenovirus ("Control") or an adenovirus expressing p53siRNA ("Ad.p53siRNA") were subjected to immunoblot ("IB") analysis with anti-MUC1 C-ter antibody, anti-MUC1 N-ter antibody, anti-p53 antibody, or anti-β-Actin antibody. The positions of molecular weight markers ("kDa") are indicated on the left and of MUC1 C-ter, MUC1 N-ter, p53, and β-Actin are indicated on the right of the blots.

FIG. 10B is a series of photographs of ethidium bromide-stained agarose electrophoretic gels of PCR reactions of chromatin immunoprecipitations (ChIP). Soluble chromatin from ZR-57-1 cells or ZR-57-1/Ad.p53siRNA cells (ZR-57-1 cells infected Ad.p53siRNA) were immunoprecipitated with anti-MUC1 C-ter antibody ("anti-MUC1 C-ter"). DNA was extracted from the resulting immunoprecipitates and the final DNA extractions ("ChIP") and unprecipitated whole chromatin ("Input") were amplified in polymerase chain reactions (PCR) using primers that cover the p53RE1 and p53RE2 of the p21 gene and the proximal promoter (PP) of the Bax gene. All the PCR reactions were analyzed by ethidium bromide staining of gel electrophoretograms.

Figure 10C:
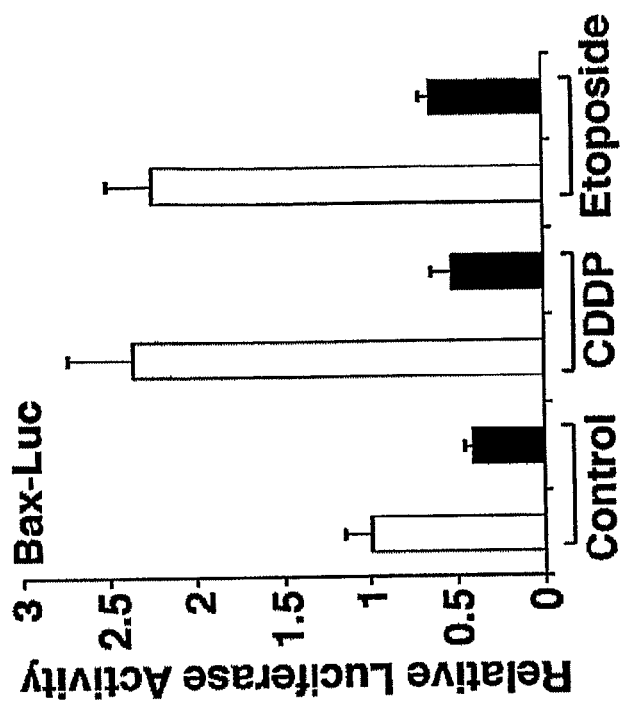
Figure 10C:
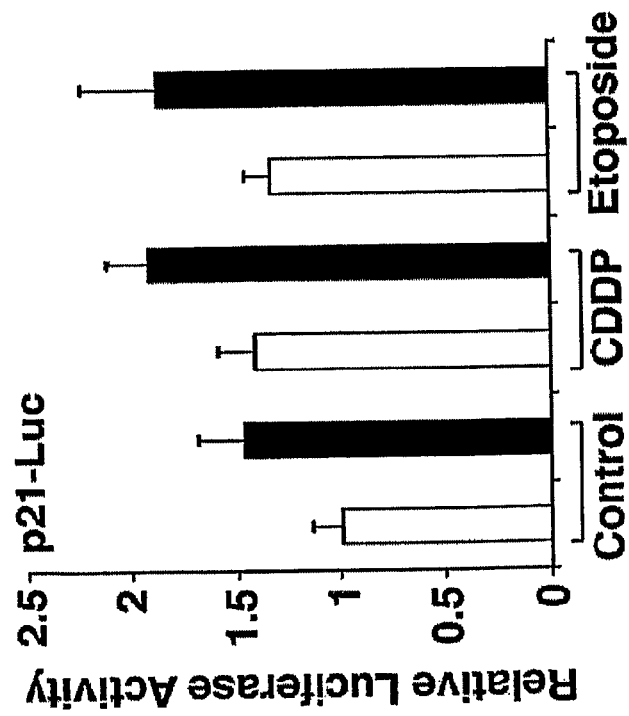

FIG. 10C is a pair of bar graphs showing luciferase activity. ZR-75-1/MUC1siRNA (open bars) and ZR-75-1/vector cells (filled bars) were infected with Ad.p53siRNA for 24 h and then transfected with the p21-Luc (left panel) or Bax-Luc (right panel) reporter constructs. At 24 h after transfection, the cells were left untreated ("Control") or treated with 10 μM cisplatin or etoposide for 24 h and then assayed for luciferase activity. The results are expressed as the fold-activation (mean±SD of 3 separate experiments) compared to that obtained with untreated ZR-75-1/MUC1siRNA/Ad.p53siRNA cells (assigned a value of 1). Similar results were obtained with the separately isolated ZR-75-1/vector and ZR-75-1/MUC1siRNA clones infected with Ad.p53siRNA (data not shown).

Figure 10D:
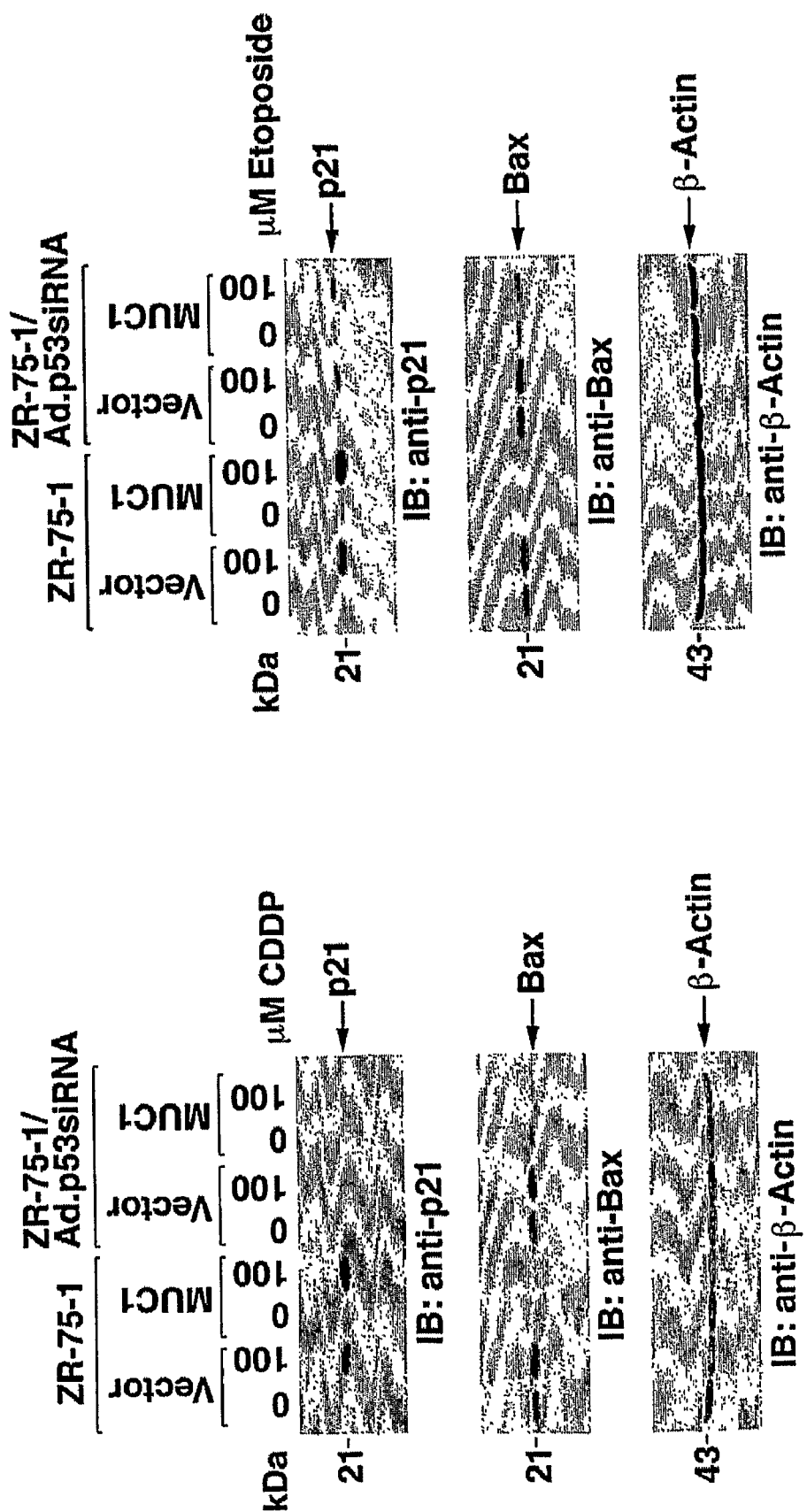

FIG. 10D is a series of photographs of immunoblots. ZR-75-1/vector cells and ZR-75-1/MUC1 cells, either not infected or infected with Ad.p53siRNA, were left untreated ("0") or were treated with 100 μM CDDP (left panel) or etoposide ("Etoposide"; right panel) for 24 h. Unprecipitated lysates were subjected to immunoblot analysis ("IB") with anti-p21 antibody, anti-Bax antibody, or anti-β-Actin antibody. The positions of molecular weight markers ("kDa") are indicated on the left and of p21, Bax, and β-Actin are indicated on the right of the blots.

Figure 10F:
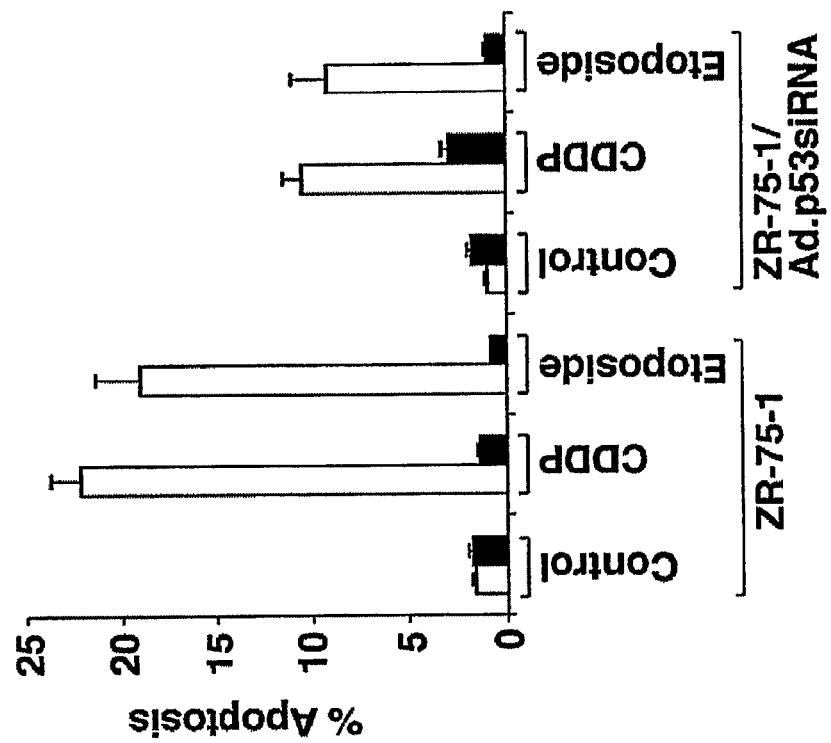
Figure 10E:
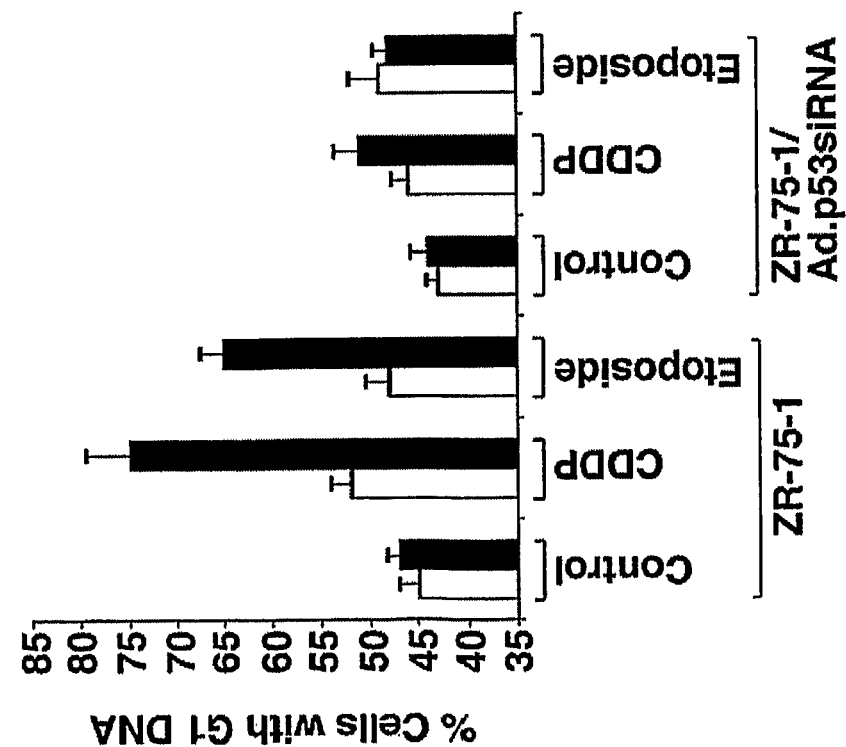

FIG. 10E is a bar graph showing the effect of no treatment ("Control") and treatment for 48 h with CDDP (25 μM) and etoposide ("Etoposide"; 12.5 μM) on the relative number of ZR-75-1/MUC1siRNA cells and ZR-75-1/MUC1siRNA/Ad.p53siRNA cells (open bars) or ZR-75-1/vector cells and ZR-75-1/vector/Ad.p53siRNA cells (filled bars) in the G1 phase of the cell cycle as measured by FFC. The results are presented as the percentage (mean±SD of three separate experiments) of cells in G1 phase.

FIG. 10F is a bar graph showing the effect of no treatment ("Control") and treatment for 72 h with CDDP (50 μM) and etoposide (25 μM) on the relative number of ZR-75-1/MUC1siRNA cells and ZR-75-1/MUC1siRNA/Ad.p53siRNA cells (open bars) or ZR-75-1/vector cells and ZR-75-1/vector/Ad.p53siRNA cells (filled bars) in apoptosis (i.e., having sub G1-DNA) as measured by fluorescence flow cytometry FFC. The results are presented as the percentage (mean±SD of three separate experiments) of cells with sub-G1 DNA.

FIG. 11A is a depiction of the amino acid sequence of a human MUC1 protein (SEQ ID NO:3). The signal peptide consists of amino acid 1 to about amino acid 18. The N-terminal subunit (MUC1 N ter) that is cleaved from mature pre-MUC1 and in mature MUC1 associates with the C-terminal subunit (MUC1 C—ter), in the isoform shown, extends from about amino acid 19 to amino acid 317. MUC1 N-ter varies in length depending on the number of tandem repeats. The C-terminal subunit (MUC1 C-ter) consists of amino acids 318-475. The transmembrane domain consists of amino acids 376-403 and the cytoplasmic domain (CD) (SEQ ID NO: 2) consists of amino acids 404-475.

FIG. 11B is a depiction of the cytoplasmic domain (SEQ ID NO:2) of human MUC1.

FIG. 12 is a depiction of the amino acid sequence of human p53 (SEQ ID NO:1)

DETAILED DESCRIPTION

The human DF3/MUC1 integral membrane glycoprotein is expressed on the apical borders of normal secretory epithelial cells [Kufe et al. (1984) Hybridoma 3:223-232]. With transformation and loss of polarity, MUC1 is found at high levels in the cytosol and over the entire surface of carcinoma cells [Kufe et al. (1984); Perey et al. (1992) Cancer Res. 52:2563-3568]. Mature MUC1 is expressed as a heterodimer (consisting of the cleaved MUC1 N-terminal subunit bound to the MUC1 C-terminal subunit) following synthesis as a single polypeptide and cleavage in the endoplasmic reticulum [Ligtenberg et al. (1992) J. Biol. Chem. 267:6171-6177]. The MUC1 N-terminal subunit (MUC1 N-ter) consists of variable numbers of 20 amino acid tandem repeats that are modified by O-glycans [Gendler et al. (1988) J. Biol. Chem. 263:12820-12823; Siddiqui et al. (1988) Proc. Natl. Acad. Sci. USA 85:2320-2323] (FIG. 11). MUC1 N-ter is tethered to the cell membrane through dimerization with the C-terminal subunit (MUC1 C-ter), which consists of a 58 amino acid extracellular domain, a 28 amino acid transmembrane domain and a 72 amino acid cytoplasmic tail [Merlo et al. (1989) Cancer res. 49:6966-6971] (FIG. 11). MUC1 interacts with members of the ErbB family [Li et al. (2001b) J. Biol. Chem. 276:35239-35242; Li et al. (2003c) Mol. Cancer. Res. 1:765-775; Schroeder et al. (2001) J. Biol. Chem. 276:13057-13064] and is targeted to the nucleus and mitochondria [Li et al. (2003c); Ren et al. (2004) Cancer Cell 5:163-175]. MUC1 also associates with β-catenin [Yamamoto et al. (1997) J. Biol. Chem. 272:12492-12494] and this interaction is regulated by GSK3β (glycogen synthase kinase 3β)-, Src- and PKCδ (protein kinase Cδ)-mediated phosphorylation of the MUC1 cytoplasmic domain (MUC1-CD) [Li et al. (1998) Mol. Cell. Biol. 18:7216-7224; Li et al. (2003a) Cancer Biol. Ther. 2:187-193; Li et al. (2001a) J. Biol. Chem. 276:6061-6064; Li et al. (2001b); Ren et al. (2002b) J. Biol. Chem. 277:17616-17622]. Overexpression of MUC1 is sufficient to confer transformation [Huang et al. (2003) Cancer Biol. Ther. 2:702-706; Li et al. (2003b) Oncogene 22:6107-6110; Schroeder et al. (2004) J. Biol. Chem. 276:13057-13064] and to attenuate oxidative and genotoxic stress-induced apoptosis (Ren et al. (2004); Yin et al. (2004) J. Biol. Chem. 279:45721-45727; Yin et al. (2003) J. Biol. Chem. 278:35458-35464].

The p53 tumor suppressor functions in the cellular response to stress by inducing growth arrest, DNA repair, senescence, differentiation or apoptosis [Levine (1997) Cell 88:323-331]. Genotoxic stress, oxidative damage, hypoxia, nucleotide depletion, heat shock and oncogene expression are associated with stabilization of p53 and induction of p53-mediated transcription. Selective transactivation of p53 target genes dictates the induction of apoptosis or a growth arrest and repair response [Chao et al. (2000) EMBO J. 19:4967-4975; Jimenez et al. (2000) Nat. Genet. 26:37-43]. The amino acid sequence of full-length human p53 is shown in FIG. 12. Genes encoding death receptors Fas/CD95 and DR5 [Muller et al. (1998) J. Exp. Med. 188:2033-2045; Wu et al. (1997) Nat. Genet. 17:141-143] or proapoptotic effectors such as Bax, Noxa and Puma [Miyashita et al. (1995) Cell 80:293-299; Oda et al. (2000a) Science 288:1053-1058; Yu et al. (2001) Mol. Cell. 7:673-682] contribute to the induction of a p53-dependent apoptotic response. Alternatively, the growth arrest response to p53 activation is mediated in large part by induction of the p21 gene [El-Deiry et al. (1993) Cell 75:817-825]. p21 plays a role in promoting cell cycle progression and preventing apoptosis [Asada et al. (1999) EMBO J. 18:1223-1234; Dong et al. (2004) Cell Signal 16:263-269; Dupont et al. (2003) J. Biol. Chem. 278:37256-37264; Weiss (2003) Cancer Cell 4:425-429; Zhang et al. (2003) J. Biol. Chem. 278:27903-27909]. The choice of cell fate is influenced by growth factor stimulation, proliferation status and extent of damage [Vousden et al. (2002) Nat. Rev. Cancer; Wahl et al. (2001) Nat. Cell. Biol. 3:E277-286]. Promoter selectivity for p53-induced apoptosis is also influenced by phosphorylation of p53 on serines 20 and 46 [Jack et al. (2002) Proc. Natl. Acad. Sci. USA 99:9825-9829; Oda et al. (2000b) Cell 102:849-862] and by interactions between p53 and members of the ASPP family [Samuels-Lev et al. (2001) Mol. Cell. 8:781-794], the JMY p300-binding protein [Shikama et al. (1999) Mol. Cell. 4:365-376], the E2F transcription factor [Hsieh et al. (2002) Mol. Cell. Biol. 22:78-93], and the p53 family members p73/p63 [Flores et al. (2002) Nature 416:560-564].

The present studies demonstrate that MUC1 C-ter, and not MUC1 N-ter, interacts with p53. Binding of MUC1 to p53 was detectable constitutively and increased in the response to DNA damage. The results shown herein also demonstrate that MUC1 is detectable with p53 on promoters of the p53-responsive p21 and Bax genes. The present findings also show that MUC1 is detectable with p53 on the p53REs in the p21 gene promoter and that MUC1 occupancy of these elements is increased by DNA damage and dependent on p53. In addition, the finding that MUC1 coactivates p21 gene transcription can be explained, at least in part, by MUC1-induced recruitment of CBP (CREB-binding protein) and not HDAC1 (histone deacetylase C1) to the p21 gene promoter. Binding of CBP to p53 is necessary for histone acetylation [Barlev et al. (2001) Mol. Cell. 8:1243-1254] and p53-mediated activation of p21 gene transcription [Liu et al. (2003) J. Biol. Chem. 278:17557-17565; Mujtaba et al. (2004) Mol. Cell. 13:251-263]. In this regard, the data described herein show that MUC1-induced recruitment of CBP to the p21 gene promoter was associated with increased acetylation of histone H4. Moreover, MUC1 expression was associated with activation of both the p21 gene promoter-Luc reporter and the endogenous p21 gene in the response to genotoxic stress. These findings indicate that the interaction between MUC1 and p53 contributes to the recruitment of CBP and thereby activation of p21 gene transcription.

Binding of p53 to the Bax gene promoter in cells is less compared with the p21 gene promoter [Kaeser et al. (2002) Proc. Natl. Acad. Sci. USA 99:95-100]. The present studies demonstrate that, in contrast to the p21 gene promoter, there is no detectable MUC1 occupancy of the p53-responsive element in the Bax gene promoter. There was also no detectable MUC1 binding to the Bax gene p53RE after DNA damage. Surprisingly, however, the presently described experiments showed that MUC1 immunoprecipitates with the Bax gene PP and that this association is increased by DNA damage. Coprecipitation of MUC1 with TBP further indicated that MUC1 occupies the region of the Bax gene PP that includes the basal transcription complex. Notably, p53 was detectable with MUC1 on the Bax gene PP, suggesting that MUC1 may be targeted to this region by a p53-dependent mechanism. However, decreases in p53 levels had little effect on MUC1 occupancy of the Bax gene PP. Thus, like p53, MUC1 may also associate with basal transcription factors. In this context, MUC1 occupancy of the Bax gene PP had no apparent effect on TBP, but decreased occupancy by TFIIB and TAFII250. Moreover, MUC1 expression was associated with attenuation of Bax gene activation by a p53-independent mechanism and derepression of the Bax gene promoter in the absence of MUC1 was observed in both p53-expressing and p53-non-expressing cells. The findings with the p21 and Bax genes thus indicate that MUC1 selectively regulates transcription of p53-responsive genes by DNA damage-induced binding of MUC1 in a promoter-specific manner.

In summary, the above results demonstrate that MUC1 enhances the intrinsic, as well as the genotoxic drug-induced, growth arrest response of cells to DNA damage by a mechanism dependent on p53. MUC1 also suppressed p53-dependent and p53-independent intrinsic, as well as genotoxic drug-induced, apoptotic responses to DNA damage.

Since MUC1 becomes associated with the p21 gene p53RE via its physical association with p53 and binding of MUC1 to the Bax gene PP is likely mediated by the binding of MUC1 to TBP, compounds that ablate, or at least inhibit, the interaction between MUC1 and p53 and/or the interaction between MUC1 and TBP are likely to be useful for enhancing the intrinsic apoptosis of cancer cells and also the cancer cell cytocidal effects of genotoxic agents such as ionizing radiation and chemotherapeutic drugs. Moreover, such compounds could also be useful as prophylactic agents in subjects that have an increased risk (due, for example, to genetic, physiological, or environmental factors) of the development of a malignancy.

Methods of Screening for Inhibitory Compounds

The invention provides in vitro methods for identifying compounds (small molecules or macromolecules) that inhibit binding of MUC1-binders (p53 and TBP) to MUC1.

These methods can be performed using: (a) isolated MUC1 test agents and MUC1-binder test agents; or (b) cells expressing a MUC1 test agent and one or both MUC1-binder test agents.

The term "isolated" as applied to any of the above-listed polypeptide test agents refers to a polypeptide, or a peptide fragment thereof, which either has no naturally-occurring counterpart or has been separated or purified from components which naturally accompany it, e.g., in tissues such as pancreas, liver, spleen, ovary, testis, muscle, joint tissue, neural tissue, gastrointestinal tissue or tumor tissue (e.g., breast cancer or colon cancer tissue), or body fluids such as blood, serum, or urine. Typically, the polypeptide or peptide fragment is considered "isolated" when it is at least 70%, by dry weight, free from the proteins and other naturally-occurring organic molecules with which it is naturally associated. Preferably, a preparation of a test agent is at least 80%, more preferably at least 90%, and most preferably at least 99%, by dry weight, the test agent. Since a polypeptide that is chemically synthesized is, by its nature, separated from the components that naturally accompany it, a synthetic polypeptide test agent is "isolated."

An isolated polypeptide test agent can be obtained, for example, by extraction from a natural source (e.g., from tissues); by expression of a recombinant nucleic acid encoding the polypeptide; or by chemical synthesis. A polypeptide test agent that is produced in a cellular system different from the source from which it naturally originates is "isolated," because it will necessarily be free of components which naturally accompany it. The degree of isolation or purity can be measured by any appropriate method, e.g., column chromatography, polyacrylamide gel electrophoresis, or HPLC analysis.

Prior to testing, any of the test agents can undergo modification, e.g., phosphorylation or glycosylation, by methods known in the art.

In methods of screening for compounds that inhibit or enhance binding of an isolated MUC1 test agent to an isolated MUC1-binder test agent, a MUC1 test agent is contacted with a MUC1-binder test agent in the presence of one or more concentrations of a test compound and binding between the two test agents in the presence and absence of the test compound is detected and/or measured. In such assays neither of the test agents need be detectably labeled. For example, by exploiting the phenomenon of surface plasmon resonance, the MUC1 test agent can be bound to a suitable solid substrate and the MUC1-binder test agent exposed to the substrate-bound MUC1 test agent in the presence and absence of the compound of interest. Binding of the MUC1-binder test agent to the MUC1 test agent on the solid substrate results in a change in the intensity of surface plasmon resonance that can be detected qualitatively or quantitatively by an appropriate instrument, e.g., a Biacore apparatus (Biacore International AB, Rapsgatan, Sweden). It will be appreciated that the experiment can be performed in reverse, i.e., with the MUC1-binder test agent bound to the solid substrate and the MUC1 test agent added to it in the presence of the test compound.

Moreover, assays to test for inhibition or enhancement of binding to MUC1 can involve the use, for example, of: (a) a single MUC1-specific "detection" antibody that is detectably labeled; (b) an unlabeled MUC1-specific antibody and a detectably labeled secondary antibody; or (c) a biotinylated MUC1-specific antibody and detectably labeled avidin. In addition, combinations of these approaches (including "multi-layer" assays) familiar to those in the art can be used to enhance the sensitivity of assays. In these assays, the MUC1-binder test agent can be immobilized on a solid substrate such as a nylon or nitrocellulose membrane by, for example, "spotting" an aliquot of a sample containing the test agent onto a membrane or by blotting onto a membrane an electrophoretic gel on which the sample or an aliquot of the sample has been subjected to electrophoretic separation. Alternatively, the MUC1-binder test agent can be bound to a plastic substrate (e.g., the plastic bottom of an ELISA (enzyme-linked immunosorbent assay) plate well) using methods known in the art. The substrate-bound test agent is then exposed to the MUC1 test agent in the presence and absence of the test compound. After incubating the resulting mixture for a period of time and at temperature optimized for the system of interest, the presence and/or amount of MUC1 test agent bound to the MUC1-binder test on the solid substrate is then assayed using a detection antibody that binds to the MUC1 test agent and, where required, appropriate detectably labeled secondary antibodies or avidin. It will be appreciated that instead of binding the MUC1-binder test agent to the solid substrate, the MUC1 test agent can be bound to it. In this case binding of the MUC1-binder test agent to the substrate-bound MUC1 is tested by obvious adaptions of the method described above for substrate-bound MUC1-binder test agent.

The invention also features "sandwich" assays. In these sandwich assays, instead of immobilizing test agents on solid substrates by the methods described above, an appropriate test agent can be immobilized on the solid substrate by, prior to exposing the solid substrate to the test agent, conjugating a "capture" test agent-specific antibody (polyclonal or mAb) to the solid substrate by any of a variety of methods known in the art. The test agent is then bound to the solid substrate by virtue of its binding to the capture antibody conjugated to the solid substrate. The procedure is carried out in essentially the same manner described above for methods in which the appropriate test agent is bound to the solid substrate by techniques not involving the use of a capture antibody. It is understood that in these sandwich assays, the capture antibody should not bind to the same epitope (or range of epitopes in the case of a polyclonal antibody) as the detection antibody. Thus, if a mAb is used as a capture antibody, the detection antibody can be either: (a) another mAb that binds to an epitope that is either completely physically separated from or only partially overlaps with the epitope to which the capture mAb binds; or (b) a polyclonal antibody that binds to epitopes other than or in addition to that to which the capture mAb binds. On the other hand, if a polyclonal antibody is used as a capture antibody, the detection antibody can be either (a) a mAb that binds to an epitope that is either completely physically separated from or partially overlaps with any of the epitopes to which the capture polyclonal antibody binds; or (b) a polyclonal antibody that binds to epitopes other than or in addition to that to which the capture polyclonal antibody binds. Assays which involve the use of a capture and a detection antibody include sandwich ELISA assays, sandwich Western blotting assays, and sandwich immunomagnetic detection assays.

Suitable solid substrates to which the capture antibody can be bound include, without limitation, the plastic bottoms and sides of wells of microtiter plates, membranes such as nylon or nitrocellulose membranes, polymeric (e.g., without limitation, agarose, cellulose, or polyacrylamide) beads or particles.

Methods of detecting and/or for quantifying a detectable label depend on the nature of the label and are known in the art. Appropriate labels include, without limitation, radionuclides (e.g., $^{125}$I, $^{131}$I, $^{35}$S, $^{3}$H, $^{32}$P, or $^{14}$C), fluorescent moieties (e.g., fluorescein, rhodamine, or phycoerythrin), luminescent moieties (e.g., Qdot™ nanoparticles supplied by the Quantum Dot Corporation, Palo Alto, Calif.), compounds that absorb light of a defined wavelength, or enzymes (e.g., alkaline phosphatase or horseradish peroxidase). The products of reactions catalyzed by appropriate enzymes can be, without limitation, fluorescent, luminescent, or radioactive or they may absorb visible or ultraviolet light. Examples of detectors include, without limitation, x-ray film, radioactivity counters, scintillation counters, spectrophotometers, calorimeters, fluorometers, luminometers, and densitometers.

Candidate compounds can also be tested for their ability to inhibit or enhance binding of MUC1 to a MUC1-binder in cells. The cells can either naturally express an appropriate MUC1 test agent and/or MUC1-binder test agent of interest or they can recombinantly express either or both test agents. The cells can be normal or malignant and of any histological type, e.g., without limitation, epithelial cells, fibroblasts, lymphoid cells, macrophages/monocytes, granulocytes, keratinocytes, or muscle cells. Suitable cell lines include those recited in the examples, e.g., breast cancer or colon cancer cell lines. The test compound can be added to the solution (e.g., culture medium) containing the cells or, where the compound is a protein, the cells can recombinantly express it. The cells can optionally also be exposed to a stimulus of interest (e.g., a growth factor such as EGF) prior to or after exposure of the cells to the compound. Following incubation of cells expressing the test agents of interest in the absence or presence (optionally at various concentrations), physical association between the test agents can be determined microscopically using appropriately labeled antibodies specific for both test agents, e.g., by confocal microscopy. Alternatively, the cells can be lysed under non-dissociating conditions and the lysates tested for the presence of physically associated test agents. Such methods include adaptions of those described using isolated test agents. For example, an antibody specific for one of the two test agents (test agent 1) can be bound to a solid substrate (e.g., the bottom and sides of the well of a microtiter plate or a nylon membrane). After washing away unbound antibody, the solid substrate with bound antibody is contacted with the cell lysate. Any test agent 1 in the lysate, bound or not bound to the second test agent (test agent 2), will bind to the antibody specific for test agent 1 on the solid substrate. After washing away unbound lysate components, the presence of test agent 2 (bound via test agent 1 and the antibody specific for test agent 1 to the solid substrate) is tested for using a detectably labeled antibody (see above) specific for test agent 2. Alternatively, test agent 1 can be immunoprecipitated with an antibody specific for test agent 1 and the immunoprecipitated material can be subjected to electrophoretic separation (e.g., by polyacrylamide gel electrophoresis performed under non-dissociating conditions). The electrophoretic gel can then be blotted onto a membrane (e.g., a nylon or a nitrocellulose membrane) and any test agent 2 on the membrane detected and/or measured with a detectably labeled antibody (see above) specific for test agent 2 by any of the above-described methods. It is understood that in the above-described assays, test agent 1 can be either the MUC1 test agent or the MUC1-binder test agent or vice versa.

Methods of Designing and Producing Inhibitory Compounds

The invention also relates to using MUC1 test agents and/or MUC1-binder test agents to predict or design compounds that can interact with MUC1 and/or MUC1-binders and potentially thereby inhibit the ability of MUC1 to interact with an appropriate tumor progressor. One of skill in the art would know how to use standard molecular modeling or other techniques to identify small molecules that would bind to "appropriate sites" on MUC1 and/or tumor progressors. One such example is provided in Broughton (1997) Curr. Opin. Chem. Biol. 1, 392-398. Generally, an "appropriate site" on a MUC1 or MUC1-binder is a site directly involved in the physical interaction between the two molecule types. However, an "appropriate site" can also be an allosteric site, i.e., a region of the molecule not directly involved in a physical interaction with another molecule (and possibly even remote from such a "physical interaction" site) but to which binding of a compound results (e.g., by the induction in a conformational change in the molecule) in inhibition of the binding of the molecule to another molecule By "molecular modeling" is meant quantitative and/or qualitative analysis of the structure and function of protein-protein physical interaction based on three-dimensional structural information and protein-protein interaction models. This includes conventional numeric-based molecular dynamic and energy minimization models, interactive computer graphic models, modified molecular mechanics models, distance geometry and other structure-based constraint models. Molecular modeling typically is performed using a computer and may be further optimized using known methods.

Methods of designing compounds that bind specifically (e.g., with high affinity) to the region of MUC1 that interacts with p53 (i.e., the cytoplasmic domain of MUC1) or the region of p53 that binds to MUC1 (i.e., the C-terminal regulatory domain of p53) typically are also computer-based, and involve the use of a computer having a program capable of generating an atomic model. Computer programs that use X-ray crystallography data are particularly useful for designing such compounds. Programs such as RasMol, for example, can be used to generate a three dimensional model of, e.g., the region of MUC1 that interacts with p53 or the region of p53 that binds to MUC1 and/or determine the structures involved in MUC1-p53 binding. Computer programs such as INSIGHT (Accelrys, Burlington, Mass.), GRASP (Anthony Nicholls, Columbia University), Dock (Molecular Design Institute, University of California at San Francisco), and Auto-Dock (Accelrys) allow for further manipulation and the ability to introduce new structures.

Compounds can be designed using, for example, computer hardware or software, or a combination of both. However, designing is preferably implemented in one or more computer programs executing on one or more programmable computers, each containing a processor and at least one input device. The computer(s) preferably also contain(s) a data storage system (including volatile and non-volatile memory and/or storage elements) and at least one output device. Program code is applied to input data to perform the functions described above and generate output information. The output information is applied to one or more output devices in a known fashion. The computer can be, for example, a personal computer, microcomputer, or work station of conventional design.

Each program is preferably implemented in a high level procedural or object oriented programming language to communicate with a computer system. However, the programs can be implemented in assembly or machine language, if desired. In any case, the language can be a compiled or interpreted language.

Each computer program is preferably stored on a storage media or device (e.g., ROM or magnetic diskette) readable by a general or special purpose programmable computer. The computer program serves to configure and operate the computer to perform the procedures described herein when the program is read by the computer. The method of the invention can also be implemented by means of a computer-readable storage medium, configured with a computer program, where the storage medium so configured causes a computer to operate in a specific and predefined manner to perform the functions described herein.

For example, the computer-requiring steps in a method of designing an immunogenic compound can involve:

(a) inputting into an input device, e.g., through a keyboard, a diskette, or a tape, data (e.g. atomic coordinates) that define the three-dimensional (3-D) structure of a first molecule (e.g., MUC1 or a part of MUC1) that binds to a second molecule (e.g., a MUC1-binder or a part thereof) or a molecular complex (e.g., MUC1, or a part thereof, bound to a MUC1-binder, or a part thereof), e.g., a region of MUC1 that interacts with p53 (i.e., the cytoplasmic domain of MUC1), the region of p53 that binds to MUC1 (i.e., the C-terminal regulatory domain of p53), or all or a part (e.g., the cytoplasmic domain) of MUC1 bound to all or a part (e.g., the regulatory domain) of p53; and (b) determining, using a processor, the 3-D structure (e.g., an atomic model) of: (i) the site on the first molecule involved in binding to the second molecule; or (ii) one or more sites on the molecular components of molecular complex of interaction between molecular components of the molecular complex.

From the information obtained in this way, one skilled in the art will be able to design and make inhibitory compounds (e.g., peptides, non-peptide small molecules, aptamers (e.g., nucleic acid aptamers) with the appropriate 3-D structure (see "Methods of Making Inhibitory Compounds and Proteins Useful for the Invention" below).

Moreover, if computer-usable 3-D data (e.g., x-ray crystallographic data) for a candidate compound are available, the following computer-based steps can be performed in conjunction with computer-based steps (a) and (b) described above:

(c) inputting into an input device, e.g., through a keyboard, a diskette, or a tape, data (e.g. atomic coordinates) that define the three-dimensional (3-D) structure of a candidate compound;

(d) determining, using a processor, the 3-D structure (e.g., an atomic model) of the candidate compound;

(e) determining, using the processor, whether the candidate compound binds to the site on the first molecule or the one or more sites on the molecular components of the molecular complex; and (f) identifying the candidate compound as compound that inhibits the interaction between the first and second molecule or the between the molecular components of the molecular complex.

The method can involve the additional step of outputting to an output device a model of the 3-D structure of the compound. In addition, the 3-D data of candidate compounds can be compared to a computer database of, for example, 3-D structures (e.g., of MUC1, the cytoplasmic domain of MUC1, p53, or the regulatory domain of p53) stored in a data storage system.

Compounds of the invention also may be interactively designed from structural information of the compounds described herein using other structure-based design/modeling techniques (see, e.g., Jackson (1997) *Seminars in Oncology* 24:L164-172; and Jones et al. (1996) *J. Med. Chem.* 39:904-917). Compounds and polypeptides of the invention also can be identified by, for example, identifying candidate compounds by computer modeling as fitting spatially and preferentially (i.e., with high affinity) into the appropriate acceptor sites on MUC1 or p53.

Candidate compounds identified as described above can then be tested in standard cellular or cell-free binding or binding inhibition assays familiar to those skilled in the art. Exemplary assays are described herein.

A candidate compound whose presence requires at least 2-fold (e.g., 4-fold, 6-fold, 10-fold, 100-fold, 1000-fold, 10,000 fold, or 100,000-fold) more of a given MUC1 test agent to achieve a defined arbitrary level of binding to a fixed amount of a MUC1-binder test agent than is achieved in the absence of the compound can be useful for inhibiting the interaction between MUC1 and the relevant MUC1-binder, and thus can be useful as a cancer therapeutic or prophylactic agent. Alternatively, a candidate compound whose presence requires at least 2-fold (e.g., 2-fold, 4-fold, 6-fold, 10-fold, 100-fold, 1000-fold, 10,000 fold, or 100,000-fold) more of a given MUC1-binder test agent to achieve a defined arbitrary level of binding to a fixed amount of a MUC1 test agent than is achieved in the absence of the compound can be useful for inhibiting the interaction between MUC1 and the relevant MUC1-binder, and thus can be useful as a cancer therapeutic or prophylactic agent.

The 3-D structure of biological macromolecules (e.g., proteins, nucleic acids, carbohydrates, and lipids) can be determined from data obtained by a variety of methodologies. These methodologies, which have been applied most effectively to the assessment of the 3-D structure of proteins, include: (a) x-ray crystallography; (b) nuclear magnetic resonance (NMR) spectroscopy; (c) analysis of physical distance constraints formed between defined sites on a macromolecule, e.g., intramolecular chemical crosslinks between residues on a protein (e.g., International Patent Application No. PCT/US00/14667, the disclosure of which is incorporated herein by reference in its entirety), and (d) molecular modeling methods based on a knowledge of the primary structure of a protein of interest, e.g., homology modeling techniques, threading algorithms, or ab initio structure modeling using computer programs such as MONSSTER (Modeling Of New Structures from Secondary and Tertiary Restraints) (see, e.g., International Application No. PCT/US99/11913, the disclosure of which is incorporated herein by reference in its entirety). Other molecular modeling techniques may also be employed in accordance with this invention [e.g., Cohen et al. (1990) J. Med. Chem. 33: 883-894; Navia et al (1992) Current Opinions in Structural Biology, 2, pp. 202-210, the disclosures of which are incorporated herein by reference in its entirety]. All these methods produce data that are amenable to computer analysis. Other spectroscopic methods that can also be useful in the method of the invention, but that do not currently provide atomic level structural detail about biomolecules, include circular dichroism and fluorescence and ultraviolet/visible light absorbance spectroscopy. A preferred method of analysis is x-ray crystallography. Descriptions of this procedure and of NMR spectroscopy are provided below.

X-Ray Crystallography

X-ray crystallography is based on the diffraction of x-radiation of a characteristic wavelength by electron clouds surrounding the atomic nuclei in a crystal of a molecule or molecular complex of interest. The technique uses crystals of purified biological macromolecules or molecular complexes (but these frequently include solvent components, co-factors, substrates, or other ligands) to determine near atomic resolution of the atoms making up the particular biological macromolecule. A prerequisite for solving 3-D structure by x-ray crystallography is a well-ordered crystal that will diffract x-rays strongly. The method directs a beam of x-rays onto a regular, repeating array of many identical molecules so that the x-rays are diffracted from the array in a pattern from which the structure of an individual molecule can be retrieved. Well-ordered crystals of, for example, globular protein molecules are large, spherical or ellipsoidal objects with irregular surfaces. The crystals contain large channels between the individual molecules. These channels, which normally occupy more than one half the volume of the crystal, are filled with disordered solvent molecules, and the protein molecules are in contact with each other at only a few small regions. This is one reason why structures of proteins in crystals are generally the same as those of proteins in solution.

Methods of obtaining the proteins of interest are described below. The formation of crystals is dependent on a number of different parameters, including pH, temperature, the concentration of the biological macromolecule, the nature of the solvent and precipitant, as well as the presence of added ions or ligands of the protein. Many routine crystallization experiments may be needed to screen all these parameters for the combinations that give a crystal suitable for x-ray diffraction analysis. Crystallization robots can automate and speed up work of reproducibly setting up a large number of crystallization experiments (see, e.g., U.S. Pat. No. 5,790,421, the disclosure of which is incorporated herein by reference in its entirety).

Polypeptide crystallization occurs in solutions in which the polypeptide concentration exceeds it's solubility maximum (i.e., the polypeptide solution is supersaturated). Such solutions may be restored to equilibrium by reducing the polypeptide concentration, preferably through precipitation of the polypeptide crystals. Often polypeptides may be induced to crystallize from supersaturated solutions by adding agents that alter the polypeptide surface charges or perturb the interaction between the polypeptide and bulk water to promote associations that lead to crystallization.

Crystallizations are generally carried out between 4° C. and 20° C. Substances known as "precipitants" are often used to decrease the solubility of the polypeptide in a concentrated solution by forming an energetically unfavorable precipitating depleted layer around the polypeptide molecules [Weber (1991) Advances in Protein Chemistry, 41:1-36]. In addition to precipitants, other materials are sometimes added to the polypeptide crystallization solution. These include buffers to adjust the pH of the solution and salts to reduce the solubility of the polypeptide. Various precipitants are known in the art and include the following: ethanol, 3-ethyl-2-4 pentanediol, and many of the polyglycols, such as polyethylene glycol (PEG). The precipitating solutions can include, for example, 13-24% PEG 4000, 5-41% ammonium sulfate, and 1.0-1.5 M sodium chloride, and a pH ranging from 5-7.5. Other additives can include 0.1 M Hepes, 2-4% butanol, 0.1 M or 20 mM sodium acetate, 50-70 mM citric acid, 120-130 mM sodium phosphate, 1 mM ethylene diamine tetraacetic acid (EDTA), and 1 mM dithiothreitol (DTT). These agents are prepared in buffers and are added dropwise in various combinations to the crystallization buffer.

Commonly used polypeptide crystallization methods include the following techniques: batch, hanging drop, seed initiation, and dialysis. In each of these methods, it is important to promote continued crystallization after nucleation by maintaining a supersaturated solution. In the batch method, polypeptide is mixed with precipitants to achieve supersaturation, and the vessel is sealed and set aside until crystals appear. In the dialysis method, polypeptide is retained in a sealed dialysis membrane that is placed into a solution containing precipitant. Equilibration across the membrane increases the polypeptide and precipitant concentrations, thereby causing the polypeptide to reach supersaturation levels.

In the preferred hanging drop technique [McPherson (1976) J. Biol. Chem., 251:6300-6306], an initial polypeptide mixture is created by adding a precipitant to a concentrated polypeptide solution. The concentrations of the polypeptide and precipitants are such that in this initial form, the polypeptide does not crystallize. A small drop of this mixture is placed on a glass slide that is inverted and suspended over a reservoir of a second solution. The system is then sealed. Typically, the second solution contains a higher concentration of precipitant or other dehydrating agent. The difference in the precipitant concentrations causes the protein solution to have a higher vapor pressure than the second solution. Since the system containing the two solutions is sealed, an equilibrium is established, and water from the polypeptide mixture transfers to the second solution. This equilibrium increases the polypeptide and precipitant concentration in the polypeptide solution. At the critical concentration of polypeptide and precipitant, a crystal of the polypeptide may form.

Another method of crystallization introduces a nucleation site into a concentrated polypeptide solution. Generally, a concentrated polypeptide solution is prepared and a seed crystal of the polypeptide is introduced into this solution. If the concentrations of the polypeptide and any precipitants are correct, the seed crystal will provide a nucleation site around which a larger crystal forms.

Yet another method of crystallization is an electrocrystallization method in which use is made of the dipole moments of protein macromolecules that self-align in the Helmholtz layer adjacent to an electrode (see, e.g., U.S. Pat. No. 5,597,457, the disclosure of which is incorporated herein by reference in its entirety).

Some proteins may be recalcitrant to crystallization. However, several techniques are available to the skilled artisan to induce crystallization. For example, the removal of flexible polypeptide segments at the amino or carboxyl terminal end of the protein may facilitate production of crystalline protein samples. Removal of such segments can be done using molecular biology techniques or treatment of the protein with proteases such as trypsin, chymotrypsin, or subtilisin.

In diffraction experiments, a narrow and parallel beam of x-rays is taken from the x-ray source and directed onto the crystal to produce diffracted beams. The incident primary beams cause damage to both the macromolecule and solvent molecules. The crystal is, therefore, cooled (e.g., to −220° C. to −50° C.) to prolong its lifetime. The primary beam must strike the crystal from many directions to produce all possible diffraction spots, so the crystal is rotated in the beam during the experiment. The diffracted spots are recorded on a film or by an electronic detector. Exposed film has to be digitized and quantified in a scanning device, whereas the electronic detectors feed the signals they detect directly into a computer. Electronic area detectors significantly reduce the time required to collect and measure diffraction data. Each diffraction beam, which is recorded as a spot on film, is defined by three properties: the amplitude, which is measured from the intensity of the spot; the wavelength, which is set by the x-ray source; and the phase, which is lost in x-ray experiments. All three properties are needed for all of the diffracted beams in order to determine the positions of the atoms giving rise to the diffracted beams. One way of determining the phases is called Multiple Isomorphous Replacement (MIR), which requires the introduction of exogenous x-ray scatterers (e.g., heavy atoms such metal atoms) into the unit cell of the crystal. For a more detailed description of MIR, see U.S. Pat. No. 6,093,573 (column 15) the disclosure of which is incorporated herein by reference in its entirety.

Atomic coordinates refer to Cartesian coordinates (x, y, and z positions) derived from mathematical equations involving Fourier synthesis of data derived from patterns obtained via diffraction of a monochromatic beam of x-rays by the atoms (scattering centers) of biological macromolecule of interest in crystal form. Diffraction data are used to calculate electron density maps of repeating units in the crystal (unit cell). Electron density maps are used to establish the positions (atomic coordinates) of individual atoms within a crystal's unit cell. The absolute values of atomic coordinates convey spatial relationships between atoms because the absolute values ascribed to atomic coordinates can be changed by rotational and/or translational movement along x, y, and/or z axes, together or separately, while maintaining the same relative spatial relationships among atoms. Thus, a biological macromolecule (e.g., a protein) whose set of absolute atomic coordinate values can be rotationally or translationally adjusted to coincide with a set of prior determined values from an analysis of another sample is considered to have the same atomic coordinates as those obtained from the other sample.

Further details on x-ray crystallography can be obtained from co-pending U.S. application Ser. No. 10/486,278, U.S. Pat. No. 6,093,573 and International Application Nos. PCT/US99/18441, PCT/US99/11913, and PCT/US00/03745. The disclosures of all these patent documents are incorporated herein by reference in their entirety.

NMR Spectroscopy

While x-ray crystallography requires single crystals of a macromolecule of interest, NMR measurements are carried out in solution under near physiological conditions. However, NMR-derived structures are not as detailed as crystal-derived structures.

While the use of NMR spectroscopy was until relatively recently limited to the elucidation of the 3-D structure of relatively small molecules (e.g., proteins of 100-150 amino acid residues), recent advances including isotopic labeling of the molecule of interest and transverse relaxation-optimized spectroscopy (TROSY) have allowed the methodology to be extended to the analysis of much larger molecules, e.g., proteins with a molecular weight of 110 kDa [Wider (2000) BioTechniques, 29:1278-1294].

NMR uses radio-frequency radiation to examine the environment of magnetic atomic nuclei in a homogeneous magnetic field pulsed with a specific radio frequency. The pulses perturb the nuclear magnetization of those atoms with nuclei of nonzero spin. Transient time domain signals are detected as the system returns to equilibrium. Fourier transformation of the transient signal into a frequency domain yields a one-dimensional NMR spectrum. Peaks in these spectra represent chemical shifts of the various active nuclei. The chemical shift of an atom is determined by its local electronic environment. Two-dimensional NMR experiments can provide information about the proximity of various atoms in the structure and in three dimensional space. Protein structures can be determined by performing a number of two- (and sometimes 3- or 4-) dimensional NMR experiments and using the resulting information as constraints in a series of protein folding simulations.

More information on NMR spectroscopy including detailed descriptions of how raw data obtained from an NMR experiment can be used to determine the 3-D structure of a macromolecule can be found in: Protein NMR Spectroscopy, Principles and Practice, J. Cavanagh et al., Academic Press, San Diego, 1996; Gronenborn et al. (1990) Anal. Chem. 62(1):2-15; and Wider (2000), supra., the disclosures of all of which are incorporated herein by reference in their entirety Any available method can be used to construct a 3-D model of a region of MUC1 and/or a MUC1-binder of interest from the x-ray crystallographic and/or NMR data using a computer as described above. Such a model can be constructed from analytical data points inputted into the computer by an input device and by means of a processor using known software packages, e.g., HKL, MOSFILM, XDS, CCP4, SHARP, PHASES, HEAVY, XPLOR, TNT, NMRCOMPASS, NMRPIPE, DIANA, NMRDRAW, FELIX, VNMR, MADIGRAS, QUANTA, BUSTER, SOLVE, 0, FRODO, or CHAIN. The model constructed from these data can be visualized via an output device of a computer, using available systems, e.g., Silicon Graphics, Evans and Sutherland, SUN, Hewlett Packard, Apple Macintosh, DEC, IBM, or Compaq.

Methods of Making Inhibitory Compounds and Proteins Useful for the Invention

Once the 3-D structure of a protein of interest (MUC1, p53, or TBP), or a binding region-containing fragment thereof, has been established using any of the above methods, a compound that has substantially the same 3-D structure (or contains a domain that has substantially the same structure) as the binding region of the protein of interest. The compound's structure can be based on the 3-D structure of binding site of the parent protein (e.g., MUC1), the 3-D structure of the complementary acceptor site of the protein to which the parent protein binds (e.g., p53), or a combination of both. In this context, "has substantially the same 3-D structure" means that the compound binds with at least the same avidity as the parent protein to the non-parent partner. The compound can also bind to the non-parent partner with at least two-fold (at least: three-fold; four-fold; five-fold; six-fold; seven-fold; eight-fold; nine-fold; ten-fold; 20-fold; 50-fold; 100-fold; 1,000-fold; 10,000-fold; 100,000-fold; 1,000,000-fold; or even higher-fold) greater avidity than the parent protein. One of skill in the art would know how to test a compound for such an ability.

With the above described 3-D structural data on hand and knowing the chemical structure (e.g., amino acid sequence in the case of a protein) of the protein region of interest, those of skill in the art would know how to make compounds with the above-described properties. Such methods include chemical synthetic methods and, in the case of proteins, recombinant methods (see above). For example, cysteine residues appropriately placed in a compound so as to form disulfide bonds can be used to constrain the compound or a domain of the compound in an appropriate 3-D structure. In addition, in a compound that is a polypeptide or includes a domain that is a polypeptide, one of skill in the art would know what amino acids to include and in what sequence to include them in order to generate, for example, $\alpha$-helices, $\beta$ structures, or sharp turns or bends in the polypeptide backbone.

Of particular interest as small molecule compounds are nucleic acid aptamers which are relatively short nucleic acid (DNA, RNA or a combination of both) sequences that bind with high avidity to a variety of proteins and inhibit the binding to such proteins of ligands, receptors, and other molecules. Aptamers are generally about 25-40 nucleotides in length and have molecular weights in the range of about 18-25 kDa. Aptamers with high specificity and affinity for targets can be obtained by an in vitro evolutionary process termed SELEX (systemic evolution of ligands by exponential enrichment) [see, for example, Zhang et al. (2004) Arch. Immunol. Ther. Exp. 52:307-315, the disclosure of which is incorporated herein by reference in its entirety]. For methods of enhancing the stability (by using nucleotide analogs, for example) and enhancing in vivo bioavailability (e.g., in vivo persistence in a subject's circulatory system) of nucleic acid aptamers see Zhang et al. (2004) and Brody et al. [(2000) Reviews in Molecular Biotechnology 74:5-13, the disclosure of which is incorporated herein by reference in its entirety].

While not essential, computer-based methods can be used to design the compounds of the invention. Appropriate computer programs include: LUDI (Biosym Technologies, Inc., San Diego, Calif.), Aladdin (Daylight Chemical Information Systems, Irvine, Calif.); and LEGEND [Nishibata et al. (1985) J. Med. Chem. 36(20):2921-2928].

The compounds of the invention can include, in addition, to the above described immunogenic domains, one or more domains that facilitate purification (e.g., poly-histidine sequences) or domains that serve to direct the compound to appropriate target cells (e.g., cancer cells), e.g., ligands or antibodies (including antibody fragments such as Fab, F(ab')$_2$, or single chain Fv fragments) specific for cell surface components of target cells of the immune system, e.g., MUC1, Her2/Neu, or any of a variety of other tumor-associated antigens (TAA). Signal sequences that facilitate transport of the compounds across biological membranes (e.g., cell membranes and/or nuclear membranes) and/direct them to subcellular compartments can also be linked (e.g., covalently) to the compounds. Signal sequences are described in detail in U.S. Pat. No. 5,827,516, the disclosure of which is incorporated herein by reference in its entirety. All that is required in such multidomain compounds is that the domain corresponding to the parent inhibitory compound substantially retains the 3-D structure it would have in the absence of the additional domains. Conjugation to make such multidomain compounds can be by chemical methods [e.g., Barrios et al. (1992) Eur. J. Immunol. 22:1365-1372, the disclosure of which is incorporated herein by reference in its entirety]. Where the compound is a peptide, it can be produced as part of a recombinant protein, such as one that self-assembles into virus-sized particles (e.g., U.S. Pat. No. 4,918,166, the disclosure of which is incorporated herein by reference in its entirety) that display candidate binding peptides on the surface.

Compounds of the invention that are peptides also include those described above, but modified for in vivo use by the addition, at the amino- and/or carboxyl-terminal ends, of a blocking agent to facilitate survival of the relevant polypeptide in vivo. This can be useful in those situations in which the peptide termini tend to be degraded by proteases prior to cellular uptake. Such blocking agents can include, without limitation, additional related or unrelated peptide sequences that can be attached to the amino and/or carboxyl terminal residues of the peptide to be administered. This can be done either chemically during the synthesis of the peptide or by recombinant DNA technology by methods familiar to artisans of average skill.

Alternatively, blocking agents such as pyroglutamic acid or other molecules known in the art can be attached to the amino and/or carboxyl terminal residues, or the amino group at the amino terminus or carboxyl group at the carboxyl terminus can be replaced with a different moiety. Likewise, the peptide compounds can be covalently or noncovalently coupled to pharmaceutically acceptable "carrier" proteins prior to administration.

Also of interest are peptidomimetic compounds that are designed based upon the amino acid sequences of compounds of the invention that are peptides. Peptidomimetic compounds are synthetic compounds having a three-dimensional conformation (i.e., a "peptide motif") that is substantially the same as the three-dimensional conformation of a selected peptide. The peptide motif provides the peptidomimetic compound with the ability to inhibit the interaction between MUC1 and a MUC1-binder. Peptidomimetic compounds can have additional characteristics that enhance their in vivo utility, such as increased cell permeability and prolonged biological half-life. The peptidomimetics typically have a backbone that is partially or completely non-peptide, but with side groups that are identical to the side groups of the amino acid residues that occur in the peptide on which the peptidomimetic is based. Several types of chemical bonds, e.g., ester, thioester, thioamide, retroamide, reduced carbonyl, dimethylene and ketomethylene bonds, are known in the art to be generally useful substitutes for peptide bonds in the construction of protease-resistant peptidomimetics.

The proteins (MUC1, p53, or TBP) used for designing compounds of the invention can be purified from natural sources (e.g., from tissues such as pancreas, liver, lung, breast, skin, spleen, ovary, testis, muscle, joint tissue, neural tissue, gastrointestinal tissue or tumor tissue (e.g., breast cancer or colon cancer tissue), or body fluids such as blood, serum, or urine). Smaller peptides (fewer than 100 amino acids long) and other non-protein compounds of the invention can be conveniently synthesized by standard chemical means known to those in the art. In addition, both polypeptides and peptides can be manufactured by standard in vitro recombinant DNA techniques and in vivo transgenesis using nucleotide sequences encoding the appropriate polypeptides or peptides. Methods well-known to those skilled in the art can be used to construct expression vectors containing relevant coding sequences and appropriate transcriptional/translational control signals. See, for example, the techniques described in Sambrook et al., *Molecular Cloning: A Laboratory Manual* (2nd Ed.) [Cold Spring Harbor Laboratory, N.Y., 1989], and Ausubel et al., *Current Protocols in Molecular Biology* [Green Publishing Associates and Wiley Interscience, N.Y., 1989].

For the structural (e.g., x-ray crystallographic and NMR) analyses described above, it is generally required that proteins, or fragments thereof, be highly purified. Methods for purifying biological macromolecules (e.g., proteins) are known in the art. The degree of purity of proteins can be measured by any appropriate method, e.g., column chromatography, polyacrylamide gel electrophoresis, or HPLC analysis.

MUC1 and MUC1-binders used for the above analyses can be of any mammalian species, e.g., humans, non-human primates (e.g., monkeys, baboons, or chimpanzees), horses, cattle, pigs, sheep, goats, dogs, cats, rabbits, guinea pigs, gerbils, hamsters, rats, and mice.

Methods of Inhibiting Binding of MUC1 to a MUC1-Binder in a Cell

The invention features a method of inhibiting binding of MUC1 to a MUC1-binder (p53 and/or TBP) in a cell. The method involves introducing into the cell a compound that inhibits the binding of a tumor progressor to the MUC1 (e.g., to the MUC1 CD). Prior to introduction of the compound into the cell, the cell (or another cancer cell from the subject from which the cell to be treated was obtained) can optionally be tested for MUC1 expression. This can be done by testing for expression of either MUC1 protein or MUC1 mRNA by any of a wide variety of methods known in the art.

The compound can be one identified by the methods described above. Examples of appropriate compounds include the CD of human MUC1 (SEQ ID NO:2), peptide fragments of the CD of MUC1 that bind to MUC1-binders, and fragments of MUC1-binders that bind MUC1. An appropriate fragment of the CD of human MUC1 can be one containing or consisting of amino acids 9-46 (SEQ ID NO:4) of the human MUC1 CD (SEQ ID NO:2) (e.g., a peptide containing or consisting of amino acids 1-51 (SEQ ID NO:5) of MUC1-CD). Other useful inhibitory compounds can be molecules that contain or consist of all or part of amino acids 363-393 (SEQ ID NO:6) of human p53 (SEQ ID NO:1).

Peptide inhibitory compounds can contain up to 50 (e.g., one, two, three, four, five, six, seven, eight, nine, ten, 12, 15, 18, 20, 25, 30, 35, 40, 45, or 50) MUC1 or MUC1-binder residues or unrelated residues on either end or on both ends of the MUC1 or MUC1-binder inhibitory segments.

Any MUC1 or MUC1-binder peptides to be used as inhibitor compounds can optionally have any phosphorylation-susceptible amino acid residues phosphorylated.

MUC1 peptide fragments useful as inhibitory compounds (or other inhibitory compounds e.g., p53 or TBP-specific antibodies or antibody fragments) that act by binding to p53 or TBP) will have substantially no MUC1 agonist activity, i.e., they will substantially lack the effects of MUC1 described herein that result from binding of MUC1 C-ter to the p21 gene and Bax gene promoter. Compounds having substantially no MUC1 agonist activity are those having less than 20% (e.g., less than: 10%; 5%; 2%; 1%; 0.5%; 0.2%; 0.1%; 0.01%; 0.001%; or 0.0001%) of the ability of MUC1 C-ter to enhance transcription of the p21 gene or to decrease the transcription of the Bax gene in the presence of unlimiting amounts of p53.

Similarly p53 and TBP peptide fragment compounds will have substantially none of the transcription-enhancing activity of p53 on expression of the p21 gene or substantially none of the transcription-decreasing activity of TBP on the Bax gene, respectively, that occurs in the presence of unlimiting amounts of MUC1. Compounds having substantially none of the transcription-enhancing activity of p53 on expression of the p21 gene or substantially none of the transcription-decreasing activity of TBP on the Bax gene that occurs in the presence of unlimiting amounts of MUC1, have less than 20% (e.g., less than: 10%; 5%; 2%; 1%; 0.5%; 0.2%; 0.1%; 0.01%; 0.001%; or 0.0001%) of the ability of p53 to enhance transcription of the p21 gene or of the ability of TBP to decrease expression of the Bax gene, respectively, in the presence of unlimiting amounts of MUC1. Thus, peptide fragments of p53 and TBP useful as inhibitory compounds will generally lack all or part of their DNA-binding domains. Methods of designing, making, and testing such compounds for the appropriate binding-inhibitory activity are known to those in the art.

In addition, the inhibitory compounds can be antibodies, or antigen-binding antibody fragments, specific for MUC1, p53, or TBP. Such antibodies will generally bind to, or close to: (a) the region of MUC1 to which p53 or TBP binds; (b) or the region on p53 or the region on TBP to which MUC1 binds. However, as indicated above, the compounds can also act allosterically and so they can also bind to the three proteins at positions other than, and even remote from, the binding sites for MUC1 (on p53 and TBP) and on p53 or TBP (for MUC1). As used throughout the present application, the term "antibody" refers to a whole antibody (e.g., IgM, IgG, IgA, IgD, or IgE) molecule that is generated by any one of a variety of methods that are known in the art. The antibody can be made in or derived from any of a variety of species, e.g., humans, non-human primates (e.g., monkeys, baboons, or chimpanzees), horses, cattle, pigs, sheep, goats, dogs, cats, rabbits, guinea pigs, gerbils, hamsters, rats, and mice.

The antibody can be a purified or a recombinant antibody. Also useful for the invention are antibody fragments and chimeric antibodies and humanized antibodies made from non-human (e.g., mouse, rat, gerbil, or hamster) antibodies. As used herein, the term "antibody fragment" refers to an antigen-binding fragment, e.g., Fab, F(ab')$_2$, Fv, and single chain Fv (scFv) fragments. An scFv fragment is a single polypeptide chain that includes both the heavy and light chain variable regions of the antibody from which the scFv is derived. In addition, diabodies [Poljak (1994) Structure 2(12):1121-1123; Hudson et al. (1999) J. Immunol. Methods 23(1-2):177-189, the disclosures of both of which are incorporated herein by reference in their entirety] and intrabodies [Huston et al. (2001) Hum. Antibodies 10(3-4):127-142; Wheeler et al. (2003) Mol. Ther. 8(3):355-366; Stocks (2004) Drug Discov. Today 9(22): 960-966, the disclosures of all of which are incorporated herein by reference in their entirety] can be used in the methods of the invention.

Antibody fragments that contain the binding domain of the molecule can be generated by known techniques. For example: F(ab')$_2$ fragments can be produced by pepsin digestion of antibody molecules; and Fab fragments can be generated by reducing the disulfide bridges of F(ab')$_2$ fragments or by treating antibody molecules with papain and a reducing agent. See, e.g., National Institutes of Health, 1 *Current Protocols In Immunology*, Coligan et al., ed. 2.8, 2.10 (Wiley Interscience, 1991) the disclosure of which is incorporated herein by reference in their entirety. scFv fragments can be produced, for example, as described in U.S. Pat. No. 4,642, 334, the disclosure of which is incorporated herein by reference in its entirety.

Chimeric and humanized monoclonal antibodies can be produced by recombinant DNA techniques known in the art, for example, using methods described in Robinson et al., International Patent Publication PCT/US86/02269; Akira et al., European Patent Application 184,187; Taniguchi, European Patent Application 171,496; Morrison et al., European Patent Application 173,494; Neuberger et al., PCT Application WO 86/01533; Cabilly et al., U.S. Pat. No. 4,816,567; Cabilly et al., European Patent Application 125,023; Better et al. (1988) Science 240, 1041-43; Liu et al. (1987) J. Immunol. 139, 3521-26; Sun et al. (1987) PNAS 84, 214-18; Nishimura et al. (1987) Canc. Res. 47, 999-1005; Wood et al. (1985) Nature 314, 446-49; Shaw et al. (1988) J. Natl. Cancer Inst. 80, 1553-59; Morrison, (1985) Science 229, 1202-07; Oi et al. (1986) BioTechniques 4, 214; Winter, U.S. Pat. No. 5,225, 539; Jones et al. (1986) Nature 321, 552-25; Veroeyan et al. (1988) Science 239, 1534; and Beidler et al. (1988) J. Immunol. 141, 4053-60. The disclosures of all these articles and patent documents are incorporated herein by reference in their entirety.

Cells to which the method of the invention can be applied include generally any cell that expresses MUC1. Such cells include normal cells, such as any normal epithelial cell, or a cancer cell, whose proliferation it is desired to inhibit. An appropriate cancer cell can be a breast cancer, lung cancer, colon cancer, pancreatic cancer, renal cancer, stomach cancer, liver cancer, bone cancer, hematological cancer (e.g., leukemia or lymphoma), neural tissue cancer, melanoma, ovarian cancer, testicular cancer, prostate cancer, cervical cancer, vaginal cancer, or bladder cancer cell. In addition, the methods of the invention can be applied to a wide range of species, e.g., humans, non-human primates (e.g., monkeys, baboons, or chimpanzees), horses, cattle, pigs, sheep, goats, dogs, cats, rabbits, guinea pigs, gerbils, hamsters, rats, and mice.

The methods can be performed in vitro, in vivo, or ex vivo. In vitro application of appropriate compounds can be useful, for example, in basic scientific studies of tumor cell biology, e.g., studies on the mechanism of action of MUC1 and/or the MUC1-binders in promoting tumor cell growth, including survival. In addition, the compounds that are inhibitory can be used as "positive controls" in methods to identify additional compounds with inhibitory activity (see above). In such in vitro methods, cells expressing MUC1 and one or more of the MUC1-binders, can be incubated for various times with the inhibitory compound(s) at a variety of concentrations. Other incubation conditions known to those in art (e.g., temperature, or cell concentration) can also be varied. Inhibition of binding can be tested by methods such as those disclosed herein.

The methods of the invention will preferably be in vivo or ex vivo.

Compounds that inhibit binding between MUC1 and a MUC1-binder are generally useful as cancer cell (e.g., breast cancer cell) survival-inhibiting and/or cell cycle-arresting therapeutics or prophylactics. They can be administered to mammalian subjects (e.g., human breast cancer patients) alone or in conjunction with other drugs and/or radiotherapy.

The compounds can also be administered to subjects that are genetically and/or due to, for example, physiological and/or environmental factors, susceptible to cancer, e.g., subjects with a family history of cancer (e.g., breast cancer), subjects with chronic inflammation or subject to chronic stress, or subjects that are exposed to natural or non-natural environmental carcinogenic conditions (e.g., excessive exposure to sunlight, industrial carcinogens, or tobacco smoke). As used herein, a compound that is "therapeutic" is a compound that causes a complete abolishment of the symptoms of a disease or a decrease in the severity of the symptoms of the disease. "Prevention" means that symptoms of the disease (e.g., cancer) are essentially absent. As used herein, "prophylaxis" means complete prevention of the symptoms of a disease, a delay in onset of the symptoms of a disease, or a lessening in the severity of subsequently developed disease symptoms.

When the methods are applied to subjects with cancer, prior to administration of a compound, the cancer can optionally be tested for MUC1 expression (MUC1 protein or MUC1 mRNA expression) by methods known in the art. In this way, subjects can be identified as having a MUC1-expressing cancer. Such methods can be performed in vitro on cancer cells obtained from a subject. Alternatively, in vivo imaging techniques using, for example, radiolabeled antibodies specific for MUC1 can be performed. In addition, body fluids (e.g., blood or urine) from subjects with cancer can be tested for elevated levels of MUC1 protein or MUC1 protein fragments.

In Vivo Approaches

In one in vivo approach, a compound that inhibits binding of MUC1 to a MUC1-binder is administered to a subject. Generally, the compounds of the invention will be suspended in a pharmaceutically-acceptable carrier (e.g., physiological saline) and administered orally or injected intravenously, subcutaneously, intramuscularly, intrathecally, intraperitoneally, intrarectally, intravaginally, intranasally, intragastrically, intratracheally, or intrapulmonarily. They can also be delivered directly to tumor cells, e.g., to a tumor or a tumor bed following surgical excision of the tumor, in order to kill any remaining tumor cells. The dosage required depends on the choice of the route of administration; the nature of the formulation; the nature of the patient's illness; the subject's size, weight, surface area, age, and sex; other drugs being administered; and the judgment of the attending physician. Suitable dosages are in the range of 0.0001 mg/kg-100 mg/kg. Wide variations in the needed dosage are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization as is well understood in the art. Administrations can be single or multiple (e.g., 2-, 3-, 4-, 6-, 8-, 10-, 20-, 50-, 100-, 150-, or more fold). Encapsulation of the polypeptide in a suitable delivery vehicle (e.g., polymeric microparticles or implantable devices) may increase the efficiency of delivery, particularly for oral delivery.

Alternatively, where an inhibitory compound is a polypeptide, a polynucleotide containing a nucleic acid sequence encoding the polypeptide can be delivered to appropriate cells in a mammal. Expression of the coding sequence can be directed to any cell in the body of the subject. However, expression will preferably be directed to cells in the vicinity of the tumor cells whose proliferation it is desired to inhibit. Expression of the coding sequence can be directed to the tumor cells themselves. This can be achieved by, for example, the use of polymeric, biodegradable microparticle or microcapsule delivery devices known in the art.

Another way to achieve uptake of the nucleic acid is using liposomes, prepared by standard methods. The vectors can be incorporated alone into these delivery vehicles or co-incorporated with tissue-specific or tumor-specific antibodies. Alternatively, one can prepare a molecular conjugate composed of a plasmid or other vector attached to poly-L-lysine by electrostatic or covalent forces. Poly-L-lysine binds to a ligand that can bind to a receptor on target cells [Cristiano et al. (1995), J. Mol. Med. 73:479, the disclosure of which is incorporated herein by reference in its entirety]. Alternatively, tissue specific targeting can be achieved by the use of tissue-specific transcriptional regulatory elements (TRE) which are known in the art. Delivery of "naked DNA" (i.e., without a delivery vehicle) to an intramuscular, intradermal, or subcutaneous site is another means to achieve in vivo expression.

In the relevant polynucleotides (e.g., expression vectors), the nucleic acid sequence encoding the polypeptide of interest with an initiator methionine and optionally a targeting sequence is operatively linked to a promoter or enhancer-promoter combination. Short amino acid sequences can act as signals to direct proteins to specific intracellular compartments. Such signal sequences are described in detail in U.S. Pat. No. 5,827,516, the disclosure of which is incorporated herein by reference in its entirety.

Enhancers provide expression specificity in terms of time, location, and level. Unlike a promoter, an enhancer can function when located at variable distances from the transcription initiation site, provided a promoter is present. An enhancer can also be located downstream of the transcription initiation site. To bring a coding sequence under the control of a promoter, it is necessary to position the translation initiation site of the translational reading frame of the peptide or polypeptide between one and about fifty nucleotides downstream (3') of the promoter. Promoters of interest include but are not limited to the cytomegalovirus HCMV immediate early gene, the early or late promoters of SV40 adenovirus, the lac system, the trp system, the TAC system, the TRC system, the major operator and promoter regions of phage A, the control regions of fd coat protein, the promoter for 3-phosphoglycerate kinase, the promoters of acid phosphatase, and the promoters of the yeast α-mating factors, the adenoviral E1b minimal promoter, or the thymidine kinase minimal promoter. The DF3 enhancer can be particularly useful for expression of an inhibitory compound in cells that naturally express MUC1, for example, normal epithelial cells or malignant epithelial cells (carcinoma cells), e.g., breast cancer cells [see U.S. Pat. Nos. 5,565,334 and 5,874,415, the disclosures of which are incorporated herein by reference in their entirety]. The coding sequence of the expression vector is operatively linked to a transcription terminating region.

Suitable expression vectors include plasmids and viral vectors such as herpes viruses, retroviruses, vaccinia viruses, attenuated vaccinia viruses, canary pox viruses, adenoviruses and adeno-associated viruses, among others.

Polynucleotides can be administered in a pharmaceutically acceptable carrier. Pharmaceutically acceptable carriers are biologically compatible vehicles that are suitable for administration to a human, e.g., physiological saline or liposomes. A therapeutically effective amount is an amount of the polynucleotide that is capable of producing a medically desirable result (e.g., decreased proliferation of cancer cells) in a treated animal. As is well known in the medical arts, the dosage for any one patient depends upon many factors, including the patient's size, body surface area, age, the particular compound to be administered, sex, time and route of administration, general health, and other drugs being administered concurrently. Dosages will vary, but a preferred dosage for administration of polynucleotide is from approximately $10^6$ to approximately $10^{12}$ copies of the polynucleotide molecule. This dose can be repeatedly administered, as needed. Routes of administration can be any of those listed above.

Ex Vivo Approaches

An ex vivo strategy can involve transfecting or transducing cells obtained from the subject with a polynucleotide encoding a polypeptide that inhibit binding of MUC1 to a MUC1-binder. The transfected or transduced cells are then returned to the subject. The cells can be any of a wide range of types including, without limitation, hemopoietic cells (e.g., bone marrow cells, macrophages, monocytes, dendritic cells, T cells, or B cells), fibroblasts, epithelial cells, endothelial cells, keratinocytes, or muscle cells. Such cells act as a source of the inhibitory polypeptide for as long as they survive in the subject. Alternatively, tumor cells, preferably obtained from the subject but potentially from an individual other than the subject, can be transfected or transformed by a vector encoding the inhibitory polypeptide. The tumor cells, preferably treated with an agent (e.g., ionizing irradiation) that ablates their proliferative capacity, are then introduced into the patient, where they secrete the polypeptide.

The ex vivo methods include the steps of harvesting cells from a subject, culturing the cells, transducing them with an expression vector, and maintaining the cells under conditions suitable for expression of the polypeptide that inhibits inhibit binding of MUC1 to a MUC1-binder or phosphorylation of MUC1 by a MUC1-binder. These methods are known in the art of molecular biology. The transduction step is accomplished by any standard means used for ex vivo gene therapy, including calcium phosphate, lipofection, electroporation, viral infection, and biolistic gene transfer. Alternatively, liposomes or polymeric microparticles can be used. Cells that have been successfully transduced can be selected, for example, for expression of the coding sequence or of a drug resistance gene. The cells may then be lethally irradiated (if desired) and injected or implanted into the patient.

Methods of Inhibiting Expression of MUC1 or a MUC1-Binder in a Cell

Also included in the invention are methods of inhibiting expression of MUC1 in cells. The method involves introducing into a cell (a) an antisense oligonucleotide that hybridizes to a MUC1 transcript, the antisense oligonucleotide inhibiting expression of MUC1 in the cell or (b) a MUC1 small interference RNA (siRNA).

The cells and species to which these methods are applied are the same as those recited above in "Methods of Inhibiting Binding of MUC1 to a MUC1-binder in a Cell".

Prior to introduction of an antisense oligonucleotide into the cell, the cell (or another cancer cell from the subject from which the cell to be treated was obtained) can optionally be tested for expression of MUC1 as described above.

The antisense oligonucleotides hybridize to MUC1 transcripts and have the effect in the cell of inhibiting expression of MUC1. Inhibiting expression of MUC1 in a cell can inhibit cancer cell survival as well as other cancer-enhancing activities associated with MUC1 expression, e.g., cancer cell proliferation and defective adhesion of cancer cells to neighboring cells. The method can thus be applied to the therapy of cancer, including metastasis.

Antisense compounds are generally used to interfere with protein expression either by, for example, interfering directly with translation of a target mRNA molecule, by RNAse-H-mediated degradation of the target mRNA, by interference with 5' capping of mRNA, by prevention of translation factor binding to the target mRNA by masking of the 5' cap, or by inhibiting of mRNA polyadenylation. The interference with protein expression arises from the hybridization of the antisense compound with its target mRNA. A specific targeting site on a target mRNA of interest for interaction with a antisense compound is chosen. Thus, for example, for modulation of polyadenylation a preferred target site on an mRNA target is a polyadenylation signal or a polyadenylation site. For diminishing mRNA stability or degradation, destabilizing sequences are preferred target sites. Once one or more target sites have been identified, oligonucleotides are chosen which are sufficiently complementary to the target site (i.e., hybridize sufficiently well under physiological conditions and with sufficient specificity) to give the desired effect.

With respect to this invention, the term "oligonucleotide" refers to an oligomer or polymer of RNA, DNA, a combination of the two, or a mimetic of either. The term includes oligonucleotides composed of naturally-occurring nucleobases, sugars, and covalent internucleoside (backbone) linkages. The normal linkage or backbone of RNA and DNA is a 3' to 5' phosphodiester bond. The term also refers however to oligonucleotides composed entirely of, or having portions containing, non-naturally occurring components which function in a similar manner to the oligonucleotides containing only naturally-occurring components. Such modified substituted oligonucleotides are often preferred over native forms because of desirable properties such as, for example, enhanced cellular uptake, enhanced affinity for target sequence, and increased stability in the presence of nucleases. In the mimetics, the core base (pyrimidine or purine) structure is generally preserved but (1) the sugars are either modified or replaced with other components and/or (2) the inter-nucleobase linkages are modified. One class of nucleic acid mimetic that has proven to be very useful is referred to as protein nucleic acid (PNA). In PNA molecules the sugar backbone is replaced with an amide-containing backbone, in particular an aminoethylglycine backbone. The bases are retained and are bound directly to the aza nitrogen atoms of the amide portion of the backbone. PNA and other mimetics useful in the instant invention are described in detail in U.S. Pat. No. 6,210,289, the disclosure of which is incorporated herein by reference in its entirety.

The antisense oligomers to be used in the methods of the invention generally comprise about 8 to about 100 (e.g., about 14 to about 80 or about 14 to about 35) nucleobases (or nucleosides where the nucleobases are naturally occurring).

The antisense oligonucleotides can themselves be introduced into a cell or an expression vector containing a nucleic sequence (operably linked to a TRE) encoding the antisense oligonucleotide can be introduced into the cell. In the latter case, the oligonucleotide produced by the expression vector is an RNA oligonucleotide and the RNA oligonucleotide will be composed entirely of naturally occurring components.

The methods of the invention can be in vitro or in vivo. In vitro applications of the methods can be useful, for example, in basic scientific studies on cancer cell growth, survival, and metastasis. Moreover, since studies described herein show that inhibiting MUC1 expression resulted in enhanced activity of genotoxic chemotherapeutic agents, they can be used in screening, for example, genotoxic compounds for cancer chemotherapeutic efficacy. In such in vitro methods, appropriate cells (e.g., those expressing MUC1), can be incubated for various lengths of time with (a) the antisense oligonucleotides or (b) expression vectors containing nucleic acid sequences encoding the antisense oligonucleotides at a variety of concentrations. Other incubation conditions known to those in art (e.g., temperature or cell concentration) can also be varied.

Inhibition of MUC1 expression or cancer cell survival can be tested by methods known to those in the art, e.g., methods such as those disclosed herein. However, the methods of the invention will preferably be in vivo.

The antisense methods are generally useful for cancer cell (e.g., breast cancer cell) survival-inhibiting, proliferation-inhibiting, and/or mestastasis-inhibiting therapy. They can be administered to mammalian subjects (e.g., human breast cancer patients) alone or in conjunction with other drugs and/or radiotherapy. Prior to administration of an antisense oligonucleotide to a subject with cancer, the subject can be identified as having a cancer in which the cancer cells express MUC1. Methods for testing this are described above. Doses, formulations, routes of administration, vectors, and targeting are as described for in vivo approaches to inhibiting the binding of MUC1 to MUC-1-binders in a cell. Naturally, the antisense oligonucleotides and expression vectors containing nucleic acid sequences encoding the antisense oligonucleotides will preferably be targeted to cells whose survival and/or growth arrest it is desired to inhibit.

The invention also includes both in vivo and in vitro methods of inhibiting expression of MUC1 that involve the use of compounds (small interference (si)RNA or other small molecules) that inhibit transcription of the MUC1 gene and/or translation of MUC1 mRNA by non-antisense mechanisms. In vitro methods are essentially the same as those described above for antisense methods. In vivo methods involve administration to any of the subjects and by any of the doses and routes disclosed herein. Subjects will preferably be those with cancer, e.g., human cancer patients. Doses, formulations, routes of administration, vectors, and targeting are as described for in vivo antisense approaches. While the invention is not limited by any particular mechanism of action, such compounds can be those that act by either inhibiting the binding and/or the activity of transcription factors or by altering the stability of MUC1 mRNA.

Double-stranded small interference RNA (siRNA) homologous to MUC1 DNA can be used to reduce expression of MUC1 in cancer cells. See, e.g., Fire et al. (1998) Nature 391:806-811; Romano and Masino (1992) Mol. Microbiol. 6:3343-3353; Cogoni et al. (1996) EMBO J. 15:3153-3163; Cogoni and Masino (1999) Nature 399:166-169; Misquitta and Paterson (1999) Proc. Natl. Acad. Sci. USA 96:1451-1456; and Kennerdell and Carthew (1998) Cell 95:1017-1026. The disclosures of all these articles are incorporated herein by reference in their entirety.

The sense and anti-sense RNA strands of siRNA can be individually constructed using chemical synthesis and enzymatic ligation reactions using procedures known in the art. For example, each strand can be chemically synthesized using naturally occurring nucleotides or variously modified nucleotides designed to increase the biological stability of the molecule or to increase the physical stability of the duplex formed between the sense and anti-sense strands, e.g., phosphorothioate derivatives and acridine substituted nucleotides. Some of the nucleotides (e.g., the terminal (either terminus) one, two, three, or four nucleotides) can also be deoxyribonucleotides. The sense or anti-sense strand can also be produced biologically using an expression vector into which a target MUC1 sequence (full-length or a fragment) has been subcloned in a sense or anti-sense orientation. The sense and anti-sense RNA strands can be annealed in vitro before delivery of the dsRNA to cells. Alternatively, annealing can occur in vivo after the sense and anti-sense strands are sequentially delivered to tumor cells and/or tumor-infiltrating leukocytes.

Of interest are siRNA that target, for example, the MUC1 gene sequence 5'-AAGTTCAGTGCCCAGCTCTAC-3'

(SEQ ID NO:7). The sense strand of such a siRNA could have the sequence 5'-GUUCAGUGCCCAGCUCUACUU-3' (SEQ ID NO:8) or 5'-GUUCAGUGCCCAGCUCUACdTdT-3' (SEQ ID NO:9) and the antisense strand could have the sequence 5'-GUAGAGCUGGGCACUGAACUU-3' (SEQ ID NO:10) or 5'-GUAGAGCUGGGCACUGAACdTdT-3' (SEQ ID NO:11). Also useful is a siRNA containing the MUC1 sequence 5'-GGUACCAUCAAUGUCCACG-3' (sense strand; SEQ ID NO:12) and 5'-CGUGGACA-UUGAUGGUACC-3' (antisense strand; SEQ ID NO:13).

Double-stranded siRNA interference can also be achieved by introducing into cells (e.g. cancer cells) a polynucleotide from which sense and anti-sense RNAs can be transcribed under the direction of separate promoters, or a single RNA molecule containing both sense and anti-sense sequences can be transcribed under the direction of a single promoter.

In any of the above methods of inhibiting the interaction between MUC1 and a MUC1-binder and of inhibiting expression of MUC1, one or more agents (e.g., two, three, four, five, six, seven, eight, nine, ten, 11, 12, 15, 18, 20, 25, 30, 40, 50, 60, 70, 80, 100, or more) including, for example, inhibitory compounds, antisense oligonucleotides, siRNAi, drugs, aptamers, or other small molecules (or vectors encoding them), can be used.

The above in vivo and ex vivo methods of inhibiting interactions between MUC1 and MUC1-binders and inhibiting expression of MUC1 can be used in conjunction with any of a variety of other cancer therapeutic/prophylactic regimens (e.g., chemotherapeutic, radiotherapeutic, biotherapeutic/prophylactic, and immunotherapeutic/prophylactic regimens). Of particular interest are regimens involving genotoxic (DNA-damaging) agents. Such agents include various forms of ionizing and non-ionizing radiation and a variety of chemotherapeutic compounds.

Non-ionizing radiation includes, for example, ultra-violet (UV) radiation, infra-red (IR) radiation, microwaves, and electronic emissions. The radiation employed in the methods of the invention is preferably ionizing radiation. As used herein, "ionizing radiation" means radiation composed of particles or photons that have sufficient energy or can produce sufficient energy by atomic nuclear interactions to produce ionization (gain or loss of electrons) of an atom. Ionizing radiation thus includes, without limitation, α-radiation, β-radiation, γ-radiation, or x-radiation. A preferred radiation is x-radiation.

Ionizing radiation causes DNA damage and cell killing generally in proportion to the dose administered. It has been indicated that the multiple biological effects induced by ionizing radiation are due either to the direct interaction of the radiation with DNA or to the formation of free radical species which lead to damage of DNA. These effects include gene mutations, malignant transformation, and cell killing.

External and internal means for delivering ionizing radiation to a target tissue or cell are known in the art. External sources include β or γ sources or linear accelerators and the like. Alternatively, ionizing radiation may be delivered, for example, by administering a radiolabeled antibody that is capable of binding to a molecule expressed on the surface of a carcinoma (e.g., MUC1 or Her2/neu) to a subject, or by implantation of radiation-emitting pellets in or near the tumor (brachytherapy).

The amount of radiation (e.g., ionizing radiation) needed to kill a given cell generally depends upon the nature of the cell. As used herein, an "effective dose" of radiation means a dose of radiation that produces cell damage or death when given in conjunction with an adenoviral vector of the invention. Means of determining an effective dose are known in the art.

X-radiation dosages range from daily doses of 50 to 200 roentgens for prolonged periods of time (e.g., 6-8 weeks or even longer) to single doses of 2,000 to 6,000 roentgens. Dosages for administered radioisotopes vary widely, and depend on the half-life of the isotope, the strength and type of radiation emitted, and the degree of uptake by the target cells.

As used herein, "chemotherapeutic agents" are chemical compounds that enter cells and damage DNA. Thus, they can be compounds which, for example, directly cross-link DNA (e.g., cisplatin (CDDP) and other alkylating agents), intercalate into DNA, or interfere with DNA replication, mitosis, or chromosomal segregation, e.g., adriamycin (also known as doxorubicin), VP-16 (also known as etoposide), verampil, podophyllotoxin, and the like. These compounds are widely used in the treatment of carcinomas. Chemotherapeutic agents useful in the methods of the invention include, without limitation, cisplatin, carboplatin, procarbazine, mechlorethamine, cyclophosphamide, camptothecin, ifosfamide, melphalan, chlorambucil, bisulfan, nitrosurea, dactinomycin, daunorubicin, doxorubicin, bleomycin, plicomycin, mitomycin, etoposide, verampil, podophyllotoxin, tamoxifen, taxol, transplatinum, 5-fluorouracil, vincristin, vinblastin, methotrexate, or any analog or derivative of these that is effective in damaging DNA.

Routes of administration are the same as those disclosed herein for interaction-inhibiting and expression-inhibiting compounds. Doses and frequency of administration vary widely according to all the variables listed above for administration of interaction-inhibiting and expression-inhibiting compounds. For example, adriamycin can be administered by bolus intravenous injection at doses in the range of 25-75 mg/m$^2$ and etoposide can be administered intravenously or orally at doses in the range of 35-100 mg/m$^2$. Methods of determining optimal parameters of administration are well known in the art.

Combination treatments can include administration of one or more (e.g., one, two, three, four, five, six, seven, eight, nine or ten) interaction-inhibiting and/or expression-inhibiting compounds of the invention, and one or more (e.g., one, two, three, four, five, six, seven, eight, nine or ten) radiation modalities, and/or one or more (e.g., one, two, three, four, five, six, seven, eight, nine or ten) chemotherapeutic agents. The interaction-inhibiting and expression-inhibiting compounds, radiation treatments and chemotherapeutic agents can be given in any order and frequency. They can be given simultaneously or sequentially. Treatment with any one of the modalities (interaction-inhibiting and expression-inhibiting compounds, radiation, or chemotherapeutic agents) can involve single or multiple (e.g., two, three, four, five, six, eight, nine, ten, 12, 15, 20, 30, 40, 50, 60, 80, 100, 200, 300, 500, or more) administrations separated by any time period found to be optimal in terms of therapeutic benefit. Multiple administrations can be separated by one to 23 hours, a day, two, three days, four days, five days, six days, seven days, eight, ten days, twelve days, two weeks, three weeks four weeks, a month, two months, three months, four months, five months, six months, seven months, eight months, nine months, ten months, eleven months, a year, one and one half of a year, two years, three years, five years, or ten years. Administrations can be continued for as long as the subject is need of the treatment, e.g., any of the of the above time intervals, and can be for the life of the subject. Administrations can be, for example, once a week for the life-time of the subject. When administrations of any or all of the modalities are multiple, the course of any one can be simultaneous with, overlapping with, or consequent to the course(s) of the other (s).

The invention is illustrated, not limited, by the following examples.

EXAMPLES

Example 1

Materials and Methods

Cell culture. Human HCT116/vector cells (HCT116 human colon carcinoma cells stably transfected with a control vector), HCT116/MUC1 cells [HCT116 cells stably transfected with cDNA encoding human MUC1; Ren et al. (2002b) J. Biol. Chem. 277:17616-17622], HCT116/p53$^{-/-}$ cells [HCT116 cells in which both p53 alleles have been disrupted; Bunz et al. (1998) Science 282:1497-1501] and human MCF-7 breast cancer cells were grown in Dulbecco's modified Eagle's medium (DMEM) with 10% heat-inactivated fetal bovine serum (HI-FBS), antibiotics (100 μg/ml streptomycin and 100 units/ml penicillin) and 2 mM L-glutamine. Human ZR-75-1 breast carcinoma and human LNCaP prostate carcinoma cells were cultured in RPMI 1640 medium supplemented with 10% HI-FBS, antibiotics (as for DMEM) and L-glutamine. Human U2OS osteosarcoma cells were grown in Minimal Essential Medium (MEM) with 10% HI-FBS and antibiotics (as for DMEM). Cells were treated with cisplatin (CDDP; Sigma, St Louis, Mo.) or etoposide (Sigma).

Immunoblotting and immunoprecipitation. Cell lysates were prepared from subconfluent cells as previously described [Wei et al. (2003) J. Biol. Chem. 278:29288-29297]. Immunoblot analysis was performed with anti-p53 antibody (Ab-2, Ab-6; Oncogene Research Products, San Diego, Calif.), anti-MUC1 N-ter antibody [the DF3 monoclonal antibody that binds to the N-terminal segment of human MUC1; Kufe et al. (1984) Hybridoma 3:223-232], anti-MUC1 C-ter antibody (Ab-5 that binds to the C-terminal segment of human MUC1; Neomarkers, Freemont, Calif.), anti-β-actin antibody (Sigma), anti-Myc antibody (Ab-1; Oncogene Research Products), anti-Bax antibody antibody (Santa Cruz Biotechnology; Santa Cruz, Calif.) and anti-p21 (Santa Cruz Biotechnology). Lysates were subjected to immunoprecipitation with anti-p53 or anti-Myc antibody and the immune complexes were analyzed by immunoblotting.

Plasmid construction and transfection. MUC1-CD(1-72) (the cytoplasmic domain of human MUC1 consisting of the C-terminal 72 amino acids (i.e., the cytoplasmic domain) of human MUC1 and variants thereof (containing various deletions) were generated by PCR polymerase chain reaction) using the pIRESpuro2-MUC1 vector (containing full-length human MUC I-encoding cDNA as a template [Li et al. (2001a) J. Biol. Chem. 276:6061-6064]. To generate vectors expressing GST-MUC1-CD (the above described cytoplasmic domain of MUC1 fused to GST (glutathione S transferase)), the PCR products were digested with BamHI/NotI and cloned into corresponding sites of the pGEX-4T-3 vector. Transfections were performed in 60 mm tissue culture dishes using Fugene®-6 (Roche Applied Science, Indianapolis, Ind.) or, for the luciferase assays, in 24 well tissue culture plates using the calcium phosphate method (Invitrogen, Carlsbad, Calif.). Cells were transiently transfected with the p21 (2.4-kbp HindIII fragment)-Luc reporter [Ren et al. (2002a) J. Biol. Chem. 277:33758-33765] or the Bax gene promoter (370-bp SmaI/SacI fragment)-luciferase (Luc) reporter [Miyashita et al. (1995) Cell 80:293-299] and an internal control LacZ expression plasmid (pCMV-LacZ) [Wei et al. (2001) J. Biol. Chem. 276:16107-16112].

Luciferase assays were performed with the Luciferase Assay System (Promega Corporation, Madison, Wis.) at 40 h after transfection. Luciferase activity was normalized to that obtained for LacZ and presented as relative luciferase activity. HCT116/p53$^{-/-}$ cells were stably transfected with pIRES-puro-2 or pIRES-puro-2-MUC1 as described [Ren et al. (2004)].

GST pull-down assays. GST and GST fusion proteins were purified by binding to, and elution from, glutathione-agarose beads (Sigma). $^{35}$S-labeled p53 prepared in TNT® (in vitro transcription/translation) reactions (Promega Corporation) was incubated with GST or the GST fusion proteins for 90 min at 4° C. After washing, the adsorbed proteins were resolved by SDS-PAGE and analyzed by autoradiography or Coomassie blue staining.

Chromatin immunoprecipitation (ChIP) and Repeat ChIP (Re-ChIP) assays. ChIP assays were performed as previously described [Shang et al. (2000) Cell 103:843-852] using anti-MUC1 C-ter antibody, anti-p53 antibody (Ab-6; Oncogene Research Products), anti-CBP antibody (C-1; Santa Cruz Biotechnology), anti-HDAC1 antibody (Upstate Biotechnology Inc., Waltham, Mass.), anti-Ac-H4 (Upstate Biotechnology Inc.), anti-TBP antibody (58C9; Santa Cruz Biotechnology), anti-TFIIB antibody (IIB8; Santa Cruz Biotechnology), or anti-TAFII250 antibody (6B3; Santa Cruz Biotechnology). For PCR, 2 μl from a 50 μl DNA extraction were used with 30-38 cycles of amplification. The primers for the p21 gene promoter p53-responsive elements (p53RE1 and p53RE2) have been previously described [Liu et al. (2003) J. Biol. Chem. 277:17557-17565]. The primers for the p21 gene control region (CR) were (forward: 5'-GGTGCTTCTGG-GAGAGGTGAC-3' (SEQ ID NO:14); reverse 5'-TGAC-CCACTCTGGCAGGCAAG-3' (SEQ ID NO:15)) and the p21 gene PP were (forward: 5'-GGAAGTGCCCTCCTG-CAGCAC-3' (SEQ ID NO:16); reverse: 5'-CGGCGAATC-CGCGCCCAGCTC-3' (SEQ ID NO:17)). Primers used for the Bax gene promoter p53RE were (forward: 5'-GAT-TGGGCCACTGCACTCCAG-3' (SEQ ID NO:18); reverse: 5'-TGACTAAAAACTGAGTGG-3' (SEQ ID NO:19)), Bax gene control region (CR) were (forward: 5'-CCTGCTGATC-TATCAGCACAG-3' (SEQ ID NO:20); reverse: 5'-GCTG-GTCTCTGAACTCCCAGA-3' (SEQ ID NO:21)) and the Bax gene PP were (forward: 5'-CGTGGGCTATATTGCTA-GATC-3' (SEQ ID NO:22); reverse: 5'-GTCCAATCG-CAGCTCTAATGC-3' (SEQ ID NO:23)).

For Re-ChIP assays, complexes from the primary ChIP were eluted with 10 mM DTT for 30 min at 37° C. and the eluates were diluted 20 times with Re-ChIP buffer (20 mM Tris-HCl, pH 8.1, 1% Triton X-100, 2 mM EDTA, 150 mM NaCl), reimmunoprecipitated with the indicated second antibodies, and resubjected to an appropriate PCR procedure.

Flow cytometry. Cells were fixed with 80% ice-cold ethanol, incubated in phosphate buffered saline (PBS) containing 30 μg/ml RNase (Roche Applied Science) for 60 min at 37° C. and then stained with propidium iodide (Sigma) for 30 min at room temperature in the dark. DNA content was analyzed by flow cytometry (Coulter EPICS XL-MCL; Miami, Fla.).

Colony formation assays. Aliquots containing 500 cells were plated into individual wells of 6-well culture plates containing 2 ml/well complete medium and incubated for 18-24 h at 37° C. The cells were treated with CDDP or etoposide for 12-48 h, washed and incubated for 8 d. Resulting colonies were stained with crystal violet and counted manually.

Apoptosis assays. Apoptotic cells were quantitated by analysis of sub-G1 DNA and propidium iodide staining as described [Ren et al. (2004) Cancer Cell 5:163-175].

Downregulation of p53. ZR-75-1/vector cells (ZR-75-1 breast cancer cells stably transfected with a control vector) and ZR-75-1/MUC1siRNA cells (ZR-75-1 cells stably transfected with cDNA transcription of which results in MUC1 siRNA) were seeded ($5 \times 10^5$/well) on 6-well plates. After 24 h, the cells were infected with a control empty adenovirus or one expressing human p53 siRNA ($2 \times 10^9$ Ad.p53siRNA particles/well; IMGENEX, San Diego, Calif.). The cells were incubated for 48-72 h and then harvested for analysis.

Example 2

MUC1 Associates with p53 in Cells

Figure 1C:
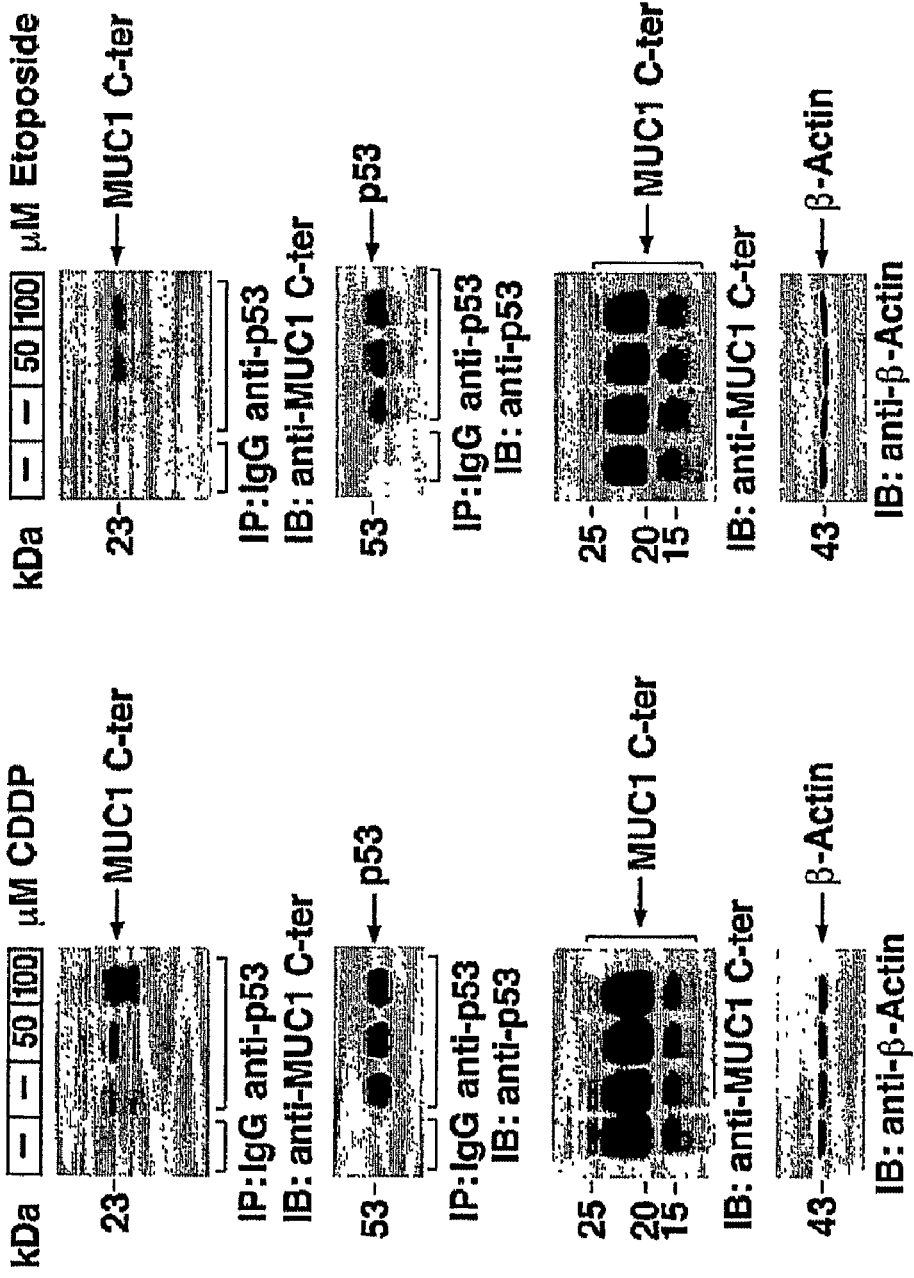
Figure 2B:
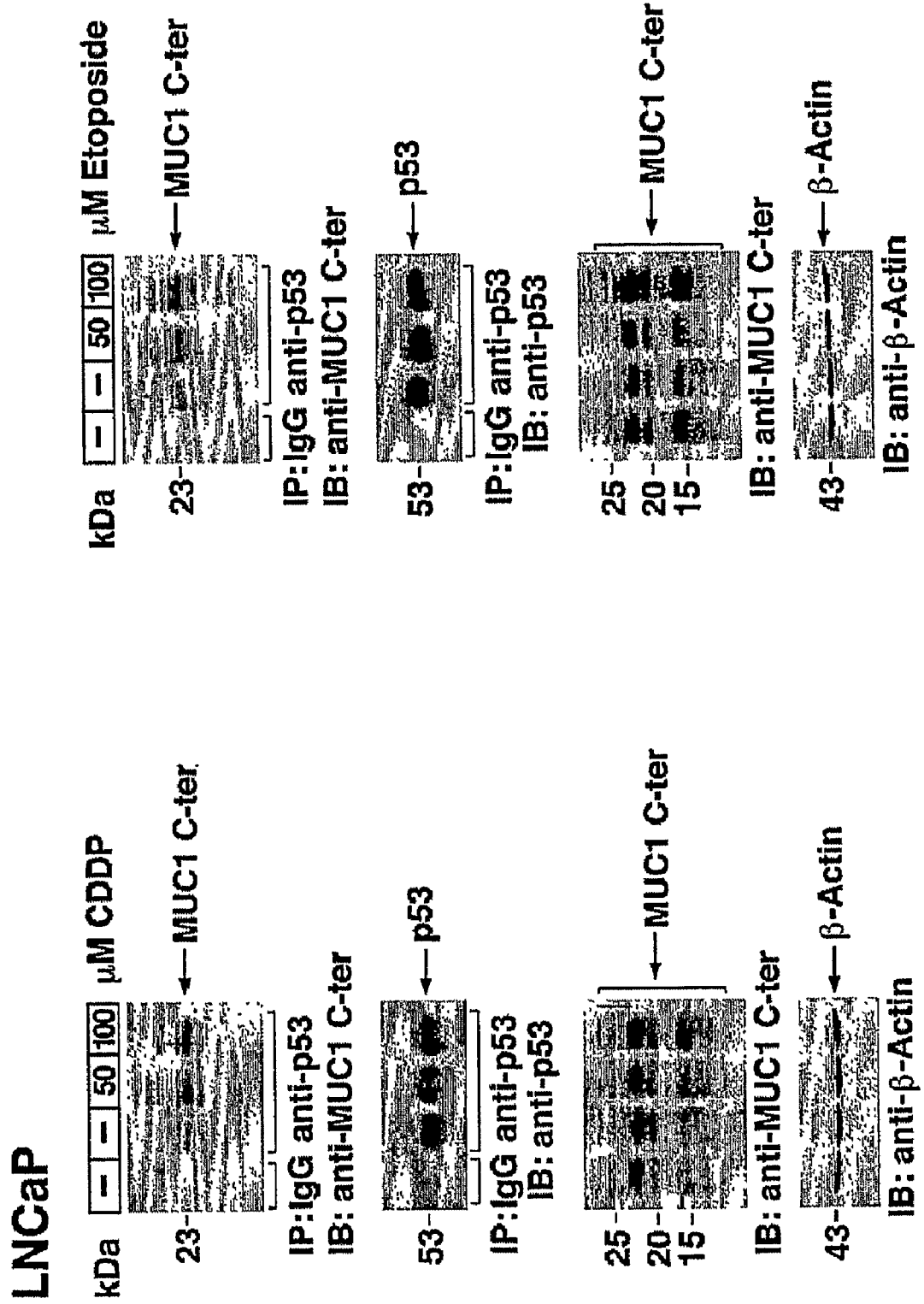

To investigate whether MUC1 associates with p53, lysates from HCT116/vector and HCT116/MUC1 cells were immunoprecipitated with anti-p53 antibody. Immunoblot analysis of the precipitates with anti-MUC1 C-ter antibody (that binds to the C-terminal 17 amino acids of the MUC1 cytoplasmic domain (MUC1-CD)) showed that the ~23-Da MUC1 C-ter coprecipitates with p53 (FIG. 1A, left panel). In contrast, there was no detectable MUC1 N-ter in the anti-p53 immunoprecipitates (FIG. 1A, left panel). Similar studies performed on human ZR-75-1 breast cancer cells confirmed coimmunoprecipitation of p53 and MUC1 (FIG. 1A, right panel). Densitometric scanning of the MUC1 signals obtained from the whole cell lysates, as compared to that after immunoprecipitation of the lysates with anti-p53 antibody, indicated that 4% and 5% of total MUC1 C-ter associates with p53 in HCT116/MUC1 and ZR-75-1 cells, respectively. Treatment of HCT116/MUC1 cells with cisplatin (FIG. 1B, left panel) or etoposide (FIG. 1B, right panel) resulted in an increase in the association of p53 and MUC1. Increased binding of endogenous MUC1 and p53 was also found in ZR-75-1 cells treated with cisplatin (FIG. 1C, left panel) or etoposide (FIG. 1C, right panel). Similar results were obtained with human MCF-7 breast and LNCaP prostate cancer cells (FIGS. 2A and 2B). These findings demonstrate that MUC1 associates with p53 constitutively and that this interaction is increased in the response of cells to DNA damage.

Example 3

MUC1-CD Binds Directly to p53

To define the sequences of MUC1-CD (amino acids 1-72) and p53 involved in the physical interaction between the two proteins, vectors expressing wild-type and deletion mutants of both were prepared (FIG. 3A, top panel). Incubation of purified $^{35}$S-labeled p53 with purified GST or GST-MUC1-CD demonstrated binding to MUC1-CD (FIG. 3A, bottom panel). Deletion of MUC1-CD from amino acids 9 to 46 abrogated the interaction, while MUC1-CD(1-51) was sufficient to form a complex with p53 in vitro (FIG. 3A, bottom panel). To confirm these findings, p53 and MUC1-CD deletion mutants were expressed in cells. As found in vitro, p53 formed complexes with MUC1-CD(1-72), but not with MUC1-CD(Δ9-46) (FIG. 3B). In addition, in vivo binding of p53 to MUC1-CD(1-51) was observed (FIG. 3B). To define the region within p53, GST-MUC1-CD was incubated with full-length p53 and certain deletion mutants. Deletion of the p53 C-terminus (amino acids 363-393) abrogated binding to MUC1-CD (FIG. 3C). In concert with these results, MUC1-CD formed complexes with p53(293-393) and p53(Δ1-50/Δ323-356) in vitro (FIG. 3C). Expression of Myc-MUC1-CD and the p53 deletion mutants in cells demonstrated that, as found in vitro, the interaction with MUC1-CD is abrogated by expression of p53(1-362) in vivo (FIG. 3D). The results also show that MUC1-CD associates with p53(293-393) in cells (FIG. 3D). These findings indicate that MUC1-CD (amino acids 9-46) binds directly to the p53 regulatory domain (amino acids 363-393).

Example 4

MUC1 Occupies the p53-Responsive p21 Gene Promoter

To determine if MUC1 is present in the p53 transcription complex, CHIP assays were performed on the p21 gene promoter with anti-MUC1 C-ter antibody or a control IgG. Immunoprecipitation of the two p53-responsive elements (p53REs) in the p21 gene promoter by anti-MUC1 antibody was analyzed by semi-quantitative PCR. Using HCT116/MUC1 and ZR-75-1 cells, occupancy of both p21 gene promoter p53REs by MUC1 was clearly detectable in anti-MUC1 antibody, and not the control IgG, precipitates (FIG. 4A, left panel). By contrast, there was no detectable MUC1 associated with a control region (CR) of the p21 gene promoter downstream to the p53REs (FIG. 4A, left panel). There was also no detectable MUC1 associated with the p21 gene PP (FIG. 4A, right panel). To determine if MUC1 occupies the p21 gene promoter together with p53, the anti-MUC1 antibody complexes were released, re-immunoprecipitated with anti-p53 antibody and then analyzed by PCR (Re-ChIP). The results show that anti-p53 antibody precipitated the p21 gene p53REs after their release from anti-MUC1, indicating that MUC1 occupies these elements with p53 (FIG. 4B).

A kinetic analysis after treatment of HCT116/MUC1 and ZR-75-1 cells with cisplatin or etoposide demonstrated that MUC1 occupancy of p21 gene p53RE2 increases in response to DNA damage and reaches maximal levels at 8-12 h of drug exposure (FIG. 4C). Moreover, treatment of HCT116/vector cells with cisplatin or etoposide increased p53 occupancy of the p21 gene p53RE2 (FIG. 4D, left panel). However, occupancy of the p21 gene p53RE2 by p53 was higher constitutively and after DNA damage in HCT116/MUC1 cells (FIG. 4D, left panel). The CREB-binding protein (CBP) functions as a histone acetyltransferase and coactivator of transcription. MUC1 expression was associated with an increase in CBP occupancy of the p21 gene p53RE2, indicating that MUC1 is associated with recruitment of CBP to the p53 transcription complex (FIG. 4D, left panel). In addition, occupancy of the p21 gene promoter by the histone deacetylase HDAC1 was decreased in the response of HCT116/MUC1 cells to cisplatin or etoposide as compared to that found in HCT116/vector cells (FIG. 4D, left panel). Acetylation of histone H4 was also more pronounced on the p21 gene promoter in MUC1-positive, as compared to MUC1-negative, HCT116 cells (FIG. 4D, left panel). ChIP studies of the p21 gene promoter in ZR-75-1/vector cells, which express endogenous MUC1, and MUC1-negative ZR-75-1/MUC1siRNA cells further demonstrated that MUC1 increases p53 and CBP occupancy, decreases HDAC1 occupancy and increases histone H4 acetylation (FIG. 4D, right panel). These findings indicate that endogenous, as well as exogenous, MUC1 is detectable on the p53REs in the p21 gene promoter and that MUC1 occupancy is associated with increased acetylation of histone H4.

Example 5

MUC1 Occupies the Bax Gene Proximal Promoter

To assess binding of MUC1 to other p53-responsive genes, ChIP analyses were performed on the p53RE in the Bax gene promoter (FIG. 5A). The results show that occupancy of the Bax gene p53RE by p53, but not by MUC1, is detectable in HCT116/MUC1 and ZR-75-1 cells (FIG. 5A, left four gels). Similar results were obtained after treatment of these cells with cisplatin or etoposide (data not shown). In contrast, p53 and MUC1 occupancy of the Bax gene PP was detectable in both HCT116/MUC1 and ZR-75-1 cells (FIG. 5A, right four gels). The results also show that anti-p53 antibody precipitated the Bax gene PP after release from anti-MUC1 (FIG. 5B, left panel). An antibody against the TATA-binding protein (TBP) also precipitated the Bax gene PP after release from anti-MUC1 antibody (FIG. 5B, right panel), indicating that MUC1 occupies this region with the basal transcription apparatus. MUC1 occupancy of the Bax gene PP was increased through 4-6 h and was maximal at 6-12 h after treatment with cisplatin or etoposide (FIG. 5C). Analysis of the Bax gene PP following treatment with cisplatin or etoposide also demonstrated that MUC1 expression is associated with i) increases in p53 binding and ii) decreases in occupancy of TFIIB and TAFII250, but not TBP (FIG. 5D). These findings indicate that MUC1 occupies the Bax gene PP with p53 and interferes with assembly of the basal transcription apparatus in the DNA damage response.

Example 6

MUC1-CD Regulates Transactivation of the p21 and Bax Gene Promoters

Figure 6D:
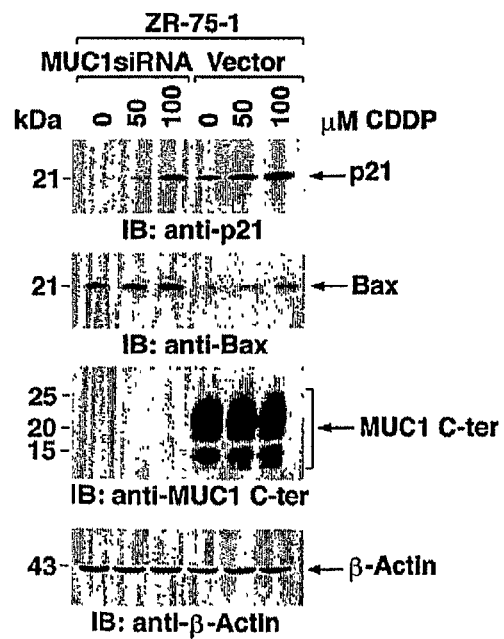
Figure 6D:
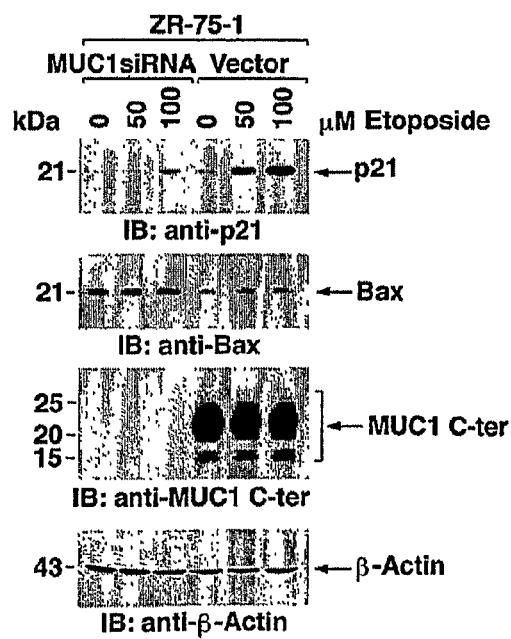

To determine if MUC1 affects activation of the p21 gene promoter, HCT116/vector cells and HCT116/MUC1 cells were transfected with a p21 gene promoter-Luc reporter vector (p21-Luc). Basal levels of p21 gene promoter activity were increased in HCT116/MUC1 as compared to HCT116/vector cells (FIG. 6A, left panel). In addition, cisplatin- or etoposide-induced activation of p21-Luc was enhanced as a result of MUC1 expression (FIG. 6A, left panel). For comparison, similar studies were performed with the Bax gene promoter-Luc reporter (Bax-Luc). In contrast to p21-Luc, basal and DNA damage-induced levels of Bax-Luc activity were decreased by MUC1 expression (FIG. 6A, right panel). Similar results were obtained with the ZR-75-1/vector and ZR-75-1/MUC1siRNA cells (FIG. 6B). Immunoblot analysis of lysates from control and cisplatin- or etoposide-treated HCT116 cells demonstrated that constitutive and drug-induced expression of p21 was increased in HCT116/MUC1 cells, as compared to HCT116/vector cells (FIG. 6C). By contrast, levels of Bax were attenuated in control and cisplatin- or etoposide-treated HCT116/MUC1 cells (FIG. 6C). Experiments in which MUC1 expression was inhibited by MUC1 siRNA showed that MUC1 expression was also associated with selective basal and drug-induced increases in p21 protein in ZR-75-1 cells (FIG. 6D). These findings indicate that MUC1 selectively coactivates p21 gene transcription in the response to DNA damage.

Example 7

MUC1 Activates the Growth Arrest and Survival Response to DNA Damage

Consistent with the increases in p21 gene expression by MUC1, treatment of both HCT116/vector and HCT116/MUC1 cells with cisplatin or etoposide for 48 h resulted in G1 arrest of cell cycle progression. However, the HCT116/MUC1 cells exhibited greater accumulation in G1 phase than that found with HCT116/vector cells. Additional experiments performed at 12 h to 48 h of drug exposure confirmed that MUC1 increases the percentage of cells that exhibit G1 phase arrest (FIG. 7A). Treatment of ZR-75-1/vector and ZR-75-1/MUC1siRNA cells with cisplatin or etoposide provided further evidence for involvement of MUC1 in conferring an increase in the arrest of cells at G1 phase (FIG. 7B). Activation of the p53-induced growth arrest response can be irreversible or associated with repair and survival [Oren (2003) Cell Death Differ. 10:431-442; Weiss (2003) Cancer Cell 4:425-429]. To distinguish between these potential outcomes, HCT116 cells were treated with cisplatin or etoposide and their survival was monitored by colony formation. Clonogenic survival was higher for cisplatin- or etoposide-treated HCT116/MUC1 as compared to HCT116/vector cells (FIG. 7C and FIG. 8A). Clonogenic survival of ZR-75-1 cells following cisplatin or etoposide treatment (FIG. 7D and FIG. 8B) was also increased by MUC1 expression, indicating that this response is not cell-type dependent. These findings indicate that MUC1 promotes growth arrest and survival in the response to DNA damage.

Example 8

MUC1 Regulates the p53-Dependent Growth Arrest and Apoptotic Responses to DNA Damage in HCT116 Cells To determine if the effects of MUC1 on growth arrest and survival are dependent on p53, HCT116/p53$^{-/-}$ cells were transfected to express an empty vector or MUC1. Immunoblot analysis of two separately isolated HCT116/p53$^{-/-}$/MUC1 clones confirmed expression of MUC1 N-ter and C-ter at levels similar to that in HCT116/MUC1 cells (FIG. 9A). As controls, immunoblotting was also performed on lysates from HCT116 and HCT116/p53$^{-/-}$ cells stably transfected with the empty vector (FIG. 9A). Importantly and in contrast to HCT116/MUC1 cells, MUC1 occupancy of the p53REs in the p21 gene promoter was undetectable in HCT116/p53−/−/MUC1 cells (FIG. 9B), indicating that association of MUC1 with these p53REs is dependent on p53. In contrast, the absence of p53 in HCT116/p53$^{-/-}$/MUC1 cells had little effect on MUC1 C-ter occupancy of the Bax gene PP (FIG. 9B). Similar results were obtained with the two independently isolated HCT116/p53$^{-/-}$/MUC1 cell clones and in the response to DNA damage (data not shown). In addition, compared to HCT116/MUC1 cells (FIG. 6A, left panel), the effects of MUC1 on DNA damage-induced activation of p21-Luc were substantially decreased in HCT116/p53−/−/MUC1 cells (FIG. 9C, left). Conversely, MUC1 was as effective in suppressing Bax-Luc expression in both HCT116/MUC1 (FIG. 6A, right) and HCT116/p53$^{-/-}$/MUC1 cells (FIG. 9C, right panel). Consistent with these results, the effects of MUC1 on DNA damage-induced expression of p21 were p53-dependent, while suppression of Bax by MUC1 was independent of p53 (FIG. 9D). The effects of MUC1 on DNA damage-induced growth arrest were also dependent on p53 (FIG. 9E). The results further demonstrate that MUC1 attenuates p53-dependent, as well as p53-independent, apoptosis in response to DNA damage (FIG. 9F).

Example 9

MUC1 Silencing Attenuates the p53-Dependent Growth Arrest Response and Increases the p53-Dependent Apoptotic Response to DNA Damage in ZR-75-1 Cells p53 was knocked-down in the ZR-75-1/vector and ZR-75-1/MUC1siRNA cells by infection with an adenovirus expressing a p53siRNA (Ad.p53siRNA) (FIG. 10A). Knocking-down p53 reduced MUC1 occupancy of the p53REs in the p21 gene promoter (FIG. 10B), consistent with a p53-dependent mechanism. However, knocking-down p53 had little effect on MUC1 occupancy of the Bax gene PP (FIG. 10B). In addition, MUC1 increased DNA damage-induced p21-Luc activation in ZR-75-1 cells by a p53-dependent mechanism (FIG. 10C, left panel compared to FIG. 6B, left panel). Moreover, MUC1-mediated suppression of Bax-Luc was similar in ZR-75-1 cells with basal (FIG. 6B, right panel) or knocked-down (FIG. 10C, right panel) levels of p53 expression. The effects of MUC1 on DNA damage-induced expression of p21 were attenuated in the absence of p53 (FIG. 10D), while MUC1 suppressed Bax expression independently of changes in p53 levels (FIG. 10D). In concert with these results, MUC1 potentiated DNA damage-induced growth arrest in large part by a p53-dependent mechanism (FIG. 10E). MUC1 also blocked p53-dependent and p53-independent apoptosis in the response of ZR-75-1 cells to DNA damage (FIG. 10F).

A number of embodiments of the invention have been described. Nevertheless, it will be understood that various modifications may be made without departing from the spirit and scope of the invention. Accordingly, other embodiments are within the scope of the following claims.

What is claimed is:

1. An in vivo method of inhibiting binding of MUC to p53 in a cancer cell that expresses MUC, the method comprising:
   (a) identifying a subject as having a cancer that expresses MUC1; and
   (b) administering to the subject a peptide comprising amino acids 1-51 of SEQ ID NO:2 or fragments thereof, wherein the peptide inhibits binding of p53 to the cytoplasmic domain of MUC1.

2. The method of claim 1, wherein the subject is a human subject.

3. The method of claim 1, wherein the cancer cell is a breast cancer cell.

4. The method of claim 1, wherein the cancer cell is selected from the group consisting of a lung cancer, colon cancer, pancreatic cancer, renal cancer, stomach cancer, liver cancer, bone cancer, hematological cancer, neural tissue cancer, melanoma, ovarian cancer, testicular cancer, prostate cancer, cervical cancer, vaginal cancer, or bladder cancer cell.

5. The method of claim 1, further comprising exposing the subject to one or more genotoxic agents.

6. The method of claim 5, wherein the one or more genotoxic agents comprise one or more forms of ionizing radiation.

7. The method of claim 5, wherein the one or more genotoxic agents comprise one or more chemotherapeutic agents.

8. The method of claim 7, wherein the one or more chemotherapeutic agents are selected from the group consisting of cisplatin, carboplatin, procarbazine, mechlorethamine, cyclophosphamide, camptothecin, ifosfamide, melphalan, chlorambucil, bisulfan, nitrosurea, dactinomycin, daunorubicin, doxorubicin, bleomycin, plicomycin, mitomycin, etoposide, verampil, podophyllotoxin, tamoxifen, taxol, transplatinum, 5-fluorouracil, vincristin, vinblastin, methotrexate, and an analog of any of the aforementioned.

* * * * *

UNITED STATES PATENT AND TRADEMARK OFFICE
CERTIFICATE OF CORRECTION

| | | |
|---|---|---|
| PATENT NO. | : 7,931,904 B2 | Page 1 of 1 |
| APPLICATION NO. | : 11/816402 | |
| DATED | : April 26, 2011 | |
| INVENTOR(S) | : Donald W. Kufe | |

It is certified that error appears in the above-identified patent and that said Letters Patent is hereby corrected as shown below:

In column 1, lines 6-10, delete paragraph and insert
--This invention was made with government support under Grant Nos. CA097098 and CA29431 awarded by the National Cancer Institute of the National Institutes of Health and Grant No. BC022158 awarded by the U.S. Army. The government has certain rights in the invention.-- therefor.

Signed and Sealed this
Ninth Day of August, 2011

David J. Kappos
*Director of the United States Patent and Trademark Office*

SEQUENCE LISTING

<160> NUMBER OF SEQ ID NOS: 24

<210> SEQ ID NO 1
<211> LENGTH: 393
<212> TYPE: PRT
<213> ORGANISM: Homo sapiens

<400> SEQUENCE: 1

```
Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Pro Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
        115                 120                 125

Ala Leu Asn Lys Met Phe Cys Gln Leu Ala Lys Thr Cys Pro Val Gln
    130                 135                 140

Leu Trp Val Asp Ser Thr Pro Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
        195                 200                 205

Arg Asn Thr Phe Arg His Ser Val Val Pro Tyr Glu Pro Pro Glu
    210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270
```

```
His Val Cys Ala Cys Pro Gly Arg Asp Arg Arg Thr Glu Glu Asn
    275                 280                 285

Leu Arg Lys Lys Gly Glu Pro His His Glu Leu Pro Pro Gly Ser Thr
290                 295                 300

Lys Arg Ala Leu Pro Asn Asn Thr Ser Ser Pro Gln Pro Lys Lys
305                 310                 315                 320

Lys Pro Leu Asp Gly Glu Tyr Phe Thr Leu Gln Ile Arg Gly Arg Glu
                325                 330                 335

Arg Phe Glu Met Phe Arg Glu Leu Asn Glu Ala Leu Glu Leu Lys Asp
                340                 345                 350

Ala Gln Ala Gly Lys Glu Pro Gly Gly Ser Arg Ala His Ser Ser His
            355                 360                 365

Leu Lys Ser Lys Lys Gly Gln Ser Thr Ser Arg His Lys Lys Leu Met
370                 375                 380

Phe Lys Thr Glu Gly Pro Asp Ser Asp
385                 390

<210> SEQ ID NO 2
<211> LENGTH: 72
<212> TYPE: PRT
<213> ORGANISM: Homo sapiens

<400> SEQUENCE: 2

Cys Gln Cys Arg Arg Lys Asn Tyr Gly Gln Leu Asp Ile Phe Pro Ala
1               5                   10                  15

Arg Asp Thr Tyr His Pro Met Ser Glu Tyr Pro Thr Tyr His Thr His
                20                  25                  30

Gly Arg Tyr Val Pro Pro Ser Ser Thr Asp Arg Ser Pro Tyr Glu Lys
            35                  40                  45

Val Ser Ala Gly Asn Gly Gly Ser Ser Leu Ser Tyr Thr Asn Pro Ala
    50                  55                  60

Val Ala Ala Thr Ser Ala Asn Leu
65                  70

<210> SEQ ID NO 3
<211> LENGTH: 477
<212> TYPE: PRT
<213> ORGANISM: Homo sapiens

<400> SEQUENCE: 3

Met Thr Pro Gly Thr Gln Ser Leu Phe Phe Leu Leu Leu Leu Leu Thr
1               5                   10                  15

Val Leu Thr Val Val Thr Gly Ser Gly His Ala Ser Ser Thr Pro Gly
                20                  25                  30

Gly Glu Lys Glu Thr Ser Ala Thr Gln Arg Ser Ser Met Pro Ser Ser
            35                  40                  45

Thr Glu Lys Lys Val Val Ser Met Thr Ser Ser Val Leu Ser Ser His
    50                  55                  60

Ser Pro Gly Ser Gly Ser Ser Thr Thr Gln Gly Gln Asp Val Ser Leu
65                  70                  75                  80

Ala Pro Ala Thr Glu Pro Ala Ser Gly Ser Ala Ala Thr Trp Gly Gln
                85                  90                  95

Asp Val Thr Ser Val Pro Val Thr Arg Pro Ala Pro Gly Ser Thr Thr
                100                 105                 110

Ser Pro Ala Gln Asp Val Thr Ser Ala Pro Asp Thr Arg Pro Ala Leu
            115                 120                 125

Gly Ser Thr Ala Pro Pro Val His Gly Val Thr Ser Ala Pro Asp Thr
```

```
                130                 135                 140
Arg Pro Thr Leu Gly Ser Thr Ala Pro Pro Val His Gly Val Thr Ser
145                 150                 155                 160

Ala Pro Asp Thr Arg Pro Thr Leu Gly Ser Thr Ala Pro Pro Val His
                165                 170                 175

Asn Val Thr Ser Ala Ser Gly Ser Ala Ser Gly Ser Ala Ser Thr Leu
                180                 185                 190

Val His Asn Gly Thr Ser Ala Arg Ala Thr Thr Thr Pro Ala Ser Lys
                195                 200                 205

Ser Thr Pro Phe Ser Ile Pro Ser His His Ser Asp Thr Pro Thr Thr
210                 215                 220

Leu Thr Ser His Ser Thr Lys Thr Asp Ala Ser Ser Thr His His Ser
225                 230                 235                 240

Thr Val Ser Pro Leu Thr Ser Ser Asn His Ser Thr Ser Pro Gln Leu
                245                 250                 255

Ser Ile Gly Val Ser Phe Phe Leu Ser Phe His Ile Ser Asn Leu
                260                 265                 270

Gln Phe Asn Ser Ser Leu Glu Asp Pro Ser Thr Asn Tyr Tyr Gln Glu
                275                 280                 285

Leu Gln Arg Asp Ile Ser Glu Leu Ile Leu Gln Ile Tyr Lys Gln Gly
                290                 295                 300

Asp Phe Leu Gly Val Ser Asn Ile Lys Phe Arg Pro Gly Ser Val Val
305                 310                 315                 320

Val Gln Ser Thr Leu Ala Phe Arg Glu Gly Thr Thr Asn Val His Asp
                325                 330                 335

Val Glu Ala Gln Phe Asn Gln His Lys Thr Glu Ala Ala Ser Arg Tyr
                340                 345                 350

Asn Leu Thr Ile Ser Asp Val Ser Val Ser Asp Val Pro Phe Pro Phe
                355                 360                 365

Ser Ala Gln Ser Gly Ala Gly Val Pro Gly Trp Gly Ile Ala Leu Leu
                370                 375                 380

Val Leu Val Cys Val Leu Val Ala Leu Ala Ile Val Tyr Leu Ile Ala
385                 390                 395                 400

Leu Ala Val Cys Gln Cys Arg Arg Lys Asn Tyr Gly Gln Leu Asp Ile
                405                 410                 415

Phe Pro Ala Arg Asp Ala Tyr His Pro Met Ser Glu Tyr Pro Thr Tyr
                420                 425                 430

His Thr His Gly Ala Arg Thr Tyr Val Pro Pro Ser Ser Thr Asn Arg
                435                 440                 445

Ser Pro Tyr Glu Lys Val Ser Glu Gly Asn Gly Gly Ser Ser Leu Ser
450                 455                 460

Tyr Thr Asn Pro Ala Val Ala Ala Thr Ser Ala Asn Leu
465                 470                 475

<210> SEQ ID NO 4
<211> LENGTH: 38
<212> TYPE: PRT
<213> ORGANISM: Homo sapiens

<400> SEQUENCE: 4

Gly Gln Leu Asp Ile Phe Pro Ala Arg Asp Ala Tyr His Pro Met Ser
1               5                   10                  15

Glu Tyr Pro Thr Tyr His Thr His Gly Arg Tyr Val Pro Pro Ser Ser
                20                  25                  30

Thr Asn Arg Ser Pro Tyr
```

-continued

```
<210> SEQ ID NO 5
<211> LENGTH: 51
<212> TYPE: PRT
<213> ORGANISM: Homo sapiens

<400> SEQUENCE: 5

Cys Gln Cys Arg Arg Lys Asn Tyr Gly Gln Leu Asp Ile Phe Pro Ala
1               5                   10                  15

Arg Asp Ala Tyr His Pro Met Ser Glu Tyr Pro Thr Tyr His Thr His
            20                  25                  30

Gly Arg Tyr Val Pro Pro Ser Ser Thr Asn Arg Ser Pro Tyr Glu Lys
        35                  40                  45

Val Ser Glu
    50

<210> SEQ ID NO 6
<211> LENGTH: 31
<212> TYPE: PRT
<213> ORGANISM: Homo sapiens

<400> SEQUENCE: 6

Arg Ala His Ser Ser His Leu Lys Ser Lys Lys Gly Gln Ser Thr Ser
1               5                   10                  15

Arg His Lys Lys Leu Met Phe Lys Thr Glu Gly Pro Asp Ser Asp
            20                  25                  30

<210> SEQ ID NO 7
<211> LENGTH: 21
<212> TYPE: DNA
<213> ORGANISM: Homo sapiens

<400> SEQUENCE: 7
aagttcagtg cccagctcta c                                             21

<210> SEQ ID NO 8
<211> LENGTH: 21
<212> TYPE: RNA
<213> ORGANISM: Homo sapiens

<400> SEQUENCE: 8
guucagugcc cagcucuacu u                                             21

<210> SEQ ID NO 9
<211> LENGTH: 21
<212> TYPE: RNA
<213> ORGANISM: Homo sapiens
<220> FEATURE:
<221> NAME/KEY: modified_base
<222> LOCATION: (20)..(21)
<223> OTHER INFORMATION: u = 2'-deoxythymidine (dT)

<400> SEQUENCE: 9
guucagugcc cagcucuacu u                                             21

<210> SEQ ID NO 10
<211> LENGTH: 21
<212> TYPE: RNA
<213> ORGANISM: Homo sapiens

<400> SEQUENCE: 10
guagagcugg gcacugaacu u                                             21
```

```
<210> SEQ ID NO 11
<211> LENGTH: 21
<212> TYPE: RNA
<213> ORGANISM: Homo sapiens
<220> FEATURE:
<221> NAME/KEY: modified_base
<222> LOCATION: (20)..(21)
<223> OTHER INFORMATION: u = 2'-deoxythymidine (dT)

<400> SEQUENCE: 11
guagagcugg gcacugaacu u                                              21

<210> SEQ ID NO 12
<211> LENGTH: 19
<212> TYPE: RNA
<213> ORGANISM: Homo sapiens

<400> SEQUENCE: 12
gguaccauca auguccacg                                                 19

<210> SEQ ID NO 13
<211> LENGTH: 19
<212> TYPE: RNA
<213> ORGANISM: Homo sapiens

<400> SEQUENCE: 13
cguggacauu gaugguacc                                                 19

<210> SEQ ID NO 14
<211> LENGTH: 21
<212> TYPE: DNA
<213> ORGANISM: Artificial
<220> FEATURE:
<223> OTHER INFORMATION: Artificial primer

<400> SEQUENCE: 14
ggtgcttctg ggagaggtga c                                              21

<210> SEQ ID NO 15
<211> LENGTH: 21
<212> TYPE: DNA
<213> ORGANISM: Artificial
<220> FEATURE:
<223> OTHER INFORMATION: Artificial primer

<400> SEQUENCE: 15
tgacccactc tggcaggcaa g                                              21

<210> SEQ ID NO 16
<211> LENGTH: 21
<212> TYPE: DNA
<213> ORGANISM: Artificial
<220> FEATURE:
<223> OTHER INFORMATION: Artificial primer

<400> SEQUENCE: 16
ggaagtgccc tcctgcagca c                                              21

<210> SEQ ID NO 17
<211> LENGTH: 21
<212> TYPE: DNA
<213> ORGANISM: Artificial
<220> FEATURE:
<223> OTHER INFORMATION: Artificial primer

<400> SEQUENCE: 17
```

-continued cggcgaatcc gcgcccagct c                                              21

<210> SEQ ID NO 18
<211> LENGTH: 21
<212> TYPE: DNA
<213> ORGANISM: Artificial
<220> FEATURE:
<223> OTHER INFORMATION: Artificial primer

<400> SEQUENCE: 18
gattgggcca ctgcactcca g                                              21

<210> SEQ ID NO 19
<211> LENGTH: 18
<212> TYPE: DNA
<213> ORGANISM: Artificial
<220> FEATURE:
<223> OTHER INFORMATION: Artificial primer

<400> SEQUENCE: 19
tgactaaaaa ctgagtgg                                                  18

<210> SEQ ID NO 20
<211> LENGTH: 21
<212> TYPE: DNA
<213> ORGANISM: Artificial
<220> FEATURE:
<223> OTHER INFORMATION: Artificial primer

<400> SEQUENCE: 20
cctgctgatc tatcagcaca g                                              21

<210> SEQ ID NO 21
<211> LENGTH: 21
<212> TYPE: DNA
<213> ORGANISM: Artificial
<220> FEATURE:
<223> OTHER INFORMATION: Artificial primer

<400> SEQUENCE: 21
gctggtctct gaactcccag a                                              21

<210> SEQ ID NO 22
<211> LENGTH: 21
<212> TYPE: DNA
<213> ORGANISM: Artificial
<220> FEATURE:
<223> OTHER INFORMATION: Artificial primer

<400> SEQUENCE: 22
cgtgggctat attgctagat c                                              21

<210> SEQ ID NO 23
<211> LENGTH: 21
<212> TYPE: DNA
<213> ORGANISM: Artificial
<220> FEATURE:
<223> OTHER INFORMATION: Artificial primer

<400> SEQUENCE: 23
gtccaatcgc agctctaatg c                                              21

<210> SEQ ID NO 24
<211> LENGTH: 72
<212> TYPE: PRT
<213> ORGANISM: Homo sapiens

```
<400> SEQUENCE: 24

Cys Gln Cys Arg Arg Lys Asn Tyr Gly Gln Leu Asp Ile Phe Pro Ala
1               5                   10                  15

Arg Asp Ala Tyr His Pro Met Ser Glu Tyr Pro Thr Tyr His Thr His
            20                  25                  30

Gly Arg Tyr Val Pro Pro Ser Ser Thr Asn Arg Ser Pro Tyr Glu Lys
        35              40                  45

Val Ser Glu Gly Asn Gly Gly Ser Ser Leu Ser Tyr Thr Asn Pro Ala
    50              55                  60

Val Ala Ala Thr Ser Ala Asn Leu
65              70
```